US012156897B2

(12) United States Patent
Carson et al.

(10) Patent No.: US 12,156,897 B2
(45) Date of Patent: Dec. 3, 2024

(54) MAGNESIUM-CONTAINING OXYTOCIN FORMULATIONS AND METHODS OF USE

(71) Applicant: TONIX PHARMA LIMITED, Dublin (IE)

(72) Inventors: Dean Carson, Palo Alto, CA (US); David C. Yeomans, Sunnyvale, CA (US)

(73) Assignee: TONIX PHARMA LIMITED, Dublin (IE)

( * ) Notice: Subject to any disclaimer, the term of this patent is extended or adjusted under 35 U.S.C. 154(b) by 513 days.

(21) Appl. No.: 16/093,104

(22) PCT Filed: Apr. 12, 2017

(86) PCT No.: PCT/US2017/027265
§ 371 (c)(1),
(2) Date: Oct. 11, 2018

(87) PCT Pub. No.: WO2017/180781
PCT Pub. Date: Oct. 19, 2017

(65) Prior Publication Data
US 2019/0175686 A1 Jun. 13, 2019

Related U.S. Application Data

(60) Provisional application No. 62/321,654, filed on Apr. 12, 2016.

(51) Int. Cl.
| | | |
|---|---|---|
| A61K 38/095 | (2019.01) | |
| A61K 9/00 | (2006.01) | |
| A61K 9/08 | (2006.01) | |
| A61K 31/194 | (2006.01) | |
| A61K 33/06 | (2006.01) | |
| A61K 33/14 | (2006.01) | |
| A61K 47/02 | (2006.01) | |
| A61K 47/12 | (2006.01) | |
| A61M 15/00 | (2006.01) | |
| A61M 15/08 | (2006.01) | |
| A61P 25/00 | (2006.01) | |
| A61P 25/22 | (2006.01) | |

(52) U.S. Cl.
CPC .......... *A61K 38/095* (2019.01); *A61K 9/0043* (2013.01); *A61K 9/0048* (2013.01); *A61K 9/006* (2013.01); *A61K 9/0073* (2013.01); *A61K 9/08* (2013.01); *A61K 31/194* (2013.01); *A61K 33/06* (2013.01); *A61K 33/14* (2013.01); *A61K 47/02* (2013.01); *A61K 47/12* (2013.01); *A61M 15/009* (2013.01); *A61M 15/08* (2013.01); *A61P 25/00* (2018.01); *A61P 25/22* (2018.01)

(58) Field of Classification Search
None
See application file for complete search history.

(56) References Cited

U.S. PATENT DOCUMENTS

| | | | |
|---|---|---|---|
| 1,936,364 | A | 11/1933 | Pasternack |
| 2,260,004 | A | 10/1941 | Davenport |
| 2,938,891 | A | 5/1960 | Velluz |
| 3,076,797 | A | 2/1963 | Velluz |
| 4,213,968 | A | 7/1980 | Kastin |
| 4,464,378 | A | 8/1984 | Hussain |
| 4,486,441 | A | 12/1984 | Fozard |
| 4,885,287 | A | 12/1989 | Hussain |
| 5,482,931 | A | 1/1996 | Harris |
| 5,603,943 | A | 2/1997 | Yanagawa |
| 5,624,898 | A | 4/1997 | Frey, II |
| 5,656,721 | A | 8/1997 | Albert |
| 5,766,633 | A | 6/1998 | Milstein |
| 5,837,809 | A | 11/1998 | Grandy |
| 5,859,048 | A | 1/1999 | Oohashi |
| 5,889,110 | A | 3/1999 | Hutchinson |
| 5,914,129 | A | 6/1999 | Mauskop |
| 5,988,449 | A | 11/1999 | Fuchs |
| 6,034,175 | A | 3/2000 | Hutchinson |
| 6,054,462 | A | 4/2000 | François |
| 6,090,368 | A | 7/2000 | Zia |
| 6,139,861 | A | 10/2000 | Friedman |
| 6,143,278 | A | 11/2000 | Elkhoury |
| 6,166,039 | A | 12/2000 | Yaksh |
| 6,180,603 | B1 | 1/2001 | Frey, II |

(Continued)

FOREIGN PATENT DOCUMENTS

| | | |
|---|---|---|
| AU | 2006282799 B2 | 3/2007 |
| DE | 431291 A1 | 10/1994 |

(Continued)

OTHER PUBLICATIONS

Chan et al. (Journal of Pharmacology and Experiments Therapeutics Jul. 1974, 190(1) 77-87).*

(Continued)

*Primary Examiner* — James H Alstrum-Acevedo
*Assistant Examiner* — Tara L Martinez
(74) *Attorney, Agent, or Firm* — HALEY GUILIANO LLP; James F. Haley, Jr.; Mihaela D. Danca

(57) ABSTRACT

Disclosed are methods and compositions for the treatment of autism spectrum disorder, related disorders and symptoms of such disorders, comprising co-administration of an oxytocin peptide and magnesium ions. Co-administration of an oxytocin peptide and magnesium ions results in a synergistic or enhanced effect on reducing social and communication deficits in a patient suffering from an autism spectrum disorder.

29 Claims, 2 Drawing Sheets

Specification includes a Sequence Listing.

(56) References Cited

U.S. PATENT DOCUMENTS

| | | |
|---|---|---|
| 6,218,192 B1 | 4/2001 | Altura et al. |
| 6,262,021 B1 | 7/2001 | Uvnäs-Moberg |
| 6,313,093 B1 | 11/2001 | Frey, II |
| 6,342,478 B1 | 1/2002 | Frey, II |
| 6,407,061 B1 | 6/2002 | Frey, II |
| 6,413,499 B1 | 7/2002 | Clay |
| 6,677,346 B1 | 1/2004 | Achari |
| 6,815,424 B2 | 11/2004 | Vickery |
| 6,825,203 B2 | 11/2004 | Pasternak |
| 6,881,423 B2 | 4/2005 | Dohi |
| 6,949,509 B2 | 9/2005 | Woodrow |
| 6,991,785 B2 | 1/2006 | Frey, II |
| 7,163,921 B1 | 1/2007 | Ishiyama |
| 7,220,725 B2 | 5/2007 | Shulov |
| 7,273,618 B2 | 9/2007 | Frey, II |
| 7,452,868 B2 | 11/2008 | Kuzma |
| 7,714,105 B2 | 5/2010 | Moberg |
| 7,784,460 B2 | 8/2010 | Djupesland |
| 7,854,227 B2 | 12/2010 | Djupesland |
| 8,198,240 B2 | 6/2012 | Yeomans |
| 8,202,838 B2 | 6/2012 | Yeomans |
| 8,211,405 B2 | 7/2012 | Mueller-Waltz |
| 8,246,935 B2 | 8/2012 | Mueller-Waltz |
| 8,252,745 B2 | 8/2012 | Yeomans |
| 8,258,096 B2 | 9/2012 | Yeomans |
| 8,414,867 B2 | 4/2013 | Mueller-Waltz |
| 8,501,691 B2 | 8/2013 | Yeomans |
| 8,551,949 B2 | 10/2013 | Toll |
| 8,921,306 B2 | 12/2014 | Fairlie |
| 9,034,821 B2 | 5/2015 | Uvnäs-Moberg |
| 9,238,053 B2 | 1/2016 | Toll |
| 9,629,894 B2 | 4/2017 | Yeomans |
| 11,389,473 B2 | 7/2022 | Yeomans |
| 2001/0010827 A1 | 8/2001 | Altura |
| 2001/0043915 A1 | 11/2001 | Frey, II |
| 2001/0055607 A1 | 12/2001 | Levin |
| 2002/0028786 A1 | 3/2002 | Frey, II |
| 2002/0072498 A1 | 6/2002 | Frey, II |
| 2002/0082215 A1 | 6/2002 | Frey, II |
| 2002/0141971 A1 | 10/2002 | Frey, II |
| 2002/0169102 A1 | 11/2002 | Frey, II |
| 2003/0072793 A1 | 4/2003 | Frey, II |
| 2003/0077300 A1 | 4/2003 | Wermeling |
| 2003/0104085 A1 | 6/2003 | Yeomans |
| 2003/0119892 A1 | 6/2003 | Caldwell |
| 2003/0165434 A1 | 9/2003 | Reinhard |
| 2003/0185872 A1 | 10/2003 | Kochinke |
| 2003/0215398 A1 | 11/2003 | Frey, II |
| 2003/0223981 A1 | 12/2003 | Mochly-Rosen |
| 2003/0229025 A1 | 12/2003 | Xiao |
| 2004/0105889 A1 | 6/2004 | Ryde |
| 2004/0120896 A1 | 6/2004 | Dugger, III |
| 2004/0122013 A1 | 6/2004 | Guerrini |
| 2004/0152707 A1 | 8/2004 | Tulshian |
| 2004/0204366 A1 | 10/2004 | Pasternak |
| 2004/0258757 A1 | 12/2004 | Bosch |
| 2004/0259775 A1 | 12/2004 | Kyle |
| 2005/0142072 A1 | 6/2005 | Birch |
| 2005/0153885 A1 | 7/2005 | Yun |
| 2005/0272642 A1 | 12/2005 | Frey, II |
| 2006/0009413 A1 | 1/2006 | Frey, II |
| 2006/0009414 A1 | 1/2006 | Frey, II |
| 2006/0014716 A1 | 1/2006 | Frey, II |
| 2006/0030542 A1 | 2/2006 | Frey, II |
| 2006/0039995 A1 | 2/2006 | Frey, II |
| 2006/0063699 A1 | 3/2006 | Larsen |
| 2006/0135437 A1 | 6/2006 | Stoehr |
| 2006/0142181 A1 | 6/2006 | Miller |
| 2006/0159626 A1 | 7/2006 | Frey, II |
| 2006/0188496 A1 | 8/2006 | Bentz |
| 2006/0216317 A1 | 9/2006 | Reinhard |
| 2006/0252685 A1 | 11/2006 | Gould |
| 2007/0004743 A1 | 1/2007 | Xiao |
| 2007/0016968 A1 | 1/2007 | Kyrkanides |
| 2007/0054843 A1 | 3/2007 | Yeomans |
| 2007/0071690 A1 | 3/2007 | Mueller-Walz |
| 2007/0093420 A1 | 4/2007 | Yeomans |
| 2008/0305077 A1 | 12/2008 | Frey |
| 2009/0181880 A1 | 7/2009 | Yeomans |
| 2009/0291900 A1 | 11/2009 | Yeomans |
| 2009/0317377 A1 | 12/2009 | Yeomans |
| 2010/0035854 A1 | 2/2010 | Mueller-Walz |
| 2010/0080797 A1 | 4/2010 | Yeomans |
| 2011/0021426 A1 | 1/2011 | Toll |
| 2011/0237508 A1 | 9/2011 | Amorij |
| 2011/0250212 A1 | 10/2011 | Yeomans |
| 2012/0028898 A1 | 2/2012 | Yeomans |
| 2012/0172304 A1* | 7/2012 | Leonard ................ A61P 5/10 |
| | | 514/11.6 |
| 2012/0244196 A1 | 9/2012 | Okubo |
| 2012/0252894 A1 | 10/2012 | Rashid |
| 2012/0322736 A1 | 12/2012 | Yeomans |
| 2013/0130985 A1 | 5/2013 | Alewood |
| 2013/0196908 A1 | 8/2013 | Toll |
| 2013/0231279 A1 | 9/2013 | Feifel |
| 2014/0147519 A1 | 5/2014 | McPhail |
| 2014/0342021 A1 | 11/2014 | Liu |
| 2017/0368095 A1 | 12/2017 | Yeomans |

FOREIGN PATENT DOCUMENTS

| | | |
|---|---|---|
| EP | 0122036 B1 | 2/1989 |
| EP | 1077070 A2 | 2/2001 |
| EP | 0681833 B1 | 6/2001 |
| EP | 0696208 B1 | 8/2001 |
| EP | 0710122 B1 | 12/2001 |
| EP | 1422240 A2 | 5/2004 |
| EP | 1466610 A1 | 10/2004 |
| EP | 1468690 A1 | 10/2004 |
| EP | 1239845 B1 | 3/2005 |
| EP | 1025840 B1 | 6/2005 |
| EP | 1689360 A1 | 8/2006 |
| EP | 1409518 B1 | 12/2007 |
| EP | 1121935 B1 | 8/2008 |
| EP | 1928484 B1 | 11/2008 |
| EP | 2161030 A1 | 3/2010 |
| EP | 2326341 A2 | 6/2011 |
| EP | 2696882 B1 | 3/2015 |
| EP | 2489348 B1 | 11/2016 |
| JP | 2001002589 A | 1/2001 |
| JP | 200189359 A | 4/2001 |
| JP | 2001527537 A | 12/2001 |
| JP | 2002518456 A | 6/2002 |
| JP | 2005500258 A | 1/2005 |
| JP | 2009506071 A | 2/2009 |
| JP | 2009506076 A | 2/2009 |
| JP | 2009073744 A | 4/2009 |
| JP | 2010222329 A | 10/2010 |
| WO | WO1986006959 | 12/1986 |
| WO | WO1991007947 | 6/1991 |
| WO | WO1993015737 | 8/1993 |
| WO | WO1993017037 | 9/1993 |
| WO | WO1994021286 | 9/1994 |
| WO | WO1994023767 | 10/1994 |
| WO | WO1995001185 | 1/1995 |
| WO | 199808976 A1 | 3/1998 |
| WO | WO1998042275 | 10/1998 |
| WO | WO1998043660 | 10/1998 |
| WO | WO1999003491 | 1/1999 |
| WO | WO1999066943 | 12/1999 |
| WO | WO2000033813 | 6/2000 |
| WO | WO2000033814 | 6/2000 |
| WO | WO2001026642 | 4/2001 |
| WO | WO2001041732 | 6/2001 |
| WO | WO2001043775 | 6/2001 |
| WO | WO2002076388 | 10/2002 |
| WO | WO2002082074 | 10/2002 |
| WO | WO2002086105 | 10/2002 |
| WO | WO2002102832 | 12/2002 |
| WO | WO2003072056 | 9/2003 |
| WO | WO2003080022 | 10/2003 |
| WO | WO2003093816 | 11/2003 |
| WO | WO2004019875 | 3/2004 |
| WO | WO2004030524 | 4/2004 |

(56) References Cited

FOREIGN PATENT DOCUMENTS

| WO | WO2004043428 | 5/2004 |
|---|---|---|
| WO | WO2004062563 | 7/2004 |
| WO | WO2005060947 | 7/2004 |
| WO | WO2004093897 | 11/2004 |
| WO | WO2005046636 | 5/2005 |
| WO | WO2005115370 | 12/2005 |
| WO | WO2006020727 | 2/2006 |
| WO | WO2006059105 | 6/2006 |
| WO | WO2006091332 | 8/2006 |
| WO | WO2007025249 | 3/2007 |
| WO | WO2007025286 | 3/2007 |
| WO | WO2008025791 | 3/2008 |
| WO | WO2008134071 | 11/2008 |
| WO | 2008150305 | 12/2008 |
| WO | WO2010030180 | 3/2010 |
| WO | WO2011040597 | 4/2011 |
| WO | WO2011120071 | 10/2011 |
| WO | WO2011153583 | 12/2011 |
| WO | WO2012042371 | 4/2012 |
| WO | WO2012140216 | 10/2012 |
| WO | WO2014057092 | 4/2014 |

OTHER PUBLICATIONS

Mousain-Bosc et al. ("Improvement of neurobehavioral disorders in children supplemented with magnesium—Vitamin B6"; vol. 19(1) Mar. 2006).*
https://www.merriam-webster.com/dictionary/craniofacial, accessed Nov. 29, 21).*
National Institute of Neurological Disorders and Stroke (https://www.ninds.nih.gov/health-information/disorders/williams-syndrome accessed Jul. 29, 2022).*
WebMD (<http://www.webmd.com/children/intellectual-disability-mental-retardation> accessed Jul. 29, 2022).*
Maletinska et al., "The Effect of Divalent Ions on Binding and Signal Transduction in Cells Having Stably Expressed Oxytocin Receptor," Proceedings of the Twenty-Sixth European Peptide Symposium, 925-926 (2001).
Windle et al., "Central Oxytocin Administration Reduces Stress-Induced Corticosterone Release and Anxiety Behavior in Rats," Endocrinology, 138(7):2829-2834 (1997).
Abouleish, "Postpartum Hypertension and Convulsion After Oxytocic Drugs," Anesthesia and Analgesia, 55(6):813-815 (1976).
Agren et al., "Olfactory Cues from an Oxytocin-Injected Male Rat Can Induce Anti-Nociception in its Cagemates," Neuroreport, 8(14):3073-3076 (1997).
Agu et al., "Metabolism and Absorption Enhancement of Methionine Enkephalin in Human Nasal Epithelium," Peptides, 25:563-569 (2004).
Amico et al., "A Time-Dependent Peak of Oxytocin Exists in Cerebrospinal Fluid but Not in Plasma of Humans," Journal of Clinical Endocrinology and Metabolism, 57(5):947-951 (1983).
Arletti et al., "Influence of Oxytocin on Nociception and Morphine Antinociception," Neuropeptides, 24(3):125-129 (1993).
Armstead, "Role of Nociceptin/Orphanin FQ in the Physiologic and Pathologic Control of the Cerebral Circulation," Experimental Biology and Medicine, 227(11):957-968 (2002).
Atke et al., "Uterotonic Activity and Myometrial Receptor Affinity of 1-deamino-1-carba-2-tyrosine(O-methyl)-oxytocin," Acta Endocrinologica, 115(1):155-160 (1987).
Avanti et al., "A New Strategy to Stabilize Oxytocin in Aqueous Solutions: I The Effects of Divalent Metal Ions and Citrate Buffer", The AAPS Journal, 13(2):284-290 (2011).
Bartosz-Bechowski et al., "Novel Nociceptin Analogues," Acta Biochimica Polonica, 48(4):1155-1158 (2001).
Bartsch et al., "The ORL-1 (NOP1) Receptor Ligand Nociceptin/Orphanin FQ (N/OFQ) Inhibits Neurogenic Dural in the Rat", Neuropharmacology, 43:991-998 (2002).

Berzetei-Gurske et al., "Determination of Activity for Nociceptin in the Mouse Vas Deferens", European Journal of Pharmacology, 302:R1-R2 (1996).
Bigoni et al., "Characterization of Nociceptin Receptors in the Periphery: In Vitro and in Vivo Studies," Naunyn Schmiedebergs Archives of Pharmacology, 359(3):160-167 (1999).
Borgland et al., "Nociceptin Inhibits Calcium Channel Currents in a Subpopulation of Small Nociceptive Trigeminal Neurons in Mouse", The Journal of Physiology, 536(1):35-47 (2001).
Born et al., "Sniffing Neuropeptides: A Transnasal Approach to the Human Brain," Nature Neuroscience, 5(6):514-516 (2002).
Brennan et al., "Characterization of a Rat Model of Incisional Pain", Pain, 64:493-501 (1996).
Calo et al., "[Nphe1,Arg14,Lys15]Nociceptin-NH2, A Novel Potent and Selective Antagonist of the Nociceptin/ FQ Receptor," British Journal of Pharmacology, 136(2):303-311 (2002).
Calo et al., "Characterization of [Nphe1]Nociceptin(1-13)NH2, A New Selective Receptor Antagonist," British Journal of Pharmacology, 129(6)1183-1193 (2000).
Calo et al., "Pharmacology of Nociceptin and its Receptor: A Novel Therapeutic Target," British Journal of Pharmacology, 129(7):1261-1283 (2000).
Calvin et al., "A Neurophysiological Theory for the Pain Mechanism of Tic Douloureux," Pain, 3(2):147-154 (1977).
Capsoni et al., "Delivery of NGF to the Brain: Intranasal Versus Ocular Administration in Anti-NGF Transgenic Mice," Journal of Alzheimer's Disease, 16:371-388 (2009).
Carr et al., "Safety and Efficacy of Intranasal Ketamine for the Treatment of Breakthrough Pain in Patients with Chronic Pain: A Randomized, Double-Blind, Placebo-Controlled, Crossover Study," Pain, 108(1-2):17-27 (2004).
Carra et al., "[(pF)Phe4,Arg14,Lys15]N/OFQ-NH2 (UFP-102), A Highly Potent and Selective Agonist of the Nociceptin/Orphanin FQ Receptor", The Journal of Pharmacology and Experimental Therapeutics, 312(3):1114-1123 (2005).
Carvalho et al., "The Nociceptin/Orphanin FQ-NOP Receptor Antagonist Effects on an Animal Model of Sepsis", Intensive Care Medicine, 34:2284-2290 (2008).
Champion et al., "Experimental Biology Symposium on Autonomic and Cardiovascular Regulation: Focus on Nociceptin and Opioid Peptides. Role of Nitric Oxide in Mediating Vasodilator Responses to Opioid Peptides in the Rat", Clinical and Experimental Pharmacology Physiology, 29:229-232 (2002).
Chaplan et al., "Quantitative Assessment of Tactile Allodynia in the Rat Paw," Journal Neuroscience Methods, 53(1):55-63 (1994).
Chevillard et al., "Angiotensin-Converting Enzyme in Discrete Forebrain Areas of Spontaneously Hypertensive Rats," Brain Research, 309:389-392 (1984).
Chiou et al., "Nociceptin/Orphanin FQ Peptide Receptors: Pharmacology and Clinical Implications", Current Drug, 8(1):117-135 (2007).
Chu et al., "Inhibition of Cardiovascular Activity Following Microinjection of Novel Opioid-Like Neuropeptide Nociceptin (Orphanin FQ) into the Rat Rostral Ventrolateral Medulla", Brain Research, 829:134-142 (1999).
Condés-Lara et al., "Actions of Oxytocin and Interactions with Glutamate on Spontaneous and Evoked Dorsal Spinal Cord Neuronal Activities," Brain Research, 976(1):75-81 (2003).
Condés-Lara et al., "Oxytocin Actions on Afferent Evoked Spinal Cord Neuronal Activities in Neuropathic but not in Normal Rats," Brain Research, 1045(1-2):124-133 (2005).
Condés-Lara et al., "Paraventricular Hypothalamic Influences on Spinal Nociceptive Processing," Brain Research, 1081(1):126-137 (2006).
Connor et al., "Nociceptin Receptor Coupling to a Potassium Conductance in Rat Locus Coeruleus Neurones in Vitro", British Journal of Pharmacology, 119:1614-1618 (1996).
Courteix et al., "Evidence for an Exclusive Antinociceptive Effect of Nociceptin/Orphanin FQ, an Endogenous Ligand for the ORLI Receptor, in Two Animal Models of Neuropathic Pain", Pain , 110:236-245 (2004).

(56) References Cited

OTHER PUBLICATIONS

Cox et al., "Opioid Receptors: Introduction", IUPHAR Database, located at <http://www.iuphar-db.org/DATABASE/ last visited on Feb. 24, 2010, Oct. 13, 2009 (4 pages).
Dale et al., "Nasal Administration of Opioids for Pain Management in Adults," Acta Anaesthesiologica Scandinavic,a 46(7):759-770 (2002).
Darland et al., "Orphanin FQ/Nociceptin: A Role in Pain and Analgesia, But So Much More," Trends in Neuroscience, 21(5):215-221 (1998).
De Fraissinette et al., "In vitro Tolerability of Human Nasal Mucosa: Histopathological and Scanning Electron-Microscopic Evaluation of Nasal Forms Containing Sandostatin®," Cell Biology and Toxicology. 11(5):295-301 (1995).
Engstrom et al. "Oxytocin Receptor Binding And Uterotonic Activity of Carbetocin and its Metabolites Following Enzymatic Degradation," European Journal of Pharmacology, 355(2-3):203-10 (1998).
Epperson et al., "Intranasal Oxytocin in Obsessive-Compulsive Disorder," Biological Psychiatry, 40(6):547-549 (1996).
Epperson et al., "Intranasal Oxytocin in Trichotillomania," Biological Psychiatry, 40(6):559-560 (1996).
Ertsey et al., "Plasma Nociceptin Levels are Reduced in Migraine without Aura", Cephalalgia, 25:261-266 (2004).
Fernandez et al., "Nociceptin/Orphanin FQ Increases Anxiety-Related Behavior and Circulating Levels of Corticosterone During Neophobic Tests of Anxiety," Neuropsychopharmacology, 29:59-71 (2004).
Frey, "Bypassing the Blood-Brain Barrier to Deliver Therapeutic Agents to the Brain and Spinal Cord," Drug Delivery Technology 2(5):46-49 (2002).
Fu et al., "Changes in Expression of Nociceptin/Orphanin FQ and its Receptor in Spinal Dorsal Horn Electroacupuncture During Treatment for Peripheral Inflammatory Pain in Rats, " Peptides, 28:1220-1228 (2007).
Gao et al., "Involvement of Opioid Receptors in the Oxytocin-Induced Antinociception in the Central Nervous System of Rats," Regulatory Peptides, 120:53-58 (2004).
Ge et al., "Blockade Effect of mu and kappa Opioid Antagonists on the Anti-Nociception Induced by Intra-Periaqueductal Grey Injection of Oxytocin in Rats," Brain Research, 927(2):204-207 (2002).
Gimpl et al., "The Oxytocin Receptor System: Structure, Function and Regulation," Physiological Reviews, 81(2):629-683 (2001).
Gintzler et al., "Modulation of Enkephalin Release by Nociceptin (Orphanin FQ)," European Journal of Pharmacology, 325:29-34 (1997).
Giuliani et al., "The Inhibitory Effect of Nociceptin on the Micturition Reflex in Anaesthetized Rats", British Journal of Pharmacology, 124:1566-1572 (1998).
Goldstein et al., "Comparison of butorphanol nasal spray and fiorinal with codeine in the treatment of migrane", Headache: The Journal of Head and Face Pain, 38(7):516-522 (1998).
Goodlin, "Is Oxytocin the Culprit?," American Journal of Obstetrics and Gynecology, 153(8):928-929 (1985).
Gozes, "Neuroprotective Peptide Drug Delivery and Development: Potential New Therapeutics," Trends in Neurosciences, 24(12):700-705 (2001).
Gupta et al., "Oxytocin, 'Salting Out,' and Water Intoxication," JAMA, 220(5):681-683 (1972).
Gwak et al., "Analgesic Effects of Intra-Nasal Enkephalins," Journal of Pharmacy and Pharmacology, 55:1207-1212 (2003).
Haldemann et al., "Somatostatin Receptor Scintigraphy in Central Nervous System Tumors: Role of Blood-Brain Barrier Permeability," Journal of Nuclear Medicine, 36(3):403-410 (1995).
Harris, "Water Intoxication Secondary to Oxytocin," Virginia Medical Monthly, 97(6):357-359 (1970).
Hawe et al., "Towards heat-stable oxytocin formulations: analysis of degradation kinetics and identification of degradation products," Pharmaceutical Research, 26:1679-1688 (2009).
Hawkinson et al., "Opioid Activity Profiles Indicate Similarities Between the Nociceptin/Orphanin FQ and Opioid Receptors," European Journal of Pharmacology, 389:107-114 (2000).
Heinrichs et al., "Selective Amnesic Effects of Oxytocin on Human Memory, " Physiology and Behavior, 83(1):31-38 (2004).
Helmchen et al., "Inhibition of Spinal Nociceptive Neurons by Microinjections of Somatostatin into the Nucleus Raphe Magnus and the Midbrain Periaqueductal Gray of the Anesthetized Cat," Neuroscience Letters, 187(2):137-141 (1995).
Hoover, "Intranasal Oxytocin in Eighteen Hundred Patients. A Study on its Safety as Used in a Community Hospital," American Journal of Obstetrics and Gynecology, 110(6):788-794 (1971).
Hou et al., "Nociceptin Immunoreactivity and Receptor mRNA in the Human Trigeminal Ganglion", Brain Research, 964:179-186 (2003).
Hruby et al., "Conformation-Activity Relationships of Opioid Peptides with Selective Activities at Opioid Receptors", Biopolymers (Peptide Science), 51:391-410 (1999).
Hruby et al., "Recent Developments in the Design of Receptor Specific Opioid Peptides," Medicinal Research Reviews, 9(3):343-401 (1989).
Hunter et al., "Identification and Neuropeptide Content of Trigeminal Neurons Innervating the Rat Nasal Epithelium," Neuroscience, 83(2):591-599 (1998).
Illum, "Is Nose-to-Brain Transport of Drugs in Man a Reality?," Journal of Pharmacy and Pharmacology, 56(1):3-17 (2004).
Illum, "Nasal Drug Delivery: New Developments and Strategies," Drug Discovery Today, 7(23):1184-1189 (2002).
Jenck et al., "A Synthetic Agonist at the Orphanin FQ/Nociceptin Receptor ORL1: Anxiolytic Profile in the Rat", PNAS, 97(9):4938-4943 (2000).
Jenck et al., "Orphanin FQ Acts as an Anxiolytic to Attenuate Behavioral Responses to Stress", PNAS, 94:14854-14858 (1997).
Jo et al., "Oxytocin Modulates Glutamatergic Synaptic Transmission Between Cultured Neonatal Spinal Cord Dorsal Horn Neurons," Journal of Neuroscience, 18(7):2377-2386 (1998).
Josey et al., "Oxytocin-Induced Water Intoxication," American Journal of Obstetrics and Gynecology, 104(6):926 (1969).
Kang et al., "Brain Uptake and the Analgesic Effect of Oxytocin—its Usefulness as an Analgesic Agent," Archives of Pharmacal Research, 23(4):391-395 (2000).
Kaplan, "A Generalized Epileptiform Convulsion After Intra-Amniotic Prostaglandin with Intravenous Oxytocin Infusion: A Case Report," South African Medical Journal, 53(1):27-29 (1978).
Kapusta et al., "Cardiovascular and Renal Responses Produced by Central Orphan in FQ/Nociceptin Occur Independent of Renal Nerves", Am Journal Physiology Regulatory Integrative Computer Physiology, 46:987-995 (1999).
Kapusta et al., "Neurohumoral Effects of Orphanin FQ/Nociceptin: Relevance to Cardiovascular and Renal Function", Peptides, 21:1081-1099 (2000).
Khroyan et al., "Activity of New NOP Receptor Ligands in a Rat Peripheral Mononeuropathy Model: Potentiation of Morphine Anti-Allodynic Activity by NOP Receptor Antagonists", European Journal of Pharmacology, 610:49-54 (2009).
Khroyan et al., "Anti-Nociceptive and Anti-Allodynic Effects of a High Affinity NOP Hexapeptide [Ac-RY(3-CI)YRWR-NH2] (Syn 1020) in Rodents", European Journal Pharmacology, 560:29-35 (2007).
Kiran, et al., "Evaluation of a single-dose of intravenous magnesium sulphate for prevention of postoperative pain after inguinal surgery," Indian Journal of Anaesthesia, 55(1):31-35 (2011).
Kirsch et al., "Oxytocin Modulates Neural Circuitry for Social Cognition and Fear in Humans," Journal of Neuroscience, 25(49):11489-11493 (2005).
Knoflach et al., "Modulation of Voltage-Gated Calcium Channels by Orphanin FQ in Freshly Dissociated Hippocampal Neurons", The Journal of Neuroscience, 16(21):6657-6664 (1996).
Ko et al., "Behavioral Effects of a Synthetic Agonist Selective for Nociceptin/Orphanin FQ Peptide Receptors in Monkeys", Neuropsychopharmacology, 34(9):2088-2096 (2009).

(56) References Cited

OTHER PUBLICATIONS

Ko et al., "Quantitative Analysis of Nociceptin in Blood of Patients with Acute and Chronic Pain", NeuroReport, 13(16):1631-1633 (2002).
Kolczewski et al., "Novel Hexahydrospiro[Piperidine-4, 1'-Pyrrolo[3,4-c]Pyrroles]: Highly Selective Small-Molecule Nociceptin/Orphanin FQ Receptor Agonists", Journal of Medicinal Chemistry, 46,(2):255-264 (2003).
Kosfeld et al., "Oxytocin Increases Trust in Humans," Nature, 435:673-676 (2005).
Landgraf, "Plasma Oxytocin Concentrations in Man After Different Routes of Administration of Synthetic Oxytocin," Experimental and Clinical Endocrinology, 85(2):245-248 (1985).
Lazzeri et al., "Daily Intravesical Instillation of 1 mg Nociceptin/Orphanin FQ for the Control of Neurogenic Detrusor Overactivity: A Multicenter Placebo Controlled, Randomized Exploratory Study," The Journal of Urology, 176:2098-2102 (2006).
Lazzeri et al., "Urodynamic and Clinical Evidence of Acute Inhibitory Effects of Intravesical Nociceptin/Orphanin FQ on Detrusor Overactivity in Humans: A Pilot Study," The Journal of Urology, 166:2237-2240 (2001).
Lazzeri et al., "Urodynamic Effects of Intravesical Nociceptin/Orphanin FQ in Neurogenic Detrusor Overactivity: A Randomized, Placebo-Controlled, Double-Blind Study", Urology, 61(5):946-950 (2003).
Lecci et al., "Nociceptin and the Micturition Reflex", Peptides, 21:1007-1021 (2000).
Lee et al., "Diclofenac Inhibition of Sodium Currents in Rat Dorsal Root Ganglion Neurons," Brain Research, 992(1):120-127 (2003).
Lerner, "Enhanced Delivery of Octreotide to the Brain via Transnasal Iontophoretic Administration," Journal of Drug Targeting, 12(5):273-280 (2004).
Loup et al., "Localization of High-Affinity Binding Sites for Oxytocin and Vasopressin in the Human Brain. An Autoradiographic Study," Brain Research, 555(2):220-232 (1991).
Loup et al., "Localization of Oxytocin Binding Sites in the Human Brainstem and Upper Spinal Cord: An Autoradiographic Study," Brain Research, 500(1-2):223-230 (1989).
Lundeberg et al., "Anti-Nociceptive Effects of Oxytocin in Rats and Mice," Neuroscience Letters, 170(1):153-157 (1994).
Madrazo et al., "Intraventricular Somatostatin-14, Arginine Vasopressin, and Oxytocin: Analgesic Effect in a Patient with Intractable Cancer Pain," Applied Neurophysiology, 50(1-6):427-431 (1987).
Mansour et al., "Anatomy of CNS Opioid Receptors", Trends in Neurosciences, 11(7):308-314 (1988).
Mauskop et al., "Intravenous magnesium sulfate rapidly alleviates headaches of various types," Headache, 36(3):154-160 (1996).
McGuire et al., "Brain Activity During Stimulus Independent Thought", NeuroReport, 7(13):2095-2099 (1996).
McKenna et al., "Hyponatremic Fits in Oxytocin-Augmented Labors," International Journal of Gynecology & Obstetrics, 17(3):250-252 (1979).
Mens et al., "Penetration of Neurohypophyseal Hormones from Plasma into Cerebrospinal Fluid (CSF): Half-Times of Disappearance of These Neuropeptides from CSF," Brain Research, 262(1):143-149 (1983).
Meunier et al., "Isolation and Structure of the Endogenous Agonist of Opioid Receptor-Like ORL1 Receptor", Nature, 377:532-535 (1995).
Meunier, "Attenuation of Pain-Related Behaviour in a Rat Model of Trigeminal Neuropathic Pain by Viral-Driven Enkephalin Overproduction in Trigeminal Ganglion Neurons," Molecular Therapy 11(4):608-616 (2005).
Mika et al., Morphine and Endomorphin-1 Differently Influence Pronociceptin/Orphanin FQ System in Neuropathic Pharmacology, Biochemistry Behavior, 78:171-178 (2004).
Millan et al., "Vasopressin and Oxytocin in the Rat Spinal Cord: Analysis of Their Role in the Control of Nociception," Brain Research, 309(2):384-388 (1984).

Mogil et al., "Functional antagonism of mu-, delta- and kappa-opioid antinociception by orphanin FQ," Neuroscience Letter, 214(2-3):131-134 (1996).
Mork et al., "Does Nociceptin Play a Role in Pain Disorders in Man?," Peptides, 23:1581-1587 (2002).
Neal et al., "Localization of Orphanin FQ (Nociceptin) Peptide and Messenger RNA in the Central Nervous System of the Rat", The Journal of Comparative Neurology, 406:503-547 (1999).
Ossipov et al., "The Loss of Antinociceptive Efficacy of Spinal Morphine in Rats with Nerve Ligation Injury is Prevented by Reducing Spinal Afferent Drive", Neuroscience, Letters, 199:87-90 (1995).
Querghi et al., "The effect of adding intrathecal magnesium sulphate to morphine-fentanyl spinal analgesia after thoracic surgery. A prospective, double-blind, placebo-controlled research study," Annales Francaises d'Anesthesie et de Reanimation, 30(1):25-30 (2011).
Ovechkin, "Magnesium Sulfate: Prospects for use in Multimodal Analgesia," Schemes Regional Anesthesia and Treatment of Acute Pain, vol. IV, No. 3, pp. 5-10-D2, Especially pp. 7-8 (English Translation Only) (11 pages).
Ozaki et al., "A Potent and Highly Selective Nonpeptidyl Nociceptin/orphanin FQ Receptor (ORLI) Antagonist: J-113397", European Journal of Pharmacology, 387:17-18 (2000).
Pan et al., "Cloning and Expression of a cDNA Encoding a Mouse Brain Orphanin FQ/nociceptin Precursor," Biochemical Journal, 315:11-13 (1996).
Parker et al., "Intranasal Oxytocin Administration Attenuates the ACTH Stress Response in Monkeys," Psychoneuroendocrinology, 30(9):924-929 (2005).
Pasternak et al., "Minireview: Multiple Mu Opiate Receptors", Life Sciences, 38(21):1889-1898 (1986).
Petersson et al., "Oxytocin Decreases Corticosterone and Nociception and Increases Motor Activity in OVX Rats," Maturitas, 51(4):426-433 (2005).
Petersson et al., "Oxytocin Increases Nociceptive Thresholds in a Long-Term Perspective in Female and Male Rats," Neuroscience Letters, 212(2):87-90 (1986).
Pettit et al., "The development of site-specific drug-delivery systems for protein and peptide biopharmaceuticals," Trends in Biotechnology, 16: 343-349 (1998).
Phillips et al., "Relief of Acute Migraine Headache with Intravenous Oxytocin: Report of Two Cases," Journal of Pain and Palliative Care Pharmacotherapy, 20(3):25-28 (2006).
Pietryka, "Oxytocin & Cholesterol," All Natural Advantage, pp. 1-7 (2016).
Potter, "Water Retention Due to Oxytocin," Obstetrics & Gynecology, 23(5):699-702 (1964).
Raffaeli et al., "Nociceptin Levels in the Cerebrospinal Fluid of Chronic Pain Patients with or without Intrathecal of Morphine," Journal Pain Symptom Management, 32(4):372-377 (2006).
Rash, et al., "Oxytocin and pain: a systematic review and synthesis of findings," Clinical Journal of Pain, 30(5):453-462 (2014).
Reinscheid et al., "Orphanin FQ: A Neuropeptide that Activates an Opioidlike G Protein-Coupled Receptor", Science, 270:792-794 (1995).
Reinscheid et al., "Structure-Activity Relationship Studies on the Novel Neuropeptide Orphanin FQ", The Journal Biological Chemistry, 271(24):14163-14168 (1996).
Reiss et al., "Effects of Nociceptin/Orphanin FQ Receptor (NOP) Agonist, Ro64-6198, on Reactivity to Acute Pain in Mice: Comparison to D Morphine", European Journal of Pharmacology, 579:141-148 (2008).
Reiter et al., Localization of Oxytocin Binding Sites in the Thoracic and Upper Lumbar Spinal Cord of the Adult and Postnatal Rat: A Histoautoradiographic Study, European Journal of Neuroscience, 6(1):98-104 (1994).
Rizzi et al., "[Arg, 14, Lys 15] Nociceptin, a Highly Potent Agonist of the Nociceptin/Orphanin FQ Receptor: in Vitro and in Vivo Studies," The Journal of Pharmacology and Experimental Therapeutics, 3000(1):57-63 (2002).
Rizzi et al., "In Vitro and in Vivo Studies on UFP-112, a Novel Potent and Long Lasting Agonist Selective for the Nociceptin/Orphanin FQ Receptor", Peptides, 28(6):1240-1251 (2007).

(56) References Cited

OTHER PUBLICATIONS

Robbins Headache Clinic, "Combination Therapy for Migraines," located at <http://www.headachedrugs.com/archives2/combination.html> (2004) (2 pages).
Robinson et al., "Oxytocin Mediates Stress-Induced Analgesia in Adult Mice," Journal of Physiology, 540(Pt. 2):593-606 (2002).
Ross et al., "Intranasal Administration of Interferon Beta Bypasses the Blood-Brain Barrier to Target the Central Nervous System and Cervical Lymph Nodes: A Non-Invasive Treatment Strategy for Multiple Sclerosis," Journal of Neuroimmunology, 151:66-77 (2004).
Sayani et al., "Systemic Delivery of Peptides and Proteins Across Absorptive Mucosae," Critical Reviews in Therapeutic Drug Carrier Systems, 13(1&2):85-184 (1996).
Seifer et al., "Water Intoxication and Hyponatremic Encephalopathy from the Use of an Oxytocin Nasal Spray," Journal of Reproductive Medicine, 30(3):225-228 (1985).
Shimohigashi et al., "Sensitivity of Opioid Receptor-Like Receptor ORL 1 for Chemical Modification on Nociceptin, a Naturally Occurring Nociceptive Peptide", The Journal of Biological Chemistry, 271(39):23642-23645 (1996).
Spagnolo et al., "Pharmacological Characterization of the Nociceptin/ Orphanin FQ Receptor Antagonist SB-612111 [(−)-cis-1-Methyi-74[4-2,6-Dichlorophenyl)Piperidin-1-yi]Methyi]-6,7,8,9-Tetrahydro-5H-Benzocyclohepten-5-ol]: in vitro Studies", The Journal of Pharmacology and Experimental Therapeutics, 321(3):961-967 (2007).
Spagnolo, "Activities of mixed NOP and u-opioid receptor ligands", British Journal of Pharmacology, 153:609-619 (2008).
Staszczuk et al., "Methods of Preparation of Magnesium Organic Compounds from Natural Dolomite", Physicochem Problems of Mineral Processing, 37:149-158 (2003).
Stevens et al., "Nociceptin Produces Antinociception After Spinal Administration in Amphibians," Pharmacology, Biochemistry and Behavior, 91:436-440 (2009).
Strassman et al., "Response Properties of Dural Nociceptors in Relation to Headache," Journal of Neurophysiology, 95(3):1298-1306 (2006).
Striebel et al., "Patient-Controlled Intranasal Analgesia: A Method for Noninvasive Postoperative Pain Management," Anesthesia & Analgesia, 83:548-551 (1996).
Szolcsányi et al., "Systemic Anti-Inflammatory Effect Induced by Counter-Irritation Through a Local Release of Somatostatin from Nociceptors," British Journal of Pharmacology, 125(4):916-922 (1998).
Tavani et al., "Role of Peripheral Mu, Delta And Kappa Opioid Receptors in Opioid-Induced Inhibition of Gastrointestinal Transit in Rats", The Journal of Pharmacology and Experimental Therapeutics, 254(1):91-97 (1990).
Thorne, "Delivery of Insulin-Like Growth Factor-I to the Rat Brain and Spinal Cord Along Olfactory and Trigeminal Pathways Following Intranasal Administration," Neuroscience, 127:481-496 (2004).
Tian et al., "Bidirectional Modulatory Effect of Orphanin FQ on Morphine-Induced Analgesia: Antagonism in Brain and in Spinal Cord of the Rat", British Journal of Pharmacology, 120:676-680 (1997).
Tseng, "Recent Advances in the Search for the μ-Opioidergic System: The Antinociceptive Properties of Endomorphin-1 and Endomorphin-2 in the Mouse, " Japanese Journal of Pharmacology, 89:216-220 (2002).
Tzabazis et al., "Differential Activation of Trigeminal C or Aδ Nociceptors by Infrared Diode Laser in Rats: Behavioral Evidence," Brain Research, 1037:148-156 (2005).
Uhl-Bronner et al., "Sexually Dimorphic Expression of Oxytocin Binding Sites in Forebrain and Spinal Cord of the Rat," Neuroscience 135(1):147-154 (2005).
Uryvaev et al., "Extremely Low Doses of Oxytocin Reduce Pain Sensitivity in Men," Bulletin of Experimental Biology and Medicine, 122(5):1071-1073 (1996).

Van Rossum et al., "Neuroanatomical Localization, Pharmacological Characterization and Functions of CGRP, Related Peptides and Their Receptors," Neuroscience & Biobehavioral Reviews, 21(5):649-678 (1997).
Viney, "Nasal Drug Delivery: A Review," Indian Drugs, 38(6):283-287 (2001).
Wang et al., "Antinociceptive Role of Oxytocin in the Nucleus Raphe Magnus of Rats, an Involvement of μ-opioid Receptor," Regulatory Peptides, 115:153-159 (2003).
Wang et al., "Distinct Effect of Intracerebroventricular and Intrathecal Injections of Nociceptin/Orphanin FQ in the Rat Formalin Test," Regulatory Peptides 79:159-163 (1999).
Wang et al., "Parenteral Formulations of Proteins and Peptides: Stability and Stabilizers," Journal of Parent Science and Technology, 42(2S):S4-S26 (1988).
Wang et al., "Review of Excipients and pH's for Parenteral Products Used in the United States," Journal of Parenteral Drug Association, 34(6):452-462 (1980).
Wang et al., "The interaction between the oxytocin and pain modulation in headache patients," Neuropeptides, 47: 93-97 (2013).
Weeke et al., "A Randomized Comparison of Intranasal and Injectable Octreotide Administration in Patients With Acromegaly," The Journal of Clinical Endocrinology and Metabolism, 75(1):163-169 (1992).
Williams et al., "Nociceptin and Urotensin-II Concentrations in Critically III Patients with Sepsis," British Journal of Anaesthesia, 100(6):810-814 (2008).
Windle et al., "Oxytocin Attenuates Stress-Induced c-fos mRNA Expression in Specific Forebrain Regions Associated with Modulation of Hypothalamicuitary-Adrenal Activity," Journal of Neuroscience, 24(12):2974-2982 (2004).
Wiśniewski, "New, Potent, and Selective Peptidic Oxytocin Receptor Agonists", Journal of Medicinal Chemistry, 57:5306-5317 (2014).
Witt, "Regulatory Mechanisms of Oxytocin-Mediated Sociosexual Behavior," Annals of the New York Academy of Sciences, 807:287-301 (1997).
Xie et al., "Hypocretin/Orexin and Nociceptin/Orphanin FQ Coordinately Regulate Analgesia in a Mouse Model of -Induced Analgesia", The Journal of Clinical Investigation, 118(7):2471-2481 (2008).
Xu et al., "Nociceptin or Antinociceptin: Potent Spinal Anti nociceptive Effect of Orphanin FQ/nociceptin in the Rat", NeuroReport, 7(13):2092-2094 (1996).
Xue et al., "Studies and Progress on Orphanin FQ," Foreign Medical Sciences, Section of Pathophysiology and Clinical Medicine, 23(2)158-161 (2003).
Yamada et al., "Pharmacological Profiles of a Novel Opioid Receptor-Likel (ORL1) Receptor Antagonist, JTC-801", Journal Pharmacology, 135:323-332 (2002).
Yamamoto et al., "Effects of Intrathecally Administered Nociceptin, an Opioid Receptor-Like1 (ORL1) Receptor Agonist, on the Thermal Hyperalgesia Induced by Unilateral Constriction Injury to the Sciatic Nerve in the Rat, " Neuroscience Letters, 224:107-110 (1997).
Yang et al., "Modulation by Oxytocin of ATP-Activated Currents in Rat Dorsal Root Ganglion Neurons," Neuropharmacology, 43:910-916 (2002).
Yang, "Intrathecal Administration of Oxytocin Induces Analgesia in Low Back Pain Involving the Endogenous Opiate Peptide System," Spine, 19(8):867-871 (1994).
Yeomans et al., "Nociceptive Responses to High or Low Rates of Noxious Cutaneous Heating are Mediated by Nociceptors in the Rat: Behavioral Evidence," Pain, 68:133-140 (1996).
Yeomans et al., "Therapeutic Effect of Nasal Oxytocin in Chronic Migraine: Dependence on Cytokines," Cephalalgia 33(8 supplement):58-59, P59 Abstract presented at the 2013 International Headache Congress, Boston, M.A, three pages (2013).
Yousef et al., "The effect of adding magnesium sulphate to epidural bupivacaine and fentanyl in elective caesarean section using combined spinal-epidural anaesthesia: a prospective double blind randomized study," International Journal of Obstetric Anesthesia, 19:401-404 (2010).

(56) References Cited

OTHER PUBLICATIONS

Yu et al., "Involvement of Oxytocin in Spinal Antinociception in Rats with Inflammation," Brain Research, 983:13-22 (2003).

Zadina et al., "A Potent and Selective Endogenous Agonist for the μ-Opiate Receptor," Nature, 386:499-502 (1997).

Zaratin et al., "Modification of Nociception and Morphine Tolerance by the Selective Opiate Receptor-Like Orphan Receptor Antagonist (−)-cis-1-Methyl-7-[[4-(2,6-Dichlorophenyi)Piperidin-1-yl] Methyl]-6,7,8,9-Tetrahydro-5 H-Benzocyclohepten-5-ol(SB-612111)", The Journal of Pharmacology and Experimental Therapeutics, 308(2):454-461 (2004).

Zaveri et al., "Small-Molecule Agonists and Antagonists of the Opioid Receptor-Like Receptor (ORL 1, NOP): Ligand-Based Analysis of Structural Factors Influencing Intrinsic Activity at NOP", The AAPS Journal, 7(2):E345-E352 (2005).

Zubrzycka et al., "Inhibition of Trigemino-Hypoglossal Reflex in Rats by Oxytocin in Mediated by μ and κ Opioid Receptors," Brain Research, 1035(1):67-72 (2005).

Liu Qiang, "Development of New Chinese Medicine Products," China Medical Science and Technology Press, p. 428 (2013) (English Translation) (4 pages).

Antoni et al., "Essential role of magnesium in oxytocin-receptor affinity and ligand specificity," Biochemical Journal, 257(2):611-614 (1989).

Yoshida et al., "Evidence that oxytocin exerts anxiolytic effects via oxytocin receptor expressed in serotonergic neurons in mice," Journal of Neuroscience, 29(7):2259-2271 (2009).

Poleszak et al., "Antidepressant- and anxiolytic-like activity of magnesium in mice," Pharmacology, Biochemistry and Behavior, 78 (2004) 7-12.

Guastella et al., "A randomized controlled trial of intranasal oxytocin as an adjunct to exposure therapy for social anxiety disorder," Psychoneuroendocrinology, 34(6):917-923 (2009).

Hallak et al., "Peripheral magnesium sulfate enters the brain and increases the threshold for hippocampal seizures in rats," Journal of Obstetrics & Gynecology, 167(6):1605-1610 (1992).

Khotaku et al., "Henzutsuu no byoutai seiri to sono shinten (Pathologic physiology of migraine and development thereof)" Clinic all-round, 49(6):1767-1770 (2000) (English Translation).

Avanti et al., "A new strategy to stabilize oxytocin in aqueous solutions: II. Suppression of cysteine-mediated intermolecular reactions by a combination of divalent metal ions and citrate", Molecular Pharmaceutics, 9(3):554-562 (2012).

Brown, et al., "Oxytocin Content of the Cerebrospinal Fluid of Dogs and its Relationship to Pain Induced by Spinal Cord Compression," Veterinary Surgery, 27(6):607-611 (1998).

Meziane et al., An Early Postnatal Oxytocin Treatment Prevents Social and Learning Deficits in Adult Mice Deficient for Magel2, a Gene Involved in Prader-Willi Syndrome and Autism, Biological Psychiatry, 78(2):85-94 (2015).

\* cited by examiner

MAGNESIUM-CONTAINING OXYTOCIN FORMULATIONS AND METHODS OF USE

CROSS REFERENCE TO RELATED APPLICATIONS

This application is a national stage application under 35 U.S.C. § 371 of International Application No. PCT/US2017/027265, filed internationally on Apr. 12, 2017, which claims the benefit of priority to U.S. Provisional Patent Application No. 62/321,645, filed Apr. 12, 2016, the disclosures of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 623632001200SEQLIST.TXT, date recorded: Oct. 11, 2018, size: 1 KB).

FIELD OF THE INVENTION

The invention relates to methods and compositions comprising an oxytocin peptide and magnesium ions for the treatment of autism spectrum disorder, related disorders and symptoms of such disorders.

BACKGROUND OF THE INVENTION

Oxytocin is a naturally occurring nine-amino acid neuropeptide that is primarily produced in the paraventricular and supraoptic nuclei of the mammalian hypothalamus. It is released in to the central nervous system via distributed neural pathways and into peripheral circulation via the posterior pituitary. The intramuscular injection or intravenous infusion of synthetic oxytocin (Pitocin®) is currently approved in the United States to produce or improve uterine contractions to facilitate vaginal delivery and to control postpartum hemorrhage. Intranasal oxytocin (Syntocinon®) had been approved in the U.S. for stimulating milk letdown to facilitate breast-feeding from 1960 until 1997. While the nasal spray of Syntocinon® was withdrawn from the United States market at the request of the manufacturer, intranasal oxytocin is still marketed outside of the United States in countries such as Switzerland, Portugal, or Brazil. Use of oxytocin peptides in treatment of autism spectrum disorder has recently been demonstrated. See WO 2004/030524 A2 and WO 2008/042452 A1, the disclosures of which are incorporated herein by reference.

Autism spectrum disorder has become increasingly more prevalent in the human population and is typically recognized by certain behaviors and characteristics, such as impairment in communication skills and/or social interaction, lack of eye contact, and/or an inability to form and/or maintain social relationships. Children and adults diagnosed with autism spectrum disorder can exhibit one or more of the behaviors and characteristics mentioned above to varying degrees. Symptoms often observed in individuals with autism spectrum disorder are persistent deficits in social communication and social interaction, social anxiety, and restricted repetitive behaviors, interests, and activities. Other behaviors and characteristics also observed in persons with autism spectrum disorder include an aversion to physical contact, generalized anxiety, a monotone voice or an inability to modulate volume of voice, failure to develop peer relationships, lack of shared enjoyment and interests and lack of social or emotional reciprocity. Other disorders that display social and communication deficits can include social anxiety disorder, obsessive-compulsive disorder, social (pragmatic) communication disorder, and neurodevelopmental disorders including but not limited to attention deficit hyperactivity disorder, Prader-Willi syndrome, Timothy syndrome, Fragile-X syndrome, Rett syndrome, or Williams syndrome which exhibit symptoms similar to those displayed in autism spectrum disorder. People with autism spectrum disorder tend to have communication deficits, such as responding inappropriately in conversations, misreading nonverbal interactions, or having difficulty building friendships appropriate to their age. In addition, people with autism spectrum disorder may be overly dependent on routines, highly anxious and sensitive to changes in their environment, or intensely focused on inappropriate items (e.g., inanimate objects and/or narrow interests in specific topics). Again, the symptoms of people with autism spectrum disorder vary widely and fall on a continuum, with some individuals showing mild symptoms and others having very severe symptoms. There are no drug therapies available for the core deficits in social communication and social interaction, or restricted repetitive behaviors, interests, and activities in persons with autism spectrum disorder and related disorders, and there remains an urgent need for such treatment.

Oxytocin has been shown to improve the core symptoms of autism, in particular social and communication deficits and associated anxiety symptoms. Human clinical trials have demonstrated efficacy of intranasal oxytocin in treating autism spectrum disorder, related disorders and symptoms of such disorders. See, e.g., Yatawara et al., *Mol. Psychiatry* 2015, 1-9; Gorka et al., *Neuropsychopharmacology* 2015, 40(2):278-286; Anagnostou et al., *Mol. Autism* 2012, 3(1):16; Guastella et al., *Psychoneuroendocrinology* 2009, 34(6):917-923. However, these trials have shown wide variability in the response that people with autism spectrum disorder and related disorders have to treatment with oxytocin. Thus, there exists a need for an oxytocin peptide formulation capable of providing a more pronounced effect in the treatment of autism spectrum disorder and related disorders.

BRIEF SUMMARY OF THE INVENTION

Provided are methods and compositions comprising an oxytocin peptide and magnesium ions for the treatment of an autism spectrum disorder, related disorders and symptoms of such disorders, comprising co-administration of an oxytocin peptide and magnesium ions via craniofacial mucosal administration (e.g., intranasal administration). The methods and magnesium-containing oxytocin peptide formulations described herein provide enhanced efficacy in treating autism spectrum disorder compared to oxytocin alone.

In one aspect, the invention provides a method for treating an autism spectrum disorder, a disorder manifesting one or more symptoms associated with an autism spectrum disorder, social and communication deficits, or anxiety, comprising administering to a subject in need thereof an effective dose of an oxytocin peptide and magnesium ions, wherein co-administration of the oxytocin peptide and the magnesium ions produces a synergistic or enhanced effect. The oxytocin peptide and the magnesium ions may be co-administered concurrently or sequentially. In some embodiments, the oxytocin peptide is administered concurrently with the magnesium ions either in the same unit dose or in separate unit doses or formulations. In some embodiments, the oxytocin peptide and the magnesium ions are administered sequentially. For example, the oxytocin peptide is administered at a time period after administration of the magnesium ions. In some embodiments, the subject is a human.

The oxytocin peptide and the magnesium ions may be administered via the same route or different routes to a subject in need thereof. In some embodiments, the oxytocin peptide is administered via craniofacial mucosal administration (e.g., nasal, buccal, sublingual or ocular administration). In one embodiment, the oxytocin peptide and the magnesium ions are both administered intranasally in the same formulation.

In some aspects, interleukin-6 (IL-6) is used as a biomarker of potential efficacy of administration of the oxytocin peptide in a subject according to a method described herein for the treatment of an autism spectrum disorder, a disorder manifesting one or more symptoms associated with an autism spectrum disorder, social and communication deficits, or anxiety; and to select a subject for application of the methods. In some embodiments, the method comprises measuring the level of IL-6 in a subject and administering to a subject having an elevated IL-6 level an effective dose of an oxytocin peptide and magnesium ions.

In one aspect, the method for treating an autism spectrum disorder, a disorder manifesting one or more symptoms associated with an autism spectrum disorder, social and communication deficits, or anxiety, comprising administering to a subject in need thereof an effective dose of an oxytocin peptide and magnesium ions, wherein co-administration of the oxytocin peptide and the magnesium ions produces a synergistic or enhanced effect, further comprises administering to the subject an effective dose of interleukin-6 (IL-6), wherein administration of IL-6 induces the elevation of oxytocin receptor expression.

In some embodiments, the oxytocin peptide is human oxytocin consisting of Cys-Tyr-Ile-Gln-Asn-Cys-Pro-Leu-Gly (SEQ. ID NO: 1). In some embodiments, the effective dose of the oxytocin peptide is about 0.5 µg to about 2000 µg, preferably about 8 µg to about 1000 µg, more preferably about 15 µg to about 120 µg. In some embodiments, the effective dose of the magnesium ions administered is about 50 µg to about 68 mg, preferably about 50 µg to about 34 mg, more preferably about 1 mg to about 3 mg. In some embodiments, the method comprises administering a magnesium salt (e.g., magnesium citrate and/or magnesium chloride) in an amount to provide about 50 µg to about 68 mg of magnesium, or about 50 µg to about 34 mg of magnesium, or about 1 mg to about 3 mg of magnesium. In some embodiments, the method comprises administering magnesium citrate or magnesium chloride in an amount to provide about 50 µg to about 68 mg of magnesium, or about 50 µg to about 34 mg of magnesium, or about 1 mg to about 3 mg of magnesium. In some embodiments, the effective dose of the oxytocin peptide and the magnesium ions comprises about 0.5 µg to about 2000 µg, or about 15 µg to about 120 µg (e.g., about 60 µg or about 66 µg) of the oxytocin peptide administered in an aqueous solution containing about 0.11% to about 2.8% (preferably about 1.1% to about 1.6%, e.g. about 1.36%) (w/v) magnesium.

In some embodiments, the invention provides a method of reducing one or more symptoms associated with an autism spectrum disorder. The symptoms treatable by the method include any social or communication deficits treatable by an oxytocin peptide, such as deficits in eye contact, social anxiety, generalized anxiety, accuracy in determining complex social cues, empathy, and communication abilities including expressive language functioning.

In some embodiments, the invention provides a method for the treatment of a disorder manifesting one or more symptoms associated with an autism spectrum disorder. In some embodiments, the disorder is social anxiety disorder, obsessive-compulsive disorder, social (pragmatic) communication disorder, and neurodevelopmental disorders including but not limited to attention deficit hyperactivity disorder, Prader-Willi syndrome, Timothy syndrome, Fragile-X syndrome, Rett syndrome, or Williams syndrome, which exhibit symptoms similar to those displayed in autism spectrum disorder.

In one embodiment, the invention provides a method for treating an autism spectrum disorder comprising administering (e.g., intranasally) to a subject in need thereof an effective dose of an oxytocin peptide and magnesium ions, wherein co-administration of the oxytocin peptide and the magnesium ions produces a synergistic or enhanced effect. In one embodiment, the invention provides a method for treating an autism spectrum disorder comprising administering to a subject in need thereof an effective dose of an oxytocin peptide and magnesium ions, wherein the effective dose of the oxytocin peptide and the magnesium ions is administered intranasally in a liquid formulation, and the volume of the liquid formulation administered is between about 5 µL and about 1000 µL.

In one embodiment, the invention provides a method for treating Prader-Willi syndrome comprising administering (e.g., intranasally) to a subject in need thereof an effective dose of an oxytocin peptide and magnesium ions, wherein co-administration of the oxytocin peptide and the magnesium ions produces a synergistic or enhanced effect. In one embodiment, the invention provides a method for treating Prader-Willi syndrome comprising administering to a subject in need thereof an effective dose of an oxytocin peptide and magnesium ions, wherein the effective dose of the oxytocin peptide and the magnesium ions is administered intranasally in a liquid formulation, and the volume of the liquid formulation administered is between about 5 µL and about 1000 µL.

In one embodiment, provided is a method for treating social and communication deficits comprising administering (e.g., intranasally) to a subject in need thereof an effective dose of an oxytocin peptide and magnesium ions, wherein co-administration of the oxytocin peptide and the magnesium ions produces a synergistic or enhanced effect. In one embodiment, the invention provides a method for treating social and communication deficits comprising administering to a subject in need thereof an effective dose of an oxytocin peptide and magnesium ions, wherein the effective dose of the oxytocin peptide and the magnesium ions is administered intranasally in a liquid formulation, and the volume of the liquid formulation administered is between about 5 µL and about 1000 µL.

In one embodiment, provided is a method for treating anxiety comprising administering (e.g., intranasally) to a subject in need thereof an effective dose of an oxytocin peptide and magnesium ions, wherein co-administration of the oxytocin peptide and the magnesium ions produces a synergistic or enhanced effect. In one embodiment, the invention provides a method for treating anxiety comprising administering to a subject in need thereof an effective dose of an oxytocin peptide and magnesium ions, wherein the effective dose of the oxytocin peptide and the magnesium ions is administered intranasally in a liquid formulation, and the volume of the liquid formulation administered is between about 5 μL and about 1000 μL.

In some of these embodiments, the effective dose of the oxytocin peptide is about 0.5 μg to about 2000 μg. In some of these embodiments, the effective dose of the magnesium ions is about 50 μg to about 68 mg. In some of these embodiments, the effective dose of the oxytocin peptide and the magnesium ions comprises about 15 μg to about 120 μg of the oxytocin peptide administered in an aqueous solution containing about 1.1% to about 1.6% (w/v) of magnesium. In some of these embodiments, the effective dose of the oxytocin peptide and the magnesium ions comprises about 66 μg of the oxytocin peptide administered in an aqueous solution containing about 1.36% magnesium. In some of these embodiments, the weight ratio between the dose of the oxytocin peptide administered and the dose of the magnesium ions administered is between about 1:1 to about 1:1000. In some of these embodiments, the molar ratio between the dose of the oxytocin peptide administered and the dose of the magnesium ions administered is between about 1:40 to about 1:40000. In some of these embodiments, the volume of the liquid formulation administered is between about 50 μL and about 200 μL. In some of these embodiments, the liquid formulation is administered using a metered nasal device in 1 to 4 units of about 50 μL per unit (e.g., spray or puff). In some of these embodiments, the oxytocin peptide is human oxytocin (SEQ. ID NO:1).

In some of these embodiments, the liquid formulation is contained in a device for intranasal administration. In some of these embodiments, the device for intranasal administration is a nasal pump apparatus. In some of these embodiments, the nasal pump apparatus comprises a reservoir bottle attached to a pump actuator. In some of these embodiments, the pump actuator is metered to deliver a specified volume of about 50 μL. In some of these embodiments, the nasal pump apparatus comprises a reservoir bottle attached to an aerosolizer. In some of these embodiments, the nasal pump apparatus comprises one of more of the following: (i) a filter for preventing back flow, (ii) a metal-free fluid path, and (iii) a plastic material stable to gamma-radiation.

Further provided is a magnesium-containing oxytocin peptide formulation described herein for use in a method of treating an autism spectrum disorder, a disorder manifesting one or more symptoms associated with an autism spectrum disorder, social and communication deficits, or anxiety, in a subject in need thereof. Also provided is a use of a magnesium-containing oxytocin peptide formulation described herein in the manufacture of a medicament for the treatment of an autism spectrum disorder, a disorder manifesting one or more symptoms associated with an autism spectrum disorder, social and communication deficits, or anxiety.

Also provided is a kit comprising a magnesium-containing oxytocin peptide formulation described herein contained in a device for intranasal administration such as a nasal pump apparatus and suitable packaging. The kit may further comprise instructions for administering the magnesium-containing oxytocin peptide formulation in a subject in need thereof for the treatment of an autism spectrum disorder, a disorder manifesting one or more symptoms associated with an autism spectrum disorder, social and communication deficits, or anxiety.

DETAILED DESCRIPTION OF THE INVENTION

Figure 1:
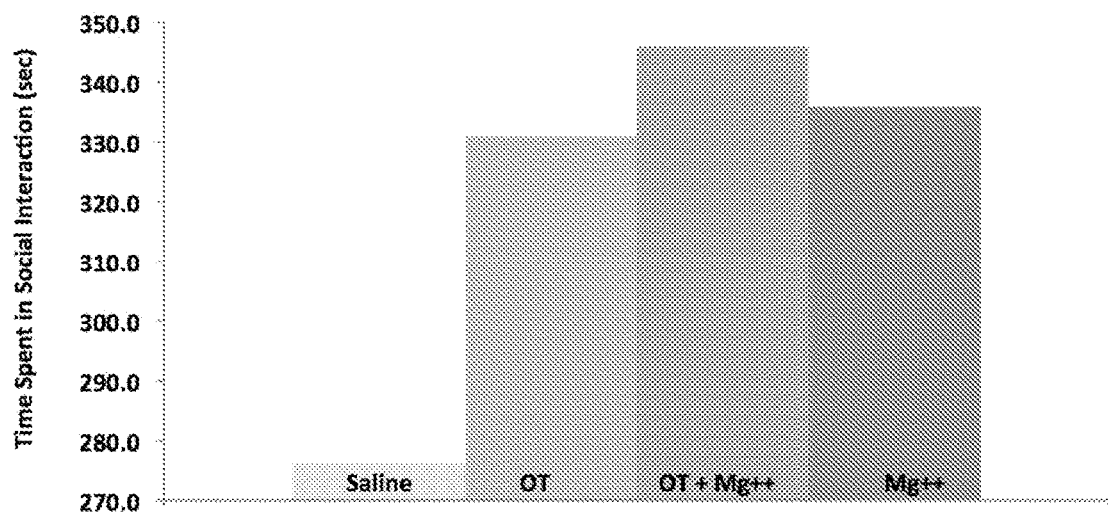
FIG. 1 shows the effect of saline, oxytocin, a combination of magnesium citrate and oxytocin, and magnesium citrate in a rat model of social behavior.

The invention provides, inter alia, a method for treating an autism spectrum disorder, a disorder manifesting one or more symptoms associated with an autism spectrum disorder, social and communication deficits, or anxiety, in a subject in need thereof, by craniofacial administration (e.g., intranasal administration) of an oxytocin peptide and magnesium ions, or a magnesium-containing oxytocin peptide formulation described herein. The oxytocin peptide and the magnesium ions are administered in an effective dose that produces a synergistic or enhanced effect compared to administration of the oxytocin peptide alone.

Definitions

As used herein, "oxytocin peptide" refers to a substance having biological activity associated with natural oxytocin. Oxytocin peptide can be a naturally occurring endogenous peptide, fragments, analogues or derivatives thereof. Oxytocin peptide can also be a non-endogenous peptide, fragments, analogues or derivatives thereof. In one aspect, the oxytocin peptide is human oxytocin. In other aspects, the oxytocin peptide may be an analogue or derivative of human oxytocin.

As used herein, an "analogue" or "derivative" refers to any peptide analogous to naturally occurring oxytocin wherein one or more amino acids within the peptide have been substituted, deleted, or inserted. The term also refers to any peptide wherein one or more amino acids (for example one, two or three amino acids) have been modified, for example by chemical modification. In general, the term covers all peptides which exhibit oxytocin activity but which may, if desired, have a different potency or pharmacological profile.

As used herein, unless otherwise specified, the term "treatment" or "treating" refers to an approach for obtaining a beneficial or desired result, such as a clinical result. For an autism spectrum disorder and related disorders, beneficial or desired clinical results include, but are not limited to, alleviation of a symptom and/or diminishment of the extent of a symptom, for example, social and/or communication deficits and/or repetitive behaviors and/or anxiety. Social and communication deficits can include but are not limited to impairment in communication skills and/or social interaction, lack of eye contact, and/or an inability to form and/or maintain social relationships.

"Synergism", "synergy" or "synergistic effect" refers to a joint action of two or more compounds in such a manner that one supplements or enhances the action of the other to produce an effect greater than that which would be predicted or expected by adding the effects of given doses of two or more compounds if given individually. When two or more agents, used in combination, produces an overall effect (e.g., improvement in social and communication deficits and/or a reduction in anxiety) that is greater than individual effects of any of them in equivalent quantities that would be expected or predicted by summing the effects of the individual agents, it is said that a "synergistic effect" is achieved. When use of two or more agents in combination results in faster onset of effect and/or longer lasting effect than would occur following administration of the individual agents used alone in equivalent quantities, a "synergistic effect" is considered achieved also.

"Craniofacial mucosal administration" refers to delivery to the mucosal surfaces of the nose, nasal passageways, nasal cavity; the mucosal surfaces of the oral cavity including the gingiva (gums), the floor of the oral cavity, the lips, the tongue, the sublingual oral surfaces, including the frenulum of tongue and the floor of the mouth, and the mucosal surfaces of or around the eye including the conjunctiva, the lacrimal gland, the nasolacrimal ducts, and the mucosa of the upper or lower eyelid and the eye.

"Intranasal administration" or "administered intranasally" refers to delivery to the nose, nasal passageways or nasal cavity by spray, drops, powder, gel, film, inhalant or other means.

The "inferior region of the nasal cavity" refers generally to the portion of the nasal cavity where the middle and inferior turbinate bones protrude and is a region of the nasal cavity that is significantly innervated by the trigeminal nerve. The "superior region of the nasal cavity" is defined by the upper third and cribriform plate region wherein olfactory innervation is located.

A "subject" or "patient" as used herein refers to a mammal, including but not limited to a human. Mammals include, but are not limited to, farm animals (such as cows), sport animals, pets (such as guinea pigs, cats, dogs, rabbits and horses), primates, mice and rats. In one embodiment, a subject is a human.

It should be noted that, as used herein, the singular form "a", "an", and "the" includes plural references unless indicated otherwise. Additionally, as used herein, the term "comprising" and its cognates are used in their inclusive sense; that is, equivalent to the term "including" and its corresponding cognates.

Where a range of values is provided, it is intended that each intervening value between the upper and lower limit of that range and any other stated or intervening value in that stated range is encompassed within the disclosure. For example, if a range of 1 µg to 8 µg is stated, it is intended that 2 µg, 3 µg, 4 µg, 5 µg, 6 µg, and 7 µg are also explicitly disclosed, as well as the range of values greater than or equal to 1 µg and the range of values less than or equal to 8 µg. If a range of 10-14% is stated, it is intended that 10%, 11%, 12%, 13%, and 14% are also explicitly disclosed. Furthermore, each smaller range in a stated range between any stated value or intervening value and any other stated or intervening value in that stated range is encompassed within the disclosure. The upper and lower limits of these smaller ranges may independently be included or excluded in the range, and each range where either, neither, or both limits are included in the smaller ranges is also encompassed within the disclosure, subject to any specifically excluded limit in the stated range. Where the stated range includes one or both of the limits, ranges excluding either or both of those included limits are also included in the disclosure.

Oxytocin Peptide

Oxytocin was one of the first peptide hormones to be isolated and sequenced. Natural oxytocin is a nine amino acid cyclic peptide hormone with two cysteine residues that form a disulfide bridge between positions 1 and 6. The amino acid sequence for human oxytocin is Cys-Tyr-Ile-Gln-Asn-Cys-Pro-Leu-Gly (SEQ ID NO: 1).

There are processes described for the production of oxytocin, see for example U.S. Pat. Nos. 2,938,891 and 3,076,797; in addition, oxytocin is commercially available. A variety of peptide analogues and derivatives are available and others can be contemplated for use within the invention and can be produced and tested for biological activity according to known methods. Oxytocin analogues may include, but are not limited to, 4-threonine-1-hydroxy-deaminooxytocin, 4-serine-8-isoleucine-oxytocin, 9-deamidooxytocin, 7-D-proline-oxytocin and its deamino analogue, (2,4-diisoleucine)-oxytocin, deamino oxytocin analogue, 1-deamino-1-monocarba-E12-[Tyr(OMe)]-OT(dCOMOT), 4-threonine-7-glycine-oxytocin (TG-OT), oxypressin, deamino-6-carba-oxytoxin (dC60), L-371,257 and the related series of compounds containing an ortho-trigluoroethoxyphenylacetyl core such as L-374,943. Other exemplary oxytocin analogues include 4-threonine-1-hydroxy-deaminooxytocin, 9-deamidooxytocin, an analogue of oxytocin containing a glycine residue in place of the glycinamide residue, (2,4-diisoleucine)-oxytocin, an analogue of oxytocin with natriuretic and diuretic activities, deamino oxytocin analogue; a long-acting oxytocin analogue, 1-deamino-1-monocarba-E12-[Tyr(OMe)]-OT(dCOMOT), carbetocin, (1-butanoic acid-2-(O-methyl-L-tyrosine)-1-carbaoxytocin, deamino-monocarba-(2-O-methyltyrosine)-oxytocin [d(COMOT)]), [Thr4-Gly7]-oxytocin (TG-OT), oxypressin, Ile-conopressin, deamino-6-carba-oxytoxin (dC60), d[Lys(8)(5/6C-Fluorescein)]VT, d[Thr(4), Lys(8)(5/6C-Fluorescein)]VT, [HO(1)][Lys(8)(5/6C-Fluorescein)]VT, [HO(1)][Thr(4), Lys(8)(5/6CFluorescein)]VT, d[Orn(8)(5/6C-Fluorescein)]VT, d[Thr(4), Orn(8)(5/6C-Fluorescein)]VT, [HO(1)][Orn(8)(5/6C-Fluorescein)]VT, [HO(1)][Thr(4), Orn(8)(5/6C-Fluorescein)]VT, and 1-deamino-oxytocin in which the disulfide bridge between residues 1 or 6 is replaced by a thioether, and desamino-oxytocin analogues in which the disulfide bond is replaced by a diselenide bond, a ditelluride bond, a telluroseleno bond, a tellurosulfide bond or a selenosulfide bond (e.g., the peptide analogues of oxytocin described in PCT patent application WO 2011/120,071, incorporated herein by reference). Peptides for use within the invention can be peptides that are obtainable by partial substitution, addition, or deletion of amino acids within a naturally occurring or native peptide sequence. Peptides can be chemically modified, for example, by amidation of the carboxyl terminus (—NH$_2$), the use of D amino acids in the peptide, incorporation of small non-peptidyl moieties, as well as the modification of the amino acids themselves (e.g. alkylation or esterification of side chain R-groups). Such analogues, derivatives and fragments should substantially retain the desired biological activity of the native oxytocin peptide. In some embodiments, the oxytocin analogue is 4-serine-8-isoleucine-oxytocin or 9-deamidooxytocin. In some embodiments, the oxytocin analogue is carbetocin. The present disclosure also embrace other known oxytocin analogs, for example, the peptidic oxytocin receptor agonists described in PCT patent application WO 2012/042371 and Wisniewski, et al. *J. Med. Chem.* 2014, 57:5306-5317, the entire content of which is incorporated herein by reference. In some embodiments, the oxytocin analogue is a compound selected from Compound Nos. 1-65 described in Tables 1-3 in Wisniewski, et al. *J. Med. Chem.* 2014, 57:5306-5317. In some embodiments, the oxytocin analogue is a selected from the group consisting of Compound No. 31 ([2-ThiMeGly7]dOT), Compound No. 47 (carba-6-[Phe2,BuGly7]dOT), Compound No. 55 (carba-6-[3-MeBzlGly7]dOT) and Compound No. 57 (carba-1-[4-FBzlGly7]dOT, also referred to as merotocin).

In some embodiments, oxytocin or an oxytocin analogue is isotopically labeled by having one or more atoms replaced by an isotope having a different atomic mass. Examples of isotopes that may be incorporated into the disclosed compounds include isotopes of hydrogen (e.g., $^2$H and $^3$H), carbon (e.g., $^{13}$C and $^{14}$C), nitrogen (e.g., $^{15}$N), oxygen (e.g., $^{18}$O and $^{17}$O), phosphorus (e.g., $^{31}$P and $^{32}$P), fluorine (e.g., $^{15}$F), chlorine (e.g., $^{36}$Cl) and sulfur (e.g. $^{35}$S). The isotopically labeled compound may be administered to a subject or other subject and subsequently detected, yielding useful diagnostic and/or therapeutic management data, according to conventional techniques. Further, the isotopically labeled compound may be administered to a subject or other subject in need thereof, yielding therapeutically advantageous absorption, distribution, metabolism and/or elimination profiles. All isotopic variations of the oxytocin peptide, e.g. human oxytocin or an analogue or derivative thereof, whether radioactive or not, are contemplated.

In some embodiments, the oxytocin peptide is human oxytocin consisting of Cys-Tyr-Ile-Gln-Asn-Cys-Pro-Leu-Gly (SEQ. ID NO: 1).

An "international unit" (IU, UI or IE) is an internationally accepted unit of activity used to quantify vitamins, hormones and vaccines. It defines the amount of a substance that gives a unit of activity as determined using a defined biological assay in order to standardize preparations from multiple source materials. Similarly, a USP unit is a defined dosage unit established by the United States Pharmacopeia in cooperation with the Food and Drug Administration in order to ensure the identity, strength, quality, purity and consistency of a drug product. In general, USP units are equal to International Units, due to harmonization efforts. By convention, for oxytocin, 1 unit of activity is generally defined as equal to approximately 2 micrograms of synthetic oxytocin peptide; or 1 mg is equal to 500 units (Stedman's Medical Dictionary). Therefore, as used herein, one "IU" or "International Unit" of an oxytocin peptide is the amount of the oxytocin peptide that has the same biological activity or produces the same level of a biological effect (e.g. contractile response of rat uterine strips) as approximately 2 micrograms of the synthetic peptide. An analogue with weaker activity would require more material to achieve the same level of biological effect. Determinations of drug potency are well known to those skilled in the art and may include either in vitro or in vivo assays using synthetic oxytocin as a reference. Atke and Vilhardt *Acta Endocrinol.* 1987: 115(1):155-60; Engstrom et al. *Eur. J. Pharmacol.* 1998: 355(2-3):203-10.

Magnesium-Containing Oxytocin Peptide Formulations

In the method of the present invention for the treatment an autism spectrum disorder, a disorder manifesting one or more symptoms associated with an autism spectrum disorder, social and communication deficits, or anxiety, comprising administering to a subject in need thereof in an effective dose of an oxytocin peptide and magnesium ions, the oxytocin peptide and the magnesium ions may be administered in a magnesium-containing oxytocin peptide formulation or composition. In one aspect, the magnesium-containing oxytocin peptide formulation or composition comprises the oxytocin peptide and the magnesium ions in an amount that produces a synergistic or enhanced effect when used in the treatment of an autism spectrum disorder, a disorder manifesting one or more symptoms associated with an autism spectrum disorder, social and communication deficits, or anxiety.

The relative proportion of the oxytocin peptide and the magnesium ions in the magnesium-containing oxytocin peptide formulation is important in achieving optimal synergistic or enhanced effect. The optimal amounts of the oxytocin peptide and the magnesium ions may depend on the specific disorder or symptoms, the type of synergistic or enhanced effect desired, and other factors such as the route of administration. For example, the amount of magnesium may be important to achieve a faster onset of effect; the amount of oxytocin may be important to achieve a longer-lasting effect and the relative ratio between oxytocin and magnesium may be important to achieve maximum improvement in social functioning, reduction of social and communication deficits, and/or decrease in anxiety.

In some embodiments, the magnesium-containing oxytocin peptide formulation or composition is a liquid formulation comprising between about 0.01 mg/mL and about 16 mg/mL of the oxytocin peptide. In some embodiments, the amount of the oxytocin peptide in the liquid formulation is greater than about (lower limit) 0.01, 0.05, 0.1, 0.2, 0.3, 0.4, 0.5, 1 or 2 mg/mL. In some embodiments, the amount of the oxytocin peptide in the liquid formulation is less than about (upper limit) 16, 12, 10, 8, 6, 4, 2, 1.6, 1.2, 1, 0.8, 0.6, 0.4, 0.3, 0.2 or 0.1 mg/mL. That is, the amount of the oxytocin peptide in the liquid formulation is anywhere in the range of from about 0.01 to 16 mg/mL in which the lower limit is less than the upper limit. In some embodiments, the magnesium-containing oxytocin peptide formulation or composition comprises between about 0.01 mg/mL and about 12 mg/mL, between about 0.05 mg/mL and about 16 mg/mL, between about 0.1 mg/mL and about 12 mg/mL, between about 0.1 mg/mL and about 8 mg/mL, between about 0.1 mg/mL and about 4 mg/mL, between about 0.1 mg/mL and about 2 mg/mL, between about 0.1 mg/mL and about 1.6 mg/mL, between about 0.1 mg/mL and about 1.2 mg/mL, between about 0.1 mg/mL and about 1 mg/mL, between about 0.1 mg/mL and about 0.8 mg/mL, between about 0.1 mg/mL and about 0.4 mg/mL, between about 0.1 mg/mL and about 0.3 mg/mL, between about 0.2 mg/mL and about 16 mg/mL, between about 0.2 mg/mL and about 12 mg/mL, between about 0.2 mg/mL and about 10 mg/mL, between about 0.2 mg/mL and about 8 mg/mL, between about 0.2 mg/mL and about 6 mg/mL, between about 0.2 mg/mL and about 4 mg/mL, between about 0.2 mg/mL and about 2 mg/mL, between about 0.2 mg/mL and about 1.6 mg/mL, between about 0.2 mg/mL and about 1.2 mg/mL, between about 0.2 mg/mL and about 1 mg/mL, between about 0.2 mg/mL and about 0.8 mg/mL, between about 0.2 mg/mL and about 0.6 mg/mL, between about 0.2 mg/mL and about 0.4 mg/mL, between about 0.2 mg/mL and about 0.3 mg/mL, between about 0.3 mg/mL and about 16 mg/mL, between about 0.3 mg/mL and about 12 mg/mL, between about 0.3 mg/mL and about 10 mg/mL, between about 0.3 mg/mL and about 8 mg/mL, between about 0.3 mg/mL and about 4 mg/mL, between about 0.3 mg/mL and about 3 mg/mL, between about 0.3 mg/mL and about 1 mg/mL, between about 0.3 mg/mL and about 0.5 mg/mL, between about 0.5 mg/mL and about 16 mg/mL, between about 0.5 mg/mL and about 10 mg/mL, between about 0.5 mg/mL and about 5 mg/mL, between about 0.5 mg/mL and about 1 mg/mL, between about 1 mg/mL and about 16 mg/mL, between about 1 mg/mL and about 10 mg/mL, or between about 1 mg/mL and about 5 mg/mL of the oxytocin peptide. In a preferred embodiment, the magnesium-containing oxytocin peptide formulation or composition comprises between about 0.1 mg/mL and about 2 mg/mL, between about 0.15 mg/mL and about 1.5 mg/mL, or between about 0.2 mg/mL and about 1.2 mg/mL of the oxytocin peptide. In one embodiment, the oxytocin peptide is human oxytocin consisting of Cys-Tyr-Ile-Gln-Asn-Cys-Pro-Leu-Gly (SEQ. ID NO: 1).

In some embodiments, the magnesium-containing oxytocin peptide formulation or composition is a liquid formulation comprising between about 5 IU/mL and about 8000 IU/mL of the oxytocin peptide. In some embodiments, the amount of the oxytocin peptide in the liquid formulation is greater than about (lower limit) 5, 25, 50, 75, 100, 150, 200, 250, 500, 750 or 1000 IU/mL. In some embodiments, the amount of the oxytocin peptide in the liquid formulation is less than about (upper limit) 8000, 6000, 5000, 4000, 3000, 2000, 1000, 800, 600, 500, 400, 300, 200, 150, 100 or 50 IU/mL. That is, the amount of the oxytocin peptide in the liquid formulation is anywhere in the range of from about 5 to 8000 IU/mL in which the lower limit is less than the upper limit. In some embodiments, the magnesium-containing oxytocin peptide formulation or composition comprises between about 500 IU/mL and about 6000 IU/mL, between about 25 IU/mL and about 8000 IU/mL, between about 50 IU/mL and about 6000 IU/mL, between about 50 IU/mL and about 4000 IU/mL, between about 50 IU/mL and about 2000 IU/mL, between about 50 IU/mL and about 1000 IU/mL, between about 50 IU/mL and about 800 IU/mL, between about 50 IU/mL and about 600 IU/mL, between about 50 IU/mL and about 500 IU/mL, between about 50 IU/mL and about 400 IU/mL, between about 50 IU/mL and about 200 IU/mL, between about 50 IU/mL and about 150 IU/mL, between about 100 IU/mL and about 8000 IU/mL, between about 100 IU/mL and about 6000 IU/mL, between about 100 IU/mL and about 5000 IU/mL, between about 100 IU/mL and about 4000 IU/mL, between about 100 IU/mL and about 3000 IU/mL, between about 100 IU/mL and about 2000 IU/mL, between about 100 IU/mL and about 1000 IU/mL, between about 100 IU/mL and about 800 IU/mL, between about 100 IU/mL and about 600 IU/mL, between about 100 IU/mL and about 500 IU/mL, between about 100 IU/mL and about 400 IU/mL, between about 100 IU/mL and about 300 IU/mL, between about 100 IU/mL and about 200 IU/mL, between about 100 IU/mL and about 150 IU/mL, between about 150 IU/mL and about 8000 IU/mL, between about 150 IU/mL and about 6000 IU/mL, between about 150 IU/mL and about 5000 IU/mL, between about 150 II/mL and about 4000 IU/mL, between about 150 IU/mL and about 2000 IU/mL, between about 150 IU/mL and about 1500 IU/mL, between about 150 IU/mL and about 500 IU/mL, between about 150 IU/mL and about 250 IU/mL, between about 250 IU/mL and about 8000 IU/mL, between about 250 IU/mL and about 5000 IU/mL, between about 250 IU/mL and about 2500 IU/mL, between about 250 IU/mL and about 500 IU/mL, between about 500 IU/mL and about 8000 IU/mL, between about 500 IU/mL and about 5000 IU/mL, or between about 500 IU/mL and about 2500 IU/mL of the oxytocin peptide. In a preferred embodiment, the magnesium-containing oxytocin peptide formulation or composition comprises between about 50 IU/mL and about 1000 IU/mL, between about 75 IU/mL and about 750 IU/mL, or between about 100 IU/mL and about 600 IU/mL of the oxytocin peptide. In one embodiment, the oxytocin peptide is human oxytocin consisting of Cys-Tyr-Ile-Gln-Asn-Cys-Pro-Leu-Gly (SEQ. ID NO:1).

The amount of magnesium present in the formulation may also be expressed in percentage by weight (w/v) (grams of magnesium or $Mg^{2+}$ per 100 mL of solution), in mg/mL (milligrams of magnesium or $Mg^{2+}$ per milliliter of solution), or in molarity ("M"-defined as moles of magnesium or $Mg^{2+}$ per liter of the solution, or "mM"—defined as millimoles of magnesium or $Mg^{2+}$ per liter of the solution).

In some embodiments, the magnesium-containing oxytocin peptide formulation or composition is a liquid formulation comprising between about 1 mg/mL and about 30 mg/mL of magnesium or magnesium ions ($Mg^{2+}$). In some embodiments, the composition comprises between about 11 mg/mL and about 15 mg/mL of magnesium or magnesium ions. In some embodiments, the amount of the magnesium or magnesium ions in the liquid formulation is greater than about (lower limit) 1, 2, 3, 4, 5, 6, 7, 8, 9, 10, 11 or 12 mg/mL. In some embodiments, the amount of the magnesium or magnesium ions in the liquid formulation is less than about (upper limit) 30, 25, 20, 15, 14, 13, 12, 11, 10, 9, 8, 7, 6 or 5 mg/mL. That is, the amount of magnesium or magnesium ions in the liquid formulation is anywhere in the range of from about 1 to 30 mg/mL in which the lower limit is less than the upper limit. In some embodiments, the magnesium-containing oxytocin peptide formulation or composition is a liquid formulation comprising between about 0.01 mg/mL and about 16 mg/mL (preferably between about 0.1 mg/mL and about 2 mg/mL, more preferably between about 0.15 mg/mL and about 1.5 mg/mL, or about 0.33 mg/mL) of the oxytocin peptide and between about 1 mg/mL and about 30 mg/mL (or between about 3 mg/mL and about 30 mg/mL, between about 4 mg/mL and about 30 mg/mL, between about 5 mg/mL and about 30 mg/mL, between about 8 mg/mL and about 30 mg/mL, between about 10 mg/mL and about 30 mg/mL, preferably between about 11 mg/mL and about 15 mg/mL, or about 13 mg/mL, or about 12 mg/mL) of magnesium or $Mg^{2+}$. In some embodiments, the magnesium-containing oxytocin peptide formulation or composition is a liquid formulation comprising between about 50 mM and about 1500 mM of magnesium or magnesium ions ($Mg^{2+}$). In some embodiments, the amount of the magnesium or magnesium ions in the liquid formulation is greater than about (lower limit) 50, 100, 150, 200, 250, 300, 350, 400, 450, 500, 550 or 600 mM. In some embodiments, the amount of the magnesium or magnesium ions in the liquid formulation is less than about (upper limit) 1500, 1200, 1000, 750, 700, 650, 600, 550, 500, 450, 400, 350, 300 or 250 mM. That is, the amount of magnesium or magnesium ions in the liquid formulation is anywhere in the range of from about 50 to 1500 mM in which the lower limit is less than the upper limit. In some embodiments, the magnesium-containing oxytocin peptide formulation or composition is a liquid formulation comprising between about 5 IU/mL and about 8000 IU/mL (preferably between about 50 IU/mL and about 1000 IU/mL, more preferably between about 75 IU/mL and about 750 IU/mL, or about 150 IU/mL) of the oxytocin peptide and between about 1 mg/mL and about 30 mg/mL (preferably between about 11 mg/mL and about 15 mg/mL, or about 13 mg/mL, or about 12 mg/mL) of magnesium or $Mg^{2+}$. In some embodiments, the magnesium-containing oxytocin peptide formulation or composition is a liquid formulation comprising between about 5 IU/mL and about 8000 IU/mL (preferably between about 50 IU/mL and about 1000 IU/mL, more preferably between about 75 IU/mL and about 750 IU/mL, or about 150 IU/mL) of the oxytocin peptide and between about 50 mM and about 1200 mM (or between about 100 mM and about 1200 mM, between about 150 mM and about 1200 mM, between about 200 mM and about 1200 mM, between about 300 mM and about 1200 mM, between about 400 mM and about 1200 mM, preferably between about 400 mM and about 600 mM, or about 500 mM) of magnesium or $Mg^{2+}$.

Any magnesium salt (such as a water-soluble magnesium salt) may be used to provide the magnesium ions in the magnesium-containing oxytocin peptide formulation. The magnesium salt used in the magnesium-containing oxytocin peptide formulation may be selected based on a number of factors such as the amount of free magnesium ions that can be delivered when the formulation is administered, the solubility of the magnesium salt in the media for a liquid formulation, the acidity/basicity of the counter ion, and/or the dissociation constant of the salt. For example, in a liquid formulation, the magnesium salt needs to be sufficiently soluble in the liquid media to deliver the magnesium ions in concentration required for producing synergistic or enhanced effect with the oxytocin peptide. Other factors may also be considered when selecting the magnesium salt, such as compatibility with other substances in the formulation and ability of the counter ion to perform other functions in the formulation. For example, magnesium citrate is sufficiently soluble in an aqueous solution to provide the desirable amount of magnesium or desirable magnesium ion concentration; citrate salts are pharmaceutically acceptable; the citrate can be part of the buffering agents; and magnesium citrate may add a pleasant flavor for the formulation. The magnesium ions in the magnesium-containing oxytocin peptide formulation may be provided by using one or more magnesium salts. A magnesium salt in the magnesium-containing oxytocin peptide formulation may be a magnesium salt used initially in preparing of the magnesium-containing oxytocin peptide formulation, or formed in situ during preparation of the magnesium-containing oxytocin peptide formulation. For example, magnesium chloride may be used initially in preparing the formulation; and upon addition of citric acid to the formulation, magnesium citrate may be formed in situ. In such instance, the magnesium ions in the magnesium-containing oxytocin peptide formulation are provided by both magnesium chloride and magnesium citrate.

In some embodiments, the magnesium-containing oxytocin peptide formulation or composition comprises one or more magnesium salts selected from the group consisting of magnesium citrate, magnesium chloride, magnesium sulfate, magnesium acetate, magnesium lactate, magnesium stearate, magnesium oxide, magnesium carbonate, magnesium glycinate, magnesium maltate, magnesium taurate, magnesium gluconate, magnesium succinate, and magnesium pyrophosphate. In some embodiments, the magnesium-containing oxytocin peptide formulation or composition is a liquid formulation comprising a magnesium salt (e.g., magnesium citrate or magnesium chloride) in an amount to provide between about 1 mg/mL and about 30 mg/mL of magnesium. In some embodiments, the composition comprises a magnesium salt in an amount to provide between about 1 mg/mL and about 30 mg/mL of magnesium ions ($Mg^{2+}$). In some embodiments, the magnesium-containing oxytocin peptide formulation or composition is a liquid formulation comprising one or more magnesium salts (e.g., magnesium citrate and/or magnesium chloride) in an amount to provide between about 1 mg/mL and about 30 mg/mL of magnesium or magnesium ions ($Mg^{2+}$). In some embodiments, the composition comprises one or more magnesium salts in an amount to provide between about 11 mg/mL and about 15 mg/mL of magnesium or magnesium ions. In some embodiments, the magnesium-containing oxytocin peptide formulation or composition is a liquid formulation comprising between about 0.01 mg/mL and about 16 mg/mL (preferably between about 0.1 mg/mL and about 2 mg/mL, more preferably between about 0.15 mg/mL and about 1.5 mg/mL, or about 0.33 mg/mL) of the oxytocin peptide and a magnesium salt (e.g., magnesium citrate or magnesium chloride) in an amount to provide between about 1 mg/mL and about 30 mg/mL (or between about 3 mg/mL and about 30 mg/mL, between about 4 mg/mL and about 30 mg/mL, between about 5 mg/mL and about 30 mg/mL, between about 8 mg/mL and about 30 mg/mL, between about 10 mg/mL and about 30 mg/mL, preferably between about 11 mg/mL and about 15 mg/mL, or about 13 mg/mL, or about 12 mg/mL) of magnesium or $Mg^{2+}$. In some embodiments, the magnesium-containing oxytocin peptide formulation or composition is a liquid formulation comprising between about 5 IU/mL and about 8000 IU/mL (preferably between about 50 IU/mL and about 1000 IU/mL, more preferably between about 75 IU/mL and about 750 IU/mL, or about 150 IU/mL) of the oxytocin peptide and one or more magnesium salts (e.g., magnesium citrate and/or magnesium chloride) in an amount to provide between about 1 mg/mL and about 30 mg/mL (preferably between about 11 mg/mL and about 15 mg/mL, or about 13 mg/mL, or about 12 mg/mL) of magnesium or $Mg^{2+}$. In some embodiments, the magnesium-containing oxytocin peptide formulation or composition is a liquid formulation comprising between about 5 IU/mL and about 8000 IU/mL (preferably between about 50 IU/mL and about 1000 IU/mL, more preferably between about 75 IU/mL and about 750 IU/mL, or about 150 IU/mL) of the oxytocin peptide and one or more magnesium salts (e.g., magnesium citrate and/or magnesium chloride) in an amount to provide between about 50 mM and about 1200 mM (or between about 100 mM and about 1200 mM, between about 150 mM and about 1200 mM, between about 200 mM and about 1200 mM, between about 300 mM and about 1200 mM, between about 400 mM and about 1200 mM, preferably between about 400 mM and about 600 mM, or about 500 mM) of magnesium or $Mg^2$.

The relative amount of the oxytocin peptide and the magnesium ions in the magnesium-containing oxytocin peptide formulation or composition detailed herein may be defined by a weight ratio or a molar ratio. The weight ratio between the amount of the oxytocin peptide and the amount of magnesium or magnesium ions in the formulation or composition is referred to as the "OT/Mg (w) ratio". For example, in a magnesium-containing oxytocin peptide formulation or composition having an OT/Mg (w) ratio of about 1:40, for each 1 mg of the oxytocin peptide present in the formulation or composition, the magnesium or magnesium ions present in the formulation or composition is about 40 mg. The molar ratio between the amount of the oxytocin peptide and the amount of magnesium or magnesium ions in the formulation or composition is referred to as the "OT/Mg (m) ratio". For example, in a magnesium-containing oxytocin peptide formulation or composition having an OT/Mg (m) ratio of about 1:1600, for each 1 μmol of the oxytocin peptide present in the formulation or composition, the magnesium or magnesium ions present in the formulation or composition is about 1600 μmol.

In some embodiments, the magnesium-containing oxytocin peptide formulation or composition has an OT/Mg (w) ratio between about 1:1 and about 1:1000. In some embodiments, the OT/Mg (w) ratio in the formulation or composition is less than about (upper limit) 1:1, 1:2, 1:5, 1:10, 1:20, 1:30, 1:40, 1:45, 1:50, 1:60, 1:80, 1:100 or 1:200. In some embodiments, the OT/Mg (w) ratio in the formulation or composition is greater than about (lower limit) 1:1000, 1:800, 1:500, 1:250, 1:200, 1:150, 1:100, 1:80, 1:60, 1:50, 1:40, 1:30, 1:20, 1:10 or 1:5. That is, the OT/Mg (w) ratio in the formulation or composition is anywhere in the range of from about 1:1 to 1:1000 in which the upper limit is more than the lower limit. In some embodiments, the formulation or composition has an OT/Mg (w) ratio between about 1:2 and about 1:200. In some preferred embodiments, the formulation or composition has an OT/Mg (w) ratio of about 1:30, about 1:35, about 1:40, about 1:45, or about 1:50. In some embodiments, the formulation or composition has an OT/Mg (w) ratio between about 1:2 and about 1:1000, between about 1:2 and about 1:800, between about 1:2 and about 1:500, between about 1:2 and about 1:250, between about 1:2 and about 1:150, between about 1:2 and about 1:100, between about 1:2 and about 1:80, between about 1:2 and about 1:60, between about 1:2 and about 1:50, between about 1:2 and about 1:40, between about 1:2 and about 1:30, between about 1:2 and about 1:20, between about 1:2 and about 1:10, between about 1:2 and about 1:5, between about 1:5 and about 1:1000, between about 1:5 and about 1:800, between about 1:5 and about 1:500, between about 1:5 and about 1:200, between about 1:5 and about 1:100, between about 1:5 and about 1:80, between about 1:5 and about 1:60, between about 1:5 and about 1:50, between about 1:5 and about 1:40, between about 1:5 and about 1:30, between about 1:5 and about 1:20, between about 1:5 and about 1:10, between about 1:10 and about 1:1000, between about 1:10 and about 1:800, between about 1:10 and about 1:500, between about 1:10 and about 1:200, between about 1:10 and about 1:100, between about 1:10 and about 1:80, between about 1:10 and about 1:60, between about 1:10 and about 1:50, between about 1:10 and about 1:40, between about 1:10 and about 1:30, between about 1:10 and about 1:20, between about 1:20 and about 1:1000, between about 1:20 and about 1:800, between about 1:20 and about 1:500, between about 1:20 and about 1:200, between about 1:20 and about 1:100, between about 1:20 and about 1:80, between about 1:20 and about 1:70, between about 1:20 and about 1:60, between about 1:20 and about 1:50, between about 1:20 and about 1:40, between about 1:20 and about 1:30, between about 1:30 and about 1:1000, between about 1:30 and about 1:800, between about 1:30 and about 1:500, between about 1:30 and about 1:200, between about 1:30 and about 1:100, between about 1:30 and about 1:80, between about 1:30 and about 1:70, between about 1:30 and about 1:60, between about 1:30 and about 1:50, between about 1:30 and about 1:40, between about 1:35 and about 1:45, between about 1:40 and about 1:1000, between about 1:40 and about 1:800, between about 1:40 and about 1:500, between about 1:40 and about 1:200, between about 1:40 and about 1:100, between about 1:40 and about 1:80, between about 1:40 and about 1:70, between about 1:40 and about 1:60, between about 1:40 and about 1:50, between about 1:50 and about 1:1000, between about 1:50 and about 1:800, between about 1:50 and about 1:500, between about 1:50 and about 1:200, between about 1:50 and about 1:100, between about 1:50 and about 1:90, between about 1:50 and about 1:80, between about 1:50 and about 1:70, between about 1:50 and about 1:60, between about 1:60 and about 1:1000, between about 1:60 and about 1:800, between about 1:60 and about 1:500, between about 1:60 and about 1:200, between about 1:60 and about 1:100, between about 1:60 and about 1:90, between about 1:60 and about 1:80, between about 1:60 and about 1:70, between about 1:80 and about 1:1000, between about 1:80 and about 1:800, between about 1:80 and about 1:500, between about 1:80 and about 1:200, between about 1:80 and about 1:100, between about 1:100 and about 1:1000, between about 1:100 and about 1:800, between about 1:100 and about 1:500, between about 1:100 and about 1:200, between about 1:200 and about 1:1000, between about 1:200 and about 1:800, between about 1:200 and about 1:500, or between about 1:500 and about 1:1000.

In one embodiment, the oxytocin peptide is human oxytocin consisting of Cys-Tyr-Ile-Gln-Asn-Cys-Pro-Leu-Gly (SEQ. ID NO:1).

In some embodiments, the magnesium-containing oxytocin peptide formulation or composition has an OT/Mg (m) ratio between about 1:40 and about 1:40,000. In some embodiments, the OT/Mg molar ratio in the formulation or composition is less than about (upper limit) 1:40, 1:80, 1:100, 1:150, 1:175, 1:200, 1:250, 1:280, 1:300, 1:400, 1:500, 1:560, 1:800, 1:1000, 1:1100, 1:1200, 1:1600, 1:1700, 1:1800, 1:2000, 1:2400, 1:3200, 1:4000 or 1:8000. In some embodiments, the OT/Mg molar ratio in the formulation or composition is greater than about (lower limit) 1:40000, 1:30000, 1:20000, 1:10000, 1:7500, 1:5000, 1:4000, 1:3000, 1:2500, 1:2000, 1:1600, 1:1200, 1:1100, 1:1000, 1:800, 1:600, 1:400 or 1:200. That is, the OT/Mg (w) ratio in the formulation or composition is anywhere in the range of from about 1:40 to 1:40000 in which the upper limit is more than the lower limit. In some embodiments, the formulation or composition has an OT/Mg (m) ratio between about 1:80 and about 1:8000. In some preferred embodiments, the formulation or composition has an OT/Mg (m) ratio of about 1:175, about 1:280, about 1:560, about 1:1100, about 1:1200, about 1:1400, about 1:1600, about 1:1700, about 1:1800, or about 1:2000. In some embodiments, the formulation or composition has an OT/Mg (m) ratio between about 1:80 and about 1:40000, between about 1:80 and about 1:30000, between about 1:80 and about 1:20000, between about 1:80 and about 1:10000, between about 1:80 and about 1:7500, between about 1:80 and about 1:5000, between about 1:80 and about 1:3000, between about 1:80 and about 1:2000, between about 1:80 and about 1:1600, between about 1:80 and about 1:1200, between about 1:80 and about 1:800, between about 1:80 and about 1:400, between about 1:80 and about 1:200, between about 1:175 and about 1:40000, between about 1:175 and about 1:30000, between about 1:175 and about 1:20000, between about 1:175 and about 1:10000, between about 1:175 and about 1:5000, between about 1:175 and about 1:3000, between about 1:175 and about 1:2400, between about 1:175 and about 1:2000, between about 1:175 and about 1:1700, between about 1:175 and about 1:1600, between about 1:175 and about 1:1200, between about 1:175 and about 1:1100, between about 1:175 and about 1:800, between about 1:175 and about 1:560, between about 1:175 and about 1:400, between about 1:175 and about 1:280, between about 1:200 and about 1:40000, between about 1:200 and about 1:30000, between about 1:200 and about 1:20000, between about 1:200 and about 1:10000, between about 1:200 and about 1:5000, between about 1:200 and about 1:3000, between about 1:200 and about 1:2400, between about 1:200 and about 1:2000, between about 1:200 and about 1:1600, between about 1:200 and about 1:1200, between about 1:200 and about 1:800, between about 1:200 and about 1:400, between about 1:280 and about 1:40000, between about 1:280 and about 1:30000, between about 1:280 and about 1:20000, between about 1:280 and about 1:10000, between about 1:280 and about 1:5000, between about 1:280 and about 1:3000, between about 1:280 and about 1:2400, between about 1:280 and about 1:2000, between about 1:280 and about 1:1700, between about 1:280 and about 1:1600, between about 1:280 and about 1:1200, between about 1:280 and about 1:1100, between about 1:280 and about 1:800, between about 1:280 and about 1:560, between about 1:280 and about 1:400, between about 1:400 and about 1:40000, between about 1:400 and about 1:30000, between about 1:400 and about 1:20000, between about 1:400 and about 1:8000, between about 1:400 and about 1:4000, between about 1:400 and about 1:3000, between about 1:400 and about 1:2400, between about 1:400 and about 1:2000, between about 1:400 and about 1:1600, between about 1:400 and about 1:1200, between about 1:400 and about 1:800, between about 1:560 and about 1:40000, between about 1:560 and about 1:30000, between about 1:560 and about 1:20000, between about 1:560 and about 1:8000, between about 1:560 and about 1:4000, between about 1:560 and about 1:3000, between about 1:560 and about 1:2400, between about 1:560 and about 1:2000, between about 1:560 and about 1:1700, between about 1:560 and about 1:1600, between about 1:560 and about 1:1200, between about 1:560 and about 1:1100, between about 1:560 and about 1:800, between about 1:800 and about 1:40000, between about 1:800 and about 1:30000, between about 1:800 and about 1:20000, between about 1:800 and about 1:10000, between about 1:800 and about 1:5000, between about 1:800 and about 1:3000, between about 1:800 and about 1:2400, between about 1:800 and about 1:2000, between about 1:800 and about 1:1600, between about 1:800 and about 1:1200, between about 1:1100 and about 1:40000, between about 1:1100 and about 1:30000, between about 1:1100 and about 1:20000, between about 1:1100 and about 1:10000, between about 1:1100 and about 1:5000, between about 1:1100 and about 1:4000, between about 1:1100 and about 1:3000, between about 1:1100 and about 1:2400, between about 1:1100 and about 1:2000, between about 1:1100 and about 1:1700, between about 1:1100 and about 1:1600, between about 1:1200 and about 1:40000, between about 1:1200 and about 1:30000, between about 1:1200 and about 1:20000, between about 1:1200 and about 1:10000, between about 1:1200 and about 1:5000, between about 1:1200 and about 1:4000, between about 1:1200 and about 1:3000, between about 1:1200 and about 1:2400, between about 1:1200 and about 1:2000, between about 1:1200 and about 1:1600, between about 1:1400 and about 1:1800, between about 1:1600 and about 1:40000, between about 1:1600 and about 1:30000, between about 1:1600 and about 1:20000, between about 1:1600 and about 1:10000, between about 1:1600 and about 1:5000, between about 1:1600 and about 1:3000, between about 1:1600 and about 1:2400, between about 1:1600 and about 1:2000, between about 1:1700 and about 1:40000, between about 1:1700 and about 1:30000, between about 1:1700 and about 1:20000, between about 1:1700 and about 1:10000, between about 1:1700 and about 1:5000, between about 1:1700 and about 1:3000, between about 1:1700 and about 1:2400, between about 1:1700 and about 1:2000, between about 1:2000 and about 1:40000, between about 1:2000 and about 1:30000, between about 1:2000 and about 1:20000, between about 1:2000 and about 1:10000, between about 1:2000 and about 1:5000, between about 1:2000 and about 1:4000, between about 1:2000 and about 1:3000, between about 1:2000 and about 1:2400, between about 1:2400 and about 1:40000, between about 1:2400 and about 1:30000, between about 1:2400 and about 1:20000, between about 1:2400 and about 1:10000, between about 1:2400 and about 1:5000, between about 1:2400 and about 1:4000, between about 1:2400 and about 1:3000, between about 1:3000 and about 1:40000, between about 1:3000 and about 1:30000, between about 1:3000 and about 1:20000, between about 1:3000 and about 1:10000, between about 1:3000 and about 1:4000, between about 1:4000 and about 1:40000, between about 1:4000 and about 1:30000, between about 1:4000 and about 1:20000, between about 1:4000 and about 1:10000, between about 1:8000 and about 1:40000, between about 1:8000 and about 1:30000, between about 1:8000 and about 1:20000, or between about 1:10000 and about 1:40000. In one embodiment, the oxytocin peptide is human oxytocin consisting of Cys-Tyr-Ile-Gln-Asn-Cys-Pro-Leu-Gly (SEQ. ID NO:1).

In some embodiments, the magnesium-containing oxytocin peptide formulation or composition comprising an oxytocin peptide and magnesium ions further comprises one or more pharmaceutically acceptable carriers (thus constituting a pharmaceutical composition) and optionally other ingredients, such as excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. Exemplary excipients include solubilizers, surfactants and chelators. For example, formulations may include, methyl-β-cyclodextrin (Me-β-CD), edetate disodium, arginine, sorbitol, NaCl, methylparaben sodium (MP), propylparaben sodium (PP), chlorobutanol (CB), benzyl alcohol, zinc chloride, ethyl alcohol, didecanoyl L-α-phosphatidylcholine (DDPC), polysorbate, lactose, citrate, tartrate, acetate, and/or phosphate.

Liquid carriers include, but are not limited to, water, saline, aqueous dextrose, and glycols particularly (when isotonic) for solutions. The carrier can also be selected from various oils, including those of petroleum, animal, vegetable or synthetic origin (e.g. peanut oil, olive oil, soybean oil, mineral oil, sesame oil, and the like). Suitable pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical processes, such as sterilization, and can contain conventional pharmaceutical additives, such as preservatives, stabilizing agents, reducing agents, anti-oxidants, chelating agents, wetting agents, emulsifying agents, dispersing agents, jelling agents, salts for adjusting osmotic pressure, buffers, and the like. A liquid carrier may be hypotonic or isotonic with body fluids and may have a pH within the range of 3.5-8.5. The use of additives in the preparation of peptide and/or protein-based compositions, particularly pharmaceutical compositions, is well-known in the art. In some embodiments, the composition has a pH of about 2 to about 7. In some embodiments, the composition has a pH of about 4 to about 7. In a preferred embodiment, the pH of the formulation/composition is about 4.5.

In some embodiments, the magnesium-containing oxytocin peptide formulation or composition may further comprise one or more mucosal delivery-enhancing agents selected from (A)-(K): (A) solubilization agents; (B) charge modifying agents, (C) pH control agents; (D) degradative enzyme inhibitors; (E) mucolytic or mucus clearing agents; (F) ciliostatic agents; (G) membrane penetration-enhancing agents; (H) modulatory agents of epithelial junction physiology, such as nitric oxide (NO) stimulators, chitosan, and chitosan derivatives; (I) vasodilator agents; (J) selective transport-enhancing agents; and (K) stabilizing delivery vehicles, carriers, supports or complex-forming species with which the oxytocin peptide is effectively combined, associated, contained, encapsulated or bound to stabilize the active agent for enhanced mucosal delivery. Membrane penetration-enhancing agents in Group (G) may be (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule, (viii) a small hydrophobic penetration enhancer; (ix) sodium or a salicylic acid derivative; (x) a glycerol ester of acetoacetic acid, (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis. (xviii) an inhibitor of cholesterol synthesis; or (xiv) any combination of the membrane penetration enhancing agents of (i)-(xviii). In various embodiments of the invention, an oxytocin peptide may be combined with one, two, three, four or more of the mucosal delivery-enhancing agents recited in (A)-(K). These mucosal delivery-enhancing agents may be admixed, alone or together, with the oxytocin peptide, or otherwise combined therewith in a pharmaceutically acceptable formulation or delivery vehicle. The magnesium-containing oxytocin peptide formulation or composition described herein may provide increased bioavailability of the oxytocin peptide following delivery thereof to a mucosal surface (e.g., in the nasal cavities) of a mammalian subject.

The lists of carriers and additives discussed herein are by no means complete and a worker skilled in the art can choose carriers and excipients from the GRAS (generally regarded as safe) list of chemicals allowed in pharmaceutical preparations and those that are currently allowed by the U.S. Food and Drug Administration in topical and parenteral formulations, and those that become allowed in the future. (See also Wang et al., (1980) *J. Parent. Drug Assn.*, 34:452-462; Wang et al., (1988) *J. Parent. Sci. and Tech.*, 42:S4-S26.)

In some embodiments, the magnesium-containing oxytocin peptide formulation or composition, comprising an oxytocin peptide and magnesium ions, wherein the oxytocin peptide and the magnesium ions are in an amount that produces a synergistic or enhanced effect when used in the treatment of an autism spectrum disorder, further comprises one or more solvent or excipient selected from the group consisting of chlorobutanol, benzalkonium, methyl 4-hydroxybenzoate, propyl 4-hydroxybenzoate, acetic acid, citric acid, glycerol, sodium chloride, sodium monohydrogen phosphate, sorbitol and water. In some embodiments, the magnesium-containing oxytocin peptide formulation or composition further comprises chlorobutanol, acetic acid and water.

In some embodiments, the magnesium-containing oxytocin peptide formulation or composition, comprising an oxytocin peptide and magnesium ions, further comprises a chitosan-containing excipient (e.g., ChiSys®, http://www.archimedespharma.com/productArchiDevChiSys-.html). In some embodiments, the magnesium-containing oxytocin peptide formulation or composition further comprises about 1% of the chitosan-containing excipient. In some embodiments, a chitosan glutamate salt may be preferred for nasal delivery for its superior absorption enhancing ability. In some embodiments, chitosan co-polymer nanoparticles may be used, such as nanoparticles containing chitosan glutamate and a negatively charged polymer (e.g., tripolyphosphate pentasodium). Thiolated chitosans (e.g. chitosan covalently modified with 2-iminothiolane), which have been used in microparticles containing insulin and reduced glutathione, may also be useful as an excipient in the magnesium-containing oxytocin peptide formulation or composition described herein.

In some embodiments, the magnesium-containing oxytocin peptide formulation or composition, comprising an oxytocin peptide and magnesium ions, further comprises one or more gelling agents, such that the oxytocin peptide formulation forms a gel in the nasal cavity, thus enhancing nasal absorption of the oxytocin peptide. Gelling systems useful in the formulations and methods described herein may include any known gelling system, such as a chemically reactive pectin-based gelling system (e.g., PecSys™, Archimedes Pharma) and a thermoreactive polymer gelling system (e.g., Pluronic® F127, BASF). PecSys™ is a low viscosity aqueous pectin based solution, delivered as a fine mist in which each droplet gels on contact with calcium ions in the nasal mucosa. Other low methoxy pectin could also be employed, e.g., at about 1% concentration. Pluronic® F127 contains ethylene oxide/propylene oxide block copolymers. The gelling temperatures vary depending on the ratios of components and the amount of co-polymer employed in the final formulation. Gelling in the human nasal cavity has been demonstrated for Pluronic® F127 at approximately 18-20% wt/vol, for examples, as used in a vitamin B12 gel supplement (EnerB, Nature's Bounty, NY) and in a gelling sumatriptan, which contains 18% wt/vol Pluronic® F127 and 0.3% wt/vol Carbopol (anionic bioadhesive polymer C934P). The monomer ratios and concentrations may be adjusted for the intended oxytocin formulations to ensure gelling at 25-37° C., around the typical temperature of 34° C. in nasal cavity. If the gelation temperature is lower than 25° C., the formulation could gel at room temperature; if the gelation temperature is above 37° C., the formulation would not fully gel on contact with the nasal mucosa. In some embodiments, the magnesium-containing oxytocin peptide formulation or composition may further comprise a mucoadhesive agent such as Carbopol. Addition of a mucoadhesive, e.g., addition of up to 0.5% Carbopol, may further lower the gelation temperature.

In some embodiments, the magnesium-containing oxytocin peptide formulation or composition, comprising an oxytocin peptide and magnesium ions, further comprises a surface active agent, such as a nonionic surfactant (e.g., polysorbate-80), and one or more buffers, stabilizers, or tonicifiers. In some embodiments, the magnesium-containing oxytocin peptide formulation or composition further comprises a propellant. The pH of the nasal spray solution is optionally between about pH 3.0 and 8.5, but when desired the pH is adjusted to optimize delivery of a charged macromolecular species (e.g., a therapeutic protein or peptide) in a substantially unionized state. The pharmaceutical solvents employed can also be a slightly acidic aqueous buffer (pH 3-6). Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, benzalkonium chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid (EDTA), and the like. Suitable gases include, but are not limited to, nitrogen, helium, chlorofluorocarbons (CFCs), hydrofluorocarbons (HFCs), carbon dioxide, air, and the like. Suitable stabilizers and tonicifying agents include sugars and other polyols, amino acids, and organic and inorganic salts. In some embodiments, the magnesium-containing oxytocin peptide formulation or composition further comprises a citrate salt, a succinate salt or a pyrophosphate salt.

In some embodiments, the magnesium-containing oxytocin peptide formulation or composition, comprising an oxytocin peptide and magnesium ions, further comprises an agent capable of upregulating oxytocin receptor expression, such as IL-6.

To further enhance the mucosal delivery of the oxytocin peptide, an enzyme inhibitor, particularly proteases inhibitors, can be included further in the formulation. Protease inhibitors may include, but are not limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-NH$_2$, DAPT, diprotin A and B, ebelactone A and B, foroxymithine, leupeptin, phosphoramidon, aprotinin, puromycin, BBI, soybean trypsin inhibitor, phenylmethylsulfonyl fluoride, E-64, chymostatin, 1,10-phenanthroline, EDTA and EGTA. Other enzyme inhibitors such as bacitracin may also be included in the formulation.

To enhance delivery into or across a mucosal surface and/or absorption of the oxytocin peptide and the magnesium ions, an absorption-enhancing agent can be included in the formulation. These enhancing agents may enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery) of the composition. Enhancement of mucosal delivery can thus occur by any of a variety of mechanisms, for example by increasing the diffusion, transport, persistence or stability of the oxytocin peptide, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

Mucosal absorption enhancing compounds may include, but are not limited to, surfactants, bile salts, dihydrofusidates, bioadhesive/mucoadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

All peptides described and/or contemplated herein can be prepared by chemical synthesis using either automated or manual solid phase synthetic technologies, generally known in the art. The peptides can also be prepared using molecular recombinant techniques known in the art.

Delivery Systems

The magnesium-containing oxytocin peptide formulation or composition may be adapted for craniofacial mucosal administration (e.g., nasal, buccal, sublingual or ocular administration). In some embodiments, the composition may further comprise a device for mucosal delivery. In some embodiments, the composition is adapted for buccal and/or sublingual mucosal delivery, which may further comprise a device for buccal and/or sublingual mucosal administration, such as unit dose containers, pump sprays, droppers, squeeze bottles, airless and preservative-free sprays, nebulizers, dose inhalers and pressurized dose inhalers. In some embodiments, the composition is adapted for ocular delivery, which may further comprise a device for conjunctival administration, such as a dropper or a squeeze bottle. In some embodiments, the composition is adapted for intranasal administration, which may further comprise a device for intranasal administration, such as a dropper, pump spray, squeeze bottle, airless and preservative-free sprays, or a nasal pump apparatus, e.g., a nasal pump apparatus comprising a reservoir bottle attached to an aerosolizer.

Intranasal drug delivery has been a topic of research and development for many years, although it has been only within the past decade that carrier systems have been devised which make delivery of substances effective. (Sayani and Chien, *Critical Reviews in Therapeutic Drug Carrier Systems* 1996, 13:85-184.) Intranasal delivery has a number of advantageous features including comparatively high bioavailability, rapid kinetics of absorption and avoidance of a first-pass effect in the liver. In some aspects, intranasal administration can allow for delivery of an oxytocin peptide to the nasal cavity and in other aspects, intranasal administration can allow for targeted delivery to the cranial nerves of the nose and/or the brain. Without wishing to be bound by any particular theories, intranasal administration of an oxytocin peptide can target either the olfactory nerve systems or the trigeminal nerve systems or both. The oxytocin peptide may be delivered intranasally in any applicable forms, including but is not limited to a liquid formulation, a solid formulation (e.g., a dry powder formulation), a gel formulation or an emulsion formulation.

In embodiments where the combination of oxytocin and magnesium ions are administered intranasally, the composition can be prepared as a liquid aerosol formulation combined with a dispersing agent and/or a physiologically acceptable diluent. Alternatively, dry powder aerosol formulations are contemplated, and may contain a finely divided solid form of the subject compound and a dispersing agent allowing for the ready dispersal of the dry powder particles. With either liquid or dry powder aerosol formulations, the formulation is aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter for nasal (in a range of from about 10 microns) or pulmonary (in a range of from about 2-5 microns) distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

In some embodiments, the magnesium-containing oxytocin peptide formulation or composition useful in the methods described herein, wherein the oxytocin peptide and the magnesium ions are in an amount that produces a synergistic or enhanced effect when used in the treatment of autism spectrum disorder, are administered using a device for intranasal delivery. The device may be any device suitable for intranasal administration of the magnesium-containing oxytocin peptide formulation. In some embodiments, the device is suitable for delivery of the oxytocin peptide and the magnesium ions to specific region within the nasal cavity. In some embodiments, the device is suitable for delivery of the oxytocin peptide and the magnesium ions to the inferior two-thirds of the nasal cavity. In some embodiments, the device is suitable for delivery of the oxytocin peptide and the magnesium ions to the upper third of the nasal cavity. In some embodiments, the device is suitable for delivery of the oxytocin peptide to the entire nasal passage.

In some embodiments, the device for intranasal delivery is a nasal pump apparatus. In some embodiments, the nasal pump apparatus comprises a reservoir bottle attached to a pump actuator. In some embodiments, the pump actuator is metered to deliver a specified volume (e.g. about 5 to about 1000 µL, preferably about 50 to about 150 µL, more preferably about 50 µL or about 100 µL) in a specified distribution of droplet sizes. In some embodiments, the nasal pump apparatus comprises a reservoir bottle attached to an aerosolizer, e.g. an Equadel pump marketed by Aptar Pharma. In some embodiments, the device for nasal administration functions irrespective of the pressure applied to the pump once a threshold value is reached. In some embodiments, the device for nasal administration is a mucosal atomization device (e.g., LMA® MAD NASAL™) that can be added to a syringe. For administration in large mammals, the nasal pump apparatus may comprise a reservoir bottle attached to a pump actuator that is metered to deliver larger volumes (e.g., about 100 µL to about 600 µL, or higher).

In some embodiments, the device for intranasal delivery is designed for delivery of multiple doses of the drug formulations. For example, a nasal pump apparatus may comprise a reservoir bottle attached to a pump actuator where the reservoir bottle holds multiple dose of the liquid formulation and the pump actuator is metered to deliver a specified volume that is a fraction of the liquid formulation held in the reservoir bottle. In some embodiments, the pump actuator is metered to deliver about 50 µL of the liquid formulation per spray. The nasal pump apparatus may comprise a filter for preventing back flow in order to reduce contaminant (e.g., bacterial) ingress into the reservoir bottle. In some embodiments, the nasal pump apparatus comprises a metal-free path for delivery of the liquid formulation (e.g., a plastic path). In some embodiments, the pump apparatus uses plastic material that is stable to gamma radiation (used for sterilizing the nasal apparatus). In some embodiments, the device for intranasal delivery is equipped with a multi-dose pump comprising a microbial filter and an auto-blocking mechanism in the pump actuator, for example, a spray device described in U.S. Pat. No. 5,988,449.

In some embodiments, the device for intranasal delivery is a breath-actuated nasal delivery device, such as the devices described in U.S. Pat. Nos. 7,784,460 and 7,854,227. Such devices may improve delivery to a target site deep into the nasal cavity. In some embodiments, a standard metered dose spray device is incorporated into a housing that allows the patient to blow into a mouthpiece to actuate the device. In some embodiments, the device is comprised of a conical sealing nosepiece and a mouthpiece that incorporate a traditional mechanical spray pump (e.g. an Equadel pump marketed by Aptar Pharma), a chargeable spring and a breath actuation mechanism. The system can be used for single or multi-dose delivery. One example of such a liquid delivery device is the OptiMist™ device marketed by Opti-Nose. When in use, the nasal piece of the device is inserted into the nostril and the mouth piece is blown into. This closes the soft palate, transfers pressure to the nostril, opens passages providing airflow behind the nasal septum and allows air to exit the other nostril (bidirectional flow). Since the device is breath actuated, small particles cannot enter the lungs. Modifications to flow rate and particle size allows for targeting of specific nasal regions.

In some embodiments, the device for intranasal delivery is a unit-dose metering spray device suited for single administration of the magnesium-containing oxytocin peptide formulation or composition. In some embodiments, the device for intranasal delivery is a multi-dose metering spray pump apparatus suited for repeated administrations of an oxytocin peptide.

Drop size, plume volume and flow rate can be modified to target specific nasal regions. The liquid spray may provide droplet size between 5 and 50 microns in order to target olfactory and/or respiratory epithelium. Larger droplets primarily travel down the nasopharynx and are swallowed, while smaller droplets are targeted to the pulmonary tissue. The Mass Median Equivalent Aerodynamic Diameter (MMAD) is used to specify the drop size. The pH of the nasal spray is optimized to deliver charged peptide in mostly an unionized state. The nose will generally tolerate solutions having a pH of about 3-8. The nasal mucosa can generally absorb volumes of approximately 100 µL before saturation occurs and liquid begins to drip out of the nose. Therefore, plume volume may be up to (and including) 100 µL. For use in large mammals, plume volume may be up to (and including) 150 µL or higher (e.g., 600 µL or higher). For infant and pediatric use, or for veterinary use in smaller animals (e.g., rodents, cats), smaller plume volumes (5-50 µL) could be used.

In some embodiments, the device for intranasal delivery is an ergonomically designed to facilitate patient compliance, such as a pump apparatus with a side-actuation triggering mechanism. In some embodiments, the device for intranasal delivery comprises a metering spray pump working as a closed system, which does not allow air to enter into the pump apparatus thus preventing contamination from airborne germs. In some embodiment, the device for intranasal delivery comprises a metering spray pump working with a filter. The venting air is sucked through a filter assembled inside the pump, keeping airborne germs out of the pump apparatus. In some embodiments, the intranasal delivery device comprising a nasal pump apparatus may further comprise micro-electronic devices that may facilitate data transmission and treatment monitoring.

In some embodiments, the magnesium-containing oxytocin peptide formulation or composition comprises an oxytocin peptide and magnesium ions wherein the oxytocin peptide and the magnesium ions are contained in any one of the devices for intranasal delivery described herein, and wherein the concentrations of the oxytocin peptide and the magnesium ions are within any of the concentration ranges described herein, as if each and every combination of device and concentration is described individually.

Methods

The terms "autism spectrum disorder (ASD)" or "autism" refer to a group of complex disorders of brain development. These disorders are characterized, in varying degrees, by difficulties in social interaction, verbal and nonverbal communication and repetitive behaviors. With the May 2013 publication of the fifth edition of the Diagnostic and Statistical Manual of Mental Disorders (DSM-5), all autism disorders were merged into one umbrella diagnosis of ASD. Previously, they were recognized as distinct subtypes, including autistic disorder, childhood disintegrative disorder, pervasive developmental disorder-not otherwise specified (PDD-NOS) and Asperger syndrome. See http://www.autismspeaks.org/what-autism. Those skilled in the art will recognize that there is considerable overlap of the symptoms of autism spectrum disorder with many other psychiatric disorders. Examples of disorders which exhibit symptoms similar to those displayed in autism spectrum disorder include, but are not limited to, social anxiety disorder, obsessive-compulsive disorder, social (pragmatic) communication disorder, and neurodevelopmental disorders including but not limited to attention deficit hyperactivity disorder, Prader-Willi syndrome, Timothy syndrome, Fragile-X syndrome, Rett syndrome, and Williams syndrome.

The DSM-5 provides diagnostic criteria for ASD including: (A) Persistent deficits in social communication and social interaction across multiple contexts, as manifested, currently or by history, by the following illustrative examples: (1) Deficits in social-emotional reciprocity, ranging, for example, from abnormal social approach and failure of normal back-and-forth conversation; to reduced sharing of interests, emotions, or affect; to failure to initiate or respond to social interactions; (2) Deficits in nonverbal communicative behaviors used for social interaction, ranging, for example, from poorly integrated verbal and nonverbal communication; to abnormalities in eye contact and body language or deficits in understanding and use of gestures; to a total lack of facial expressions and nonverbal communication; and (3) Deficits in developing, maintaining, and understanding relationships, ranging, for example, from difficulties adjusting behavior to suit various social contexts; to difficulties in sharing imaginative play or in making friends; to absence of interest in peers; and (B) Restricted, repetitive patterns of behavior, interests, or activities, as manifested, currently or by history, by at least two of the following illustrative examples: (1) Stereotyped or repetitive motor movements, use of objects, or speech (e.g., simple motor stereotypies, lining up toys or flipping objects, echolalia, idiosyncratic phrases); (2) Insistence on sameness, inflexible adherence to routines, or ritualized patterns or verbal nonverbal behavior (e.g., extreme distress at small changes, difficulties with transitions, rigid thinking patterns, greeting rituals, need to take same route or eat food every day); (3) Highly restricted, fixated interests that are abnormal in intensity or focus (e.g., strong attachment to or preoccupation with unusual objects, excessively circumscribed or perseverative interest); and (4) Hyper- or hyporeactivity to sensory input or unusual interests in sensory aspects of the environment (e.g., apparent indifference to pain/temperature, adverse response to specific sounds or textures, excessive smelling or touching of objects, visual fascination with lights or movement). See http://www.autismspeaks.org/what-autism/diagnosis/dsm-5-diagnostic-criteria.

Autism spectrum disorders (ASD) are characterized by social-interaction difficulties, communication challenges and a tendency to engage in repetitive behaviors. However, symptoms and their severity vary widely across these three core areas. ASD can be associated with intellectual disability, difficulties in motor coordination and attention and physical health issues such as sleep and gastrointestinal disturbances. ASD can be associated with psychiatric symptoms including anxiety and depression. See, e.g., Kim et al., *Autism* 2000, 4(2):117-132.

Oxytocin has been known to treat a number of conditions including anxiety and social and communication deficits in autism spectrum disorders. However, it has been observed that the effect of oxytocin in treating social and communication deficits in autism spectrum disorder varies widely between patients. It is possible that variations in receptor availability and receptor affinity for oxytocin are responsible for the variation in effect. Clinical efforts in using commercial formulations of oxytocin (e.g., Syntocinon®) to treat ASD have been marred by lack of efficacy and poor tolerability. Due to the low potency and high volume of currently available oxytocin formulations, when administered by nasal spray, the amount of drug absorbed is insufficient for efficacy. The present invention provides a method for administering an oxytocin peptide in a more potent formulation and lower volume such that an efficacious amount of the formulation can be delivered using a nasal device for treating an autism spectrum disorder, a disorder manifesting one or more symptoms associated with an autism spectrum disorder, or social and communication deficits.

In one aspect, provided is a method for treating an autism spectrum disorder, a disorder manifesting one or more symptoms associated with an autism spectrum disorder, social and communication deficits, or an anxiety, comprising administering to a subject in need thereof an effective amount of an oxytocin peptide and magnesium ions, wherein the effective amount is delivered via intranasal administration in a volume that is readily absorbed in the nasal cavity. In some embodiments, the volume that allows ready absorption of the oxytocin peptide and the magnesium ions in the nasal cavity is between about 5 μL and about 1000 μL. In some embodiments, the molar ratio between the amount of the oxytocin peptide and the amount of magnesium or magnesium ions is about 1:175, about 1:280, about 1:560, about 1:1100, about 1:1700, or about 1:2000, including any ranges between these ratios.

In one aspect, provided is a method comprising administering to a subject in need thereof an effective amount of an oxytocin peptide and magnesium ions, wherein the effective amount is delivered via intranasal administration in a volume of between about 5 μL and about 1000 μL. In some embodiments, the molar ratio between the amount of the oxytocin peptide and the amount of magnesium or magnesium ions is about 1:175, about 1:280, about 1:560, about 1:1100, about 1:1700, or about 1:2000, including any ranges between these ratios. In some embodiments, the method is for treating one or more symptoms associated with an autism spectrum disorder. In some embodiments, the method is for treating a disorder manifesting one or more symptoms associated with an autism spectrum disorder. In some embodiments, the method is for reducing social and communication deficits. In some embodiments, the method is for treating or decreasing anxiety.

Magnesium is involved in many aspects of life and health such as energy production, oxygen uptake, central nervous system function, electrolyte balance, glucose metabolism and muscle activity. Magnesium has also been found clinically effective in decreasing social and communication deficits in children with autism spectrum disorder. See Mousain-Bosc et al., *Magnes. Res.* 2006, 19(1):53-62. Co-administration of oxytocin and magnesium ions of the present invention results in synergistic or enhanced improvement in social behavior and decreases in anxiety relative to administration of oxytocin alone. The mechanisms underlying these effects are unclear, but are likely to involve either non-competitive blockade of the N-methyl D-aspartate (NMDA) neurotransmitter receptor, or an increase in affinity of the oxytocin receptor action as an allosteric modulator, or both.

In some aspects, provided is a method for treating an autism spectrum disorder comprising administering to a subject in need thereof an effective dose of an oxytocin peptide and magnesium ions, wherein co-administration of the oxytocin peptide and the magnesium ions produces a synergistic or enhanced effect. In some aspects, provided is a method for alleviating or reducing one or more symptoms associated with an autism spectrum disorder comprising administering to a subject in need thereof an effective dose of an oxytocin peptide and magnesium ions, wherein co-administration of the oxytocin peptide and the magnesium ions produces a synergistic or enhanced effect. In some aspects, provided is a method for treating a disorder manifesting one or more symptoms associated with an autism spectrum disorder comprising administering to a subject in need thereof an effective dose of an oxytocin peptide and magnesium ions, wherein co-administration of the oxytocin peptide and the magnesium ions produces a synergistic or enhanced effect. In some embodiments, the oxytocin peptide and the magnesium ions are administered at a dose that produces an overall effect on alleviating or reducing the symptom that is greater than the sum of the effects of equivalent doses of the oxytocin peptide and the magnesium salt administered individually. In some embodiments, the oxytocin peptide and the magnesium ions are administered at a dose that produces a faster onset of effect and/or a longer lasting effect than would occur following administration of the individual agents used alone in equivalent quantities. Examples of symptoms associated with an autism spectrum disorder include but are not limited to persistent deficits in social communication and social interaction, social anxiety, and restricted repetitive behaviors, interests and activities. Other behaviors and characteristics also observed in persons with autism spectrum disorder include an aversion to physical contact, generalized anxiety, a monotone voice or an inability to modulate volume of voice, failure to develop peer relationships, lack of shared enjoyment and interests and lack of social or emotional reciprocity. Examples of disorders which exhibit symptoms similar to those displayed in autism spectrum disorder include, but are not limited to, social anxiety disorder, obsessive-compulsive disorder, social (pragmatic) communication disorder, and neurodevelopmental disorders including but not limited to attention deficit hyperactivity disorder, Prader-Willi syndrome, Timothy syndrome, Fragile-X syndrome, Rett syndrome, and Williams syndrome.

Prader-Willi Syndrome is a complex genetic condition that affects many parts of the body and is caused by a loss of function of genes in a particular region of chromosome 15. Individuals with Prader-Willi Syndrome often have mild to moderate intellectual impairment and learning difficulties and many exhibit behavioral problems including temper outbursts, stubbornness, manipulative behavior, and obsessive-compulsive behaviors including skin picking. Other symptoms often observed in individuals with Prader-Willi Syndrome are persistent deficits in social communication and social interaction, anxiety and irritability, and sleep problems.

In some aspects, provided is a method for treating Prader-Willi syndrome comprising administering to a subject in need thereof an effective dose of an oxytocin peptide and magnesium ions. In some embodiments, co-administration of the oxytocin peptide and the magnesium ions produces a synergistic or enhanced effect. In some embodiments, the oxytocin peptide and the magnesium ions are administered at a dose that produces an overall effect that is greater than the sum of the effects of equivalent doses of the oxytocin peptide and the magnesium salt administered individually. In some embodiments, the oxytocin peptide and the magnesium ions are administered at a dose that produces a faster onset of effect and/or a longer lasting effect than would occur following administration of the individual agents used alone in equivalent quantities. In one embodiment, the invention provides a method for treating Prader-Willi Syndrome comprising administering to a subject in need thereof an effective dose of an oxytocin peptide and magnesium ions, wherein the effective dose of the oxytocin peptide and the magnesium ions is administered intranasally in a liquid formulation, and the volume of the liquid formulation administered is between about 5 µL and about 1000 µL. In some embodiments, the molar ratio between the amount of the oxytocin peptide and the amount of magnesium or magnesium ions is about 1:175, about 1:280, about 1:560, about 1:1100, about 1:1700, or about 1:2000, including any ranges between these ratios.

In some aspects, provided is a method for alleviating or reducing one or more symptoms associated with Prader-Willi syndrome comprising administering to a subject in need thereof an effective dose of an oxytocin peptide and magnesium ions. Examples of symptoms associated with Prader-Willi syndrome include but are not limited to persistent deficits in social communication and social interaction, anxiety and irritability, and sleep problems. In some embodiments, co-administration of the oxytocin peptide and the magnesium ions produces a synergistic or enhanced effect. In some embodiments, the oxytocin peptide and the magnesium ions are administered at a dose that produces an overall effect on alleviating or reducing the symptom that is greater than the sum of the effects of equivalent doses of the oxytocin peptide and the magnesium salt administered individually. In some embodiments, the oxytocin peptide and the magnesium ions are administered at a dose that produces a faster onset of effect and/or a longer lasting effect than would occur following administration of the individual agents used alone in equivalent quantities. Examples of symptoms associated with Prader-Willi syndrome include but are not limited to persistent deficits in social communication and social interaction, anxiety and irritability, and sleep problems. In one embodiment, the invention provides a method for treating Prader-Willi Syndrome comprising administering to a subject in need thereof an effective dose of an oxytocin peptide and magnesium ions, wherein the effective dose of the oxytocin peptide and the magnesium ions is administered intranasally in a liquid formulation, and the volume of the liquid formulation administered is between about 5 µL and about 1000 µL. In some embodiments, the molar ratio between the amount of the oxytocin peptide and the amount of magnesium or magnesium ions is about 1:175, about 1:280, about 1:560, about 1:1100, about 1:1700, or about 1:2000, including any ranges between these ratios.

In some aspects, provided is a method for treating anxiety associated with Prader-Willi syndrome comprising administering to a subject in need thereof an effective dose of an oxytocin peptide and magnesium ions. In some embodiments, co-administration of the oxytocin peptide and the magnesium ions produces a synergistic or enhanced effect. In some embodiments, the oxytocin peptide and the magnesium ions are administered at a dose that produces an overall effect on alleviating or reducing anxiety that is greater than the sum of the effects of equivalent doses of the oxytocin peptide and the magnesium salt administered individually. In some embodiments, the oxytocin peptide and the magnesium ions are administered at a dose that produces a faster onset of effect and/or a longer lasting effect than would occur following administration of the individual agents used alone in equivalent quantities. In one embodiment, the invention provides a method for treating anxiety associated with Prader-Willi Syndrome comprising administering to a subject in need thereof an effective dose of an oxytocin peptide and magnesium ions, wherein the effective dose of the oxytocin peptide and the magnesium ions is administered intranasally in a liquid formulation, and the volume of the liquid formulation administered is between about 5 µL and about 1000 µL. In some embodiments, the molar ratio between the amount of the oxytocin peptide and the amount of magnesium or magnesium ions is about 1:175, about 1:280, about 1:560, about 1:1100, about 1:1700, or about 1:2000, including any ranges between these ratios.

In one aspect, the invention provides a method for treating social and communication deficits comprising administering to a subject in need thereof an effective dose of an oxytocin peptide and magnesium ions, wherein co-administration of the oxytocin peptide and the magnesium ions produces a synergistic or enhanced effect. In one aspect, the invention provides a method for treating anxiety comprising administering to a subject in need thereof an effective dose of an oxytocin peptide and magnesium ions, wherein co-administration of the oxytocin peptide and the magnesium ions produces a synergistic or enhanced effect. In some embodiments, the oxytocin peptide and the magnesium ions are administered at a dose that produces an overall effect on reducing social and communication deficits and/or anxiety that is greater than the sum of the effects of equivalent doses of the oxytocin peptide and the magnesium salt administered individually. In some embodiments, the molar ratio between the amount of the oxytocin peptide and the amount of magnesium or magnesium ions is about 1:175, about 1:280, about 1:560, about 1:1100, about 1:1700, or about 1:2000, including any ranges between these ratios. In some embodiments, the social and communication deficits is an impairment in communication skills and/or social interaction, a lack of eye contact, and/or an inability to form and/or maintain social relationships.

In some aspects, provided is a method for treating anxiety associated with autism spectrum disorder comprising administering to a subject in need thereof an effective dose of an oxytocin peptide and magnesium ions. In some embodiments, co-administration of the oxytocin peptide and the magnesium ions produces a synergistic or enhanced effect. In some embodiments, the oxytocin peptide and the magnesium ions are administered at a dose that produces an overall effect on alleviating or reducing anxiety that is greater than the sum of the effects of equivalent doses of the oxytocin peptide and the magnesium salt administered individually. In some embodiments, the oxytocin peptide and the magnesium ions are administered at a dose that produces a faster onset of effect and/or a longer lasting effect than would occur following administration of the individual agents used alone in equivalent quantities. In some embodiments, the molar ratio between the amount of the oxytocin peptide and the amount of magnesium or magnesium ions is about 1:175, about 1:280, about 1:560, about 1:1100, about 1:1700, or about 1:2000, including any ranges between these ratios.

The oxytocin peptide and the magnesium ions may be administered concurrently or sequentially. In some embodiments, the oxytocin peptide is administered concurrently with the magnesium ions in the same unit dose. In some embodiments, the oxytocin peptide is administered concurrently with the magnesium ions but in separate unit doses or formulations. In some embodiments, oxytocin peptide and the magnesium ions are administered sequentially. In some embodiments, the magnesium ions are administered to the subject in a first administration and then the oxytocin peptide is administered to the subject in a second administration. In some of these embodiments, the oxytocin peptide is administered between about 10 minutes and about 2 hours after administration of the magnesium ions. In some of these embodiments, the oxytocin peptide is administered between about 10 minutes and about 2 hours, between about 10 minutes and about 1 hour, between about 10 minutes and about 30 minutes, between about 20 minutes and about 2 hours, between about 20 minutes and about 1 hour, between about 30 minutes and about 2 hours or between about 30 minutes and about 1 hour after administration of the magnesium ions. In some of these embodiments, the oxytocin peptide is administered about 10 minutes, about 15 minutes, about 20 minutes, about 30 minutes, about 45 minutes, about 60 minutes, about 90 minutes or about 120 minutes after administration of the magnesium ions. In some of these embodiments, the oxytocin peptide is administered about 10 minutes, about 15 minutes, about 20 minutes, or about 30 minutes after administration of the magnesium ions. In one embodiment, the oxytocin peptide is administered to the subject first and then the magnesium ions are administered to the subject. In some embodiments, the subject is a human.

Interleukin-6 (IL-6) has been demonstrated to induce the elevation of oxytocin receptor expression in various tissues (e.g., Young et al., *J. Neuroendocrinology,* 1997; 9:859-65). Thus, serum IL-6 levels may be used as a biomarker of potential efficacy of oxytocin, for example, when nasally administrated with magnesium.

In some aspects, IL-6 is used as a biomarker of efficacy of administration of the oxytocin peptide in a subject according to a method detailed herein for treating an autism spectrum disorder, a disorder manifesting one or more symptoms associated with an autism spectrum disorder, social and communication deficits, or anxiety. and to select a subject for application of the methods. In some embodiments, IL-6 is used to select a subject (e.g., a human) for administration of an oxytocin peptide (e.g., nasal administration of an oxytocin peptide in combination with magnesium ions).

In some embodiments, the subject is selected for treatment based on the subject having a high level of IL-6. The level of IL-6 may be high as compared to a control or reference. In some embodiments, a level of IL-6 is high compared to a control or reference if it is significantly greater than the control or reference as determined by an appropriate statistical analysis. In some embodiments, a level of IL-6 is high compared to a control or reference if it is at least one standard deviation greater than the control or reference. In some embodiments, the control is a value for the level of 11-6 as determined in age- and gender-matched healthy subjects. In some embodiments, the reference is a reported value for the level of IL-6, such as a value reported for IL-6 in age- and gender-matched healthy subjects. In some embodiments, the level of IL-6 is determined as the level of IL-6 in a sample (such as a tissue or fluid sample) from the subject, including, without limitation, whole blood, serum, plasma, tears, and the like. The level of L-6 in a sample can be determined by any method known in the art, such as by immunoassay, e.g., ELISA-based assay. See for example Yang, C-J., et al. *Neuroscience* 284: 290-296, 2015; Emanuele, E., et al. *Neuroscience letters* 471(3): 162-165, 2010; Ashwood, P., et al. *Brain, behavior, and immunity* 25(1): 40-45, 2011; and Malik, M., et al. *Immunobiology* 216(1): 80-85, 2011.

In some embodiments, the method for treating an autism spectrum disorder, a disorder manifesting one or more symptoms associated with an autism spectrum disorder, social and communication deficits, or anxiety, comprises measuring the level of IL-6 (e.g., serum level of IL-6) in a subject and administering to a subject having a high IL-6 level an effective dose of an oxytocin peptide and magnesium ions.

In one aspect, the method for treating an autism spectrum disorder, a disorder manifesting one or more symptoms associated with an autism spectrum disorder, social and communication deficits, or anxiety, comprising administering to a subject in need thereof an effective dose of an oxytocin peptide and magnesium ions, wherein co-administration of the oxytocin peptide and the magnesium ions produces a synergistic or enhanced effect, further comprises administering to the subject an effective amount of interleukin-6 (IL-6). In some embodiments, the effective amount of IL-6 results in an increase in expression of the oxytocin receptor (OTR) in the subject.

In some embodiments, according to any of the methods described herein where IL-6 is administered to the subject, the oxytocin peptide and the IL-6 may be administered concurrently or sequentially. In some embodiments, the oxytocin peptide is administered concurrently with the IL-6 in the same unit dose. In some embodiments, the oxytocin peptide is administered concurrently with the IL-6 but in separate unit doses or formulations. In some embodiments, oxytocin peptide and the IL-6 are administered sequentially. In some embodiments, the IL-6 is administered to the subject in a first administration and then the oxytocin peptide is administered to the subject in a second administration. In some of these embodiments, the oxytocin peptide is administered between about 1 minutes and about 4 hours after administration of the IL-6. In some of these embodiments, the oxytocin peptide is administered between about 1 minutes and about 4 hours, between about 10 minutes and about 4 hours, between about 10 minutes and about 3 hours, between about 10 minutes and about 2 hours, between about 10 minutes and about 1 hour, between about 10 minutes and about 30 minutes, between about 20 minutes and about 4 hours, between about 20 minutes and about 3 hours, between about 20 minutes and about 2 hours, between about 20 minutes and about 1 hour, between about 30 minutes and about 4 hours, between about 30 minutes and about 3 hours, between about 30 minutes and about 2 hours or between about 30 minutes and about 1 hour after administration of the IL-6. In some of these embodiments, the oxytocin peptide is administered about 1 minute, about 10 minutes, about 15 minutes, about 20 minutes, about 30 minutes, about 45 minutes, about 60 minutes, about 90 minutes, about 120 minutes, about 150 minutes, about 180 minutes, about 210 minutes, or about 240 minutes after administration of the IL-6. In some of these embodiments, the oxytocin peptide is administered about 10 minutes, about 15 minutes, about 20 minutes, or about 30 minutes after administration of the IL-6. In one embodiment, the oxytocin peptide is administered to the subject first and then the IL-6 is administered to the subject. In some embodiments, the subject is a human. In some of these embodiments, magnesium ions are administered concurrently with the oxytocin peptide and/or IL-6, prior to either or both of the oxytocin peptide and IL-6, or after either or both of the oxytocin peptide and IL-6.

The oxytocin peptide and the magnesium ions may be administered via the same route or different routes to a subject in need thereof. In some embodiments, the oxytocin peptide is administered via craniofacial mucosal administration (e.g., nasal, buccal, sublingual or ocular administration). In one embodiment, the oxytocin peptide and the magnesium ions are both administered intranasally in the same formulation. In one embodiment, oxytocin peptide is administered via craniofacial mucosa and the magnesium ions are administered systemically, e.g., intravenously, intramuscularly, orally, subcutaneously, or intrathecally.

In some embodiments, the oxytocin peptide is administered via intranasal administration. In some embodiments, the oxytocin peptide and the magnesium ions are administered via intranasal administration. The oxytocin peptide and/or the magnesium ions can be administered to the mucosa tissue within the nasal cavity using a suitable device for intranasal delivery such as a nasal delivery device described herein. Suitable regions within the nasal cavity include, but are not limited to, the inferior two-thirds of the nasal cavity, or the upper third, or the entire nasal passage. In some embodiments, the oxytocin peptide and/or the magnesium ions are administered to the upper third of the nasal cavity. In some embodiments, the oxytocin peptide and/or the magnesium ions are administered to the lower two thirds of the nasal cavity. In some embodiments, the oxytocin peptide and/or the magnesium ions are administered specifically to reach both the lower two thirds and the upper third of the nasal cavity. In some embodiments, a method is provided for treating an autism spectrum disorder, one or more symptoms associated with an autism spectrum disorder, or a disorder manifesting one or more symptoms associated with an autism spectrum disorder, comprising intranasally administering to a subject in need thereof an effective dose of an oxytocin peptide and magnesium ions, wherein co-administration of the oxytocin peptide and the magnesium ions produces a synergistic or enhanced effect. In some embodiments, the method is for treating social and communication deficits or an anxiety.

In some embodiments, according to any of the methods described herein where IL-6 is administered to the subject, the IL-6 is administered via intranasal administration. The IL-6 can be administered to the mucosa tissue within the nasal cavity using a suitable device for intranasal delivery such as a nasal delivery device described herein. In some embodiments, the IL-6 is administered systemically, e.g., intravenously, intramuscularly, orally, subcutaneously, or intrathecally.

In some embodiments, the oxytocin peptide is human oxytocin consisting of Cys-Tyr-Ile-Gln-Asn-Cys-Pro-Leu-Gly (SEQ. ID NO: 1). In some embodiments, the effective dose of the oxytocin peptide is about 0.5 µg to about 2000 µg. In some embodiments, the effective dose of the oxytocin peptide is about 0.5 µg to about 1000 µg, about 1 µg to about 1000 µg or about 1 µg to about 2000 µg. In some embodiments, the effective dose of the oxytocin peptide is about 4 µg to about 1000 µg, about 8 µg to about 1000 µg, about 8 µg to about 800 µg, about 8 µg to about 500 µg, about 8 µg to about 400 µg, about 8 µg to about 300 µg about 8 µg to about 200 µg, about 8 µg to about 100 µg, about 8 µg to about 80 µg, about 8 µg to about 50 µg, about 10 µg to about 1000 µg, about 10 µg to about 500 µg, about 10 µg to about 200 µg, about 10 µg to about 100 µg, about 16 µg to about 1000 µg, about 16 µg to about 800 µg, about 16 µg to about 500 µg, about 16 µg to about 400 µg, about 16 µg to about 200 µg, about 16 µg to about 160 µg, about 16 µg to about 120 µg, about 16 µg to about 80 µg, about 20 µg to about 1000 µg, about 20 µg to about 800 µg, about 20 µg to about 500 µg, about 20 µg to about 200 µg, about 20 µg to about 100 µg, about 30 µg to about 1000 µg, about 30 µg to about 500 µg, about 30 µg to about 300 µg, about 30 µg to about 120 µg, about 30 µg to about 90 µg, about 50 µg to about 1000 µg, about 50 µg to about 500 µg, about 50 µg to about 250 µg, about 50 µg to about 100 µg, or about 50 µg to about 80 µg. In some embodiments, the effective dose of the oxytocin peptide is about 8 µg, about 16 µg, about 32 µg, about 48 µg, about 64 µg, about 80 µg, about 96 µg, about 128 µg, about 256 µg, about 10 µg, about 20 µg, about 30 µg, about 40 µg, about 50 µg, about 60 µg, about 70 µg, about 80 µg, about 90 µg, about 100 µg, about 120 µg, about 150 µg, about 200 µg, about 400 µg, about 600 µg, about 800 µg or about 100 µg. In a preferred embodiment, the effective dose of the oxytocin peptide is about 8 µg to about 120 µg, about 15 µg to about 120 µg, about 30 µg to about 120 µg, or about 66 µg.

In some embodiments, the effective dose of the oxytocin peptide is about 0.25 IU to about 1000 IU. In some embodiments, the effective dose of the oxytocin peptide is about 0.25 IU to about 500 IU, about 0.5 IU to about 500 IU or about 0.5 IU to about 1000 IU. In some embodiments, the effective dose of the oxytocin peptide is about 2 IU to about 500 IU, about 4 IU to about 500 IU, about 4 IU to about 400 IU, about 4 IU to about 250 IU, about 4 IU to about 200 IU, about 4 IU to about 150 IU, about 4 IU to about 100 IU, about 4 IU to about 50 IU, about 4 IU to about 40 IU, about 4 IU to about 25 IU, about 5 IU to about 500 IU, about 5 IU to about 250 IU, about 5 IU to about 100 IU, about 5 IU to about 50 IU, about 8 IU to about 500 IU, about 8 IU to about 400 IU, about 8 IU to about 250 IU, about 8 IU to about 200 IU, about 8 IU to about 100 IU, about 8 IU to about 80 IU, about 8 IU to about 60 IU, about 8 IU to about 40 IU, about 10 IU to about 500 IU, about 10 IU to about 400 IU, about 10 IU to about 250 IU, about 10 IU to about 100 IU, about 10 IU to about 50 IU, about 15 IU to about 500 IU, about 15 IU to about 250 IU, about 15 IU to about 150 IU, about 15 IU to about 60 IU, about 15 IU to about 45 IU, about 25 IU to about 500 IU, about 25 IU to about 250 IU, about 25 IU to about 125 IU, about 25 IU to about 50 IU, or about 25 IU to about 40 IU. In some embodiments, the effective dose of the oxytocin peptide is about 4 IU, about 8 IU, about 16 IU, about 24 IU, about 32 IU, about 40 IU, about 48 IU, about 64 IU, about 128 IU, about 5 IU, about 10 IU, about 15 IU, about 20 IU, about 25 IU, about 30 IU, about 35 IU, about 40 IU, about 45 IU, about 50 IU, about 60 IU, about 75 IU, about 100 IU, about 200 IU, about 300 IU, about 400 IU or about 50 IU. In a preferred embodiment, the effective dose of the oxytocin peptide is about 4 IU to about 60 IU, about 7.5 IU to about 60 IU, about 15 IU to about 60 IU, or about 30 IU.

The dose or amount of oxytocin in the combination is, in one embodiment, effective to provide a clinically measurable improvement in a symptom of an autism spectrum disorder or a related disorder. The combination of oxytocin and the magnesium ions provides a synergistic or enhanced effect to improve the autism spectrum disorder or a related disorder. In some embodiments, oxytocin is administered at a sub-therapeutically effective dose relative to a dose of oxytocin administered as a single agent. The dose of oxytocin as a single agent depends, in part, on the route of administration. Accordingly, the dose of oxytocin in the combination therapy described herein will also depend, in part, on the route of administration.

The optimal dosage of the magnesium ions may depend on the specific disorder or symptom, the type of synergistic or enhanced effect desired, and other factors such as the route of administration. The optimal dose may be measured in the total amount of magnesium ions administered, or the concentration of magnesium ions in the formulation administered. In some embodiments, the effective dose of magnesium ions administered is about 50 µg to about 68 mg. In some embodiments, the effective dose of magnesium ions administered is about 50 µg to about 34 mg, or about 1 mg to about 3 mg. In some embodiments, the effective dose of magnesium ions administered is about 1.3 mg, or about 2.6 mg. In some embodiments, the effective dose of magnesium ions administered is about 1.2 mg, or about 2.4 mg. In some embodiments, the effective dose of magnesium ions administered is about 50 µg to about 17 mg, about 50 µg to about 8 mg, about 50 µg to about 4 mg, about 50 µg to about 2 mg, about 50 µg to about 1 mg, about 50 µg to about 500 µg, about 100 µg to about 68 mg, about 100 µg to about 34 mg, about 100 µg to about 17 mg, about 100 µg to about 8 mg, about 100 µg to about 4 mg, about 100 µg to about 2 mg, about 100 µg to about 1 mg, about 100 µg to about 500 µg, about 200 µg to about 68 mg, about 200 µg to about 34 mg, about 200 µg to about 17 mg, about 200 µg to about 8 mg, about 200 µg to about 4 mg, about 200 µg to about 2 mg, about 200 µg to about 1 mg, about 200 µg to about 500 µg, about 500 µg to about 68 mg, about 500 µg to about 34 mg, about 500 µg to about 17 mg, about 500 µg to about 8 mg, about 500 µg to about 5 mg, about 500 µg to about 4 mg, about 500 µg to about 3 mg, about 500 µg to about 2 mg, about 500 µg to about 1 mg, about 1 mg to about 68 mg, about 1 mg to about 34 mg, about 1 mg to about 17 mg, about 1 mg to about 8 mg, about 1 mg to about 6 mg, about 1 mg to about 5 mg, about 1 mg to about 4 mg, about 1 mg to about 3 mg, about 1 mg to about 2 mg, about 1.5 mg to about 8 mg, about 1.5 mg to about 6 mg, about 1.5 mg to about 5 mg, about 1.5 mg to about 4 mg, about 1.5 mg to about 3 mg, about 1.5 mg to about 2 mg, about 1.3 mg to about 2.6 mg, or about 1.2 mg to about 2.4 mg. In some embodiments, the magnesium ions are provided using a magnesium salt (e.g., magnesium citrate and/or magnesium chloride).

In some embodiments, the magnesium salt administered comprises magnesium chloride and the effective dose of the magnesium salt is about 0.48 mg to about 600 mg of magnesium chloride hexahydrate ($MgCl_2 \cdot 6H_2O$, MW 203.3). In some embodiments, the effective dose of magnesium chloride hexahydrate is about 0.48 mg to about 300 mg, about 0.5 mg to about 150 mg, about 0.5 mg to about 75 mg, about 5 mg to about 150 mg, about 5 mg to about 75 mg, about 5 mg to about 50 mg, about 10 mg to about 600 mg, about 10 mg to about 300 mg, about 10 mg to about 150 mg, about 10 mg to about 75 mg, about 10 mg to about 50 mg, about 10 mg to about 30 mg, or about 12 mg to about 24 mg. In some preferred embodiments, the effective dose of magnesium chloride hexahydrate is about 6 mg, about 12 mg, about 18 mg, about 24 mg or about 30 mg.

In some embodiments, the magnesium salt administered is magnesium citrate and the effective dose of the magnesium salt is about 0.48 mg to about 600 mg of magnesium citrate. In some embodiments, the effective dose of magnesium citrate (e.g., anhydrous magnesium citrate dibasic, MW. 214.4) is about 0.48 mg to about 300 mg, about 0.5 mg to about 150 mg, about 0.5 mg to about 75 mg, about 5 mg to about 150 mg, about 5 mg to about 75 mg, about 5 mg to about 50 mg, about 10 mg to about 600 mg, about 10 mg to about 300 mg, about 10 mg to about 150 mg, about 10 mg to about 75 mg, about 10 mg to about 50 mg, about 10 mg to about 30 mg, or about 12 mg to about 24 mg. In some preferred embodiments, the effective dose of magnesium citrate (e.g., anhydrous magnesium citrate dibasic, MW. 214.4) is about 6 mg, about 12 mg, about 18 mg, about 24 mg or about 30 mg. In some embodiments, the effective dose of magnesium citrate is about 0.48 mg to about 12 mg, about 0.5 mg to about 10 mg, about 0.5 mg to about 8 mg, about 0.5 mg to about 5 mg, about 0.5 mg to about 2.5 mg, about 0.5 mg to about 1 mg, about 1 mg to about 10 mg, about 1 mg to about 8 mg, about 1 mg to about 5 mg, about 1 mg to about 2 mg, about 2 mg to about 10 mg, about 2 mg to about 8 mg, about 2 mg to about 6 mg, about 2 mg to about 4 mg, about 3 mg to about 10 mg, about 4 mg to about 10 mg, about 4 mg to about 8 mg, about 4 mg to about 6 mg, about 5 mg to about 10 mg, about 5 mg to about 8 mg, about 5 mg to about 7 mg, about 5 mg to about 6 mg, about 6 mg to about 10 mg, about 6 mg to about 8 mg, or about 6 mg to about 7 mg. If other magnesium salts are substituted for magnesium citrate, the effective dose of the magnesium salt provides an amount of magnesium ions equivalent to that provided by magnesium citrate.

It is intended and understood that each and every dosage of the magnesium ions described herein may be combined with each and every dosage of the oxytocin peptide described herein as if each and every combination is individually stated. For example, in some embodiments, the effective dose of the oxytocin peptide is about 0.5 µg to about 2000 µg and the effective dose of the magnesium ions is about 50 µg to about 68 mg of magnesium. In some embodiments, the effective dose of the oxytocin peptide is about 15 µg to about 120 µg (e.g., about 60 µg or about 66 µg) and the effective dose of the magnesium ions is equivalent to the amount of magnesium ions provided by about 10 mg to about 30 mg (e.g., about 12 mg or about 24 mg) of magnesium citrate.

In some embodiments, provided is a method for treating an autism spectrum disorder, a disorder manifesting one or more symptoms associated with an autism spectrum disorder, social and communication deficits, or an anxiety, comprising administering (for example by intranasal administration) to a subject in need thereof an effective dose of an oxytocin peptide and magnesium ions, wherein the weight ratio between the dose of the oxytocin peptide administered and the dose of the magnesium ions administered is between about 1:1 to about 1:1000, preferably between about 1:2 to about 1:200, more preferably about 1:20, about 1:30, about 1:35, about 1:40, about 1:45, about 1:50, about 1:60, or any of the OT/Mg (w) ratios described herein for the magnesium-containing oxytocin peptide formulation or composition. In some embodiments, a method is provided for treating an autism spectrum disorder, a disorder manifesting one or more symptoms associated with an autism spectrum disorder, social and communication deficits, or an anxiety, comprising administering (for example by intranasal administration) to a subject in need thereof an effective dose of an oxytocin peptide and magnesium ions, wherein the molar ratio between the dose of the oxytocin peptide administered and the dose of the magnesium ions administered is between about 1:40 to about 1:40000, preferably between about 1:80 to about 1:8000, more preferably about 1:175, about 1:280, about 1:500, about 1:560, about 1:800, about 1:1000, about 1:1100, about 1:1200, about 1:1400, about 1:1600, about 1:1700, about 1:1800, about 1:2000, about 1:2400, about 1:3000, or any of the OT/Mg (m) ratios described herein for the magnesium-containing oxytocin peptide formulation or composition. In some of these embodiments, the oxytocin peptide is human oxytocin consisting of Cys-Tyr-Ile-Gln-Asn-Cys-Pro-Leu-Gly (SEQ. ID NO: 1). In some of this embodiment, the magnesium ions are provided by magnesium citrate and/or magnesium chloride. In some of these embodiments, the social and communication deficits is an impairment in communication skills and/or social interaction, a lack of eye contact, and/or an inability to form and/or maintain social relationships.

In one embodiment, a method is provided for treating an autism spectrum disorder, a disorder manifesting one or more symptoms associated with an autism spectrum disorder, social and communication deficits, or an anxiety, comprises intranasally administering to a subject in need thereof a dose of about 0.5 µg to about 2000 µg (e.g., about 8 µg to about 300 µg, about 15 µg to about 120 µg or about 66 µg) of an oxytocin peptide and a dose of about 50 µg to about 68 mg, about 50 µg to about 34 mg, about 1 mg to about 3 mg, about 1.3 mg, or about 2.6 mg of magnesium or magnesium ions. In one embodiment, the method comprises intranasally administering to a subject in need thereof an effective amount of a magnesium-containing oxytocin peptide formulation or composition described herein. In one embodiment, the method comprises intranasally administering to a subject in need thereof an effective amount of an oxytocin peptide and magnesium ions in a liquid formulation of between about 5 µL and about 1000 µL in volume. In one embodiment, the method comprises intranasally administering to a subject in need thereof an effective amount of a magnesium-containing oxytocin peptide formulation or composition comprising between about 0.01 mg/mL and about 16 mg/mL (e.g., about 0.1 mg/mL and about 16 mg/mL) of oxytocin and between about 1 mg/mL and about 30 mg/mL of magnesium or magnesium ions. In one embodiment, the method comprises intranasally administering to a subject in need thereof an effective amount of a magnesium-containing oxytocin peptide formulation comprising between about 0.01 mg/mL and about 16 mg/mL (e.g., about 0.1 mg/mL and about 16 mg/mL or about 0.15 mg/mL and about 1.5 mg/mL) of oxytocin and between about 1% and about 25% (by weight) (e.g., about 1% to about 15% or about 10% to about 14%) of magnesium citrate. In one embodiment, the method comprises intranasally administering to a subject in need thereof an effective amount of a magnesium-containing oxytocin peptide formulation comprising between about 5 IU/mL and about 8000 IU/mL (e.g., about 50 IU/mL and about 8000 IU/mL or about 75 IU/mL and about 750 IU/mL) of oxytocin and between about 1% and about 25% (by weight) (e.g., about 1% to about 15%, about 10% to about 14%, or about 12%) of magnesium citrate. In one embodiment, the method comprises intranasally administering to a subject in need thereof an effective amount of a magnesium-containing oxytocin peptide formulation comprising between about 0.01 mg/mL and about 16 mg/mL (e.g., about 0.1 mg/mL and about 16 mg/mL or about 0.15 mg/mL and about 1.5 mg/mL) of oxytocin and between about 1% and about 25% (by weight) (e.g., about 1% to about 15%, about 8% to about 12%, or about 10%) of magnesium chloride hexahydrate. In one embodiment, the method comprises intranasally administering to a subject in need thereof an effective amount of a magnesium-containing oxytocin peptide formulation comprising between about 5 IU/mL and about 8000 IU/mL (e.g., about 50 IU/mL and about 8000 IU/mL or about 75 IU/mL and about 750 IU/mL) of oxytocin and between about 1% and about 25% (by weight) (e.g., about 1% to about 15%, about 8% to about 12%, or about 10%) of magnesium chloride hexahydrate.

In some embodiments, the effective dose of the oxytocin peptide and the magnesium ions comprises about 0.5 µg (or 0.25 IU) to about 2000 µg (or 1000 IU) of the oxytocin peptide administered in an aqueous solution containing about 0.1% to about 2.8% (w/v) of magnesium. In some embodiments, the effective dose of the oxytocin peptide and the magnesium ions comprises about 8 µg (or 4 IU) to about 1000 µg (or 500 IU) of the oxytocin peptide administered in an aqueous solution containing about 0.11% to about 1.65% (w/v) of magnesium. In some embodiments, the effective dose of the oxytocin peptide and the magnesium ions comprises about 15 µg (or 7.5 IU) to about 120 µg (or about 60 IU) (e.g., about 60 µg or 30 IU) of the oxytocin peptide administered in an aqueous solution containing about 1.1% to about 1.6% (e.g., about 1.2% or about 1.35%) magnesium. In one embodiment, the effective dose of the oxytocin peptide and the magnesium ions comprises about 60 µg (or 30 IU) of the oxytocin peptide administered in an aqueous solution containing about 1.2% or about 1.35% of magnesium.

In some embodiments, the effective dose of the oxytocin peptide and the magnesium ions is administered intranasally in a liquid formulation, and the volume of the liquid formulation administered is between about 5 µL and about 1000 µL. In some embodiments, the volume administered is between about 5 µL and about 500 µL, between about 5 µL and about 250 µL, between about 5 µL and about 100 µL, between about 5 µL and about 50 µL, between about 10 µL and about 1000 µL, between about 10 µL and about 500 µL, between about 10 µL and about 250 µL, between about 10 µL and about 100 µL, between about 25 µL and about 1000 µL, between about 25 µL and about 500 µL, between about 25 µL and about 250 µL, between about 25 µL and about 100 µL, between about 50 µL and about 1000 µL, between about 50 µL and about 750 µL, between about 50 µL and about 500 µL, between about 50 µL and about 450 µL, between about 50 µL and about 400 µL, between about 50 µL and about 350 µL, between about 50 µL and about 300 µL, between about 50 µL and about 250 µL, between about 50 µL and about 200 µL, between about 50 µL and about 150 µL, between about 100 µL and about 500 µL, between about 100 µL and about 400 µL, between about 100 µL and about 300 µL, or between about 100 µL and about 200 µL. In some embodiments, the volume administered is about 50 µL, about 100 µL, about 150 µL, about 200 µL, about 250 µL, about 300 µL, about 350 µL, about 400 µL, about 450 µL, or about 500 µL. In some embodiments, the effective dose of the oxytocin peptide and the magnesium ions is administered intranasally in a liquid formulation contained in a nasal device described herein.

The combination of an oxytocin peptide and magnesium ions described herein may be used for the treatment of any social and communication deficits treatable by oxytocin, such as impairment in communication skills and/or social interaction, lack of eye contact, and/or an inability to form and/or maintain social relationships. Thus, provided is a method for treating social and communication deficits comprising administering to a subject in need thereof an effective dose of an oxytocin peptide and magnesium ions, wherein the social and communication deficit is impairment in communication skills and/or social interaction, lack of eye contact, and/or an inability to form and/or maintain social relationships. In one embodiment, the method comprises intranasally administering to a subject in need thereof an effective dose of an oxytocin peptide and magnesium ions. In some embodiments, the molar ratio between the amount of the oxytocin peptide and the amount of magnesium or magnesium ions is about 1:175, about 1:280, about 1:560, about 1:1100, about 1:1700, or about 1:2000, including any ranges between these ratios.

In one embodiment, a method is provided for treating an autism spectrum disorder, a disorder manifesting one or more symptoms associated with an autism spectrum disorder, social and communication deficits, or an anxiety, comprising intranasally administering to a subject in need thereof (e.g., a human or veterinary patient) an effective dose of an oxytocin peptide and magnesium ions, wherein co-administration of the oxytocin peptide and the magnesium ions produces a synergistic or enhanced effect. In some embodiments, the oxytocin peptide is human oxytocin consisting of Cys-Tyr-Ile-Gln-Asn-Cys-Pro-Leu-Gly (SEQ. ID NO:1). In some embodiments, the effective dose of the oxytocin peptide is about 0.5 µg (or 0.25 IU) to about 2000 µg (or 1000 IU), preferably about 8 µg (or 4 IU) to about 1000 µg (or 500 IU), more preferably about 15 µg (or 7.5 IU) to about 120 µg (or 60 IU). In some embodiments, the effective dose of the magnesium ions is about 50 µg to about 68 mg. In some embodiments, the magnesium ions are provided using a magnesium salt (e.g., magnesium chloride and/or magnesium citrate) administered in an amount to provide about 50 µg to about 68 mg of magnesium. In some embodiments, the effective dose of the magnesium ions is provided by using about 0.48 mg to about 600 mg of magnesium citrate. In some embodiments, the effective dose of the magnesium ions is provided by using about 0.42 mg to about 540 mg of magnesium chloride hexahydrate. In some embodiments, the effective dose of the oxytocin peptide and the magnesium ions comprises about 15 µg (or 7.5 IU) to about 120 µg (or 60 IU) (e.g., about 60 µg or 30 IU) of the oxytocin peptide administered in an aqueous solution containing about 1.1% to about 1.54% (e.g., about 1.2% or about 1.35%) (w/v) magnesium. In some embodiments, the effective dose of the oxytocin peptide and the magnesium ions comprises about 10 µg to about 120 µg (e.g., about 66 µg) of the oxytocin peptide administered in an aqueous solution containing about 10% to about 14% (e.g., about 12%) (w/v) magnesium citrate.

Kits

Provided herein are kits for carrying out any of the methods described herein. Kits are provided for use in treatment of an autism spectrum disorder, a disorder manifesting one or more symptoms associated with an autism spectrum disorder, social and communication deficits, or anxiety. In some embodiments, the kit comprises an oxytocin peptide and magnesium ions, wherein the oxytocin peptide and the magnesium ions are in an amount that produces a synergistic or enhanced effect when used in the treatment of an autism spectrum disorder, a disorder manifesting one or more symptoms associated with an autism spectrum disorder, social and communication deficits, or anxiety, and a device for craniofacial mucosal administration (e.g., intranasal administration) in suitable packaging. Kits may further comprise a protease inhibitor and/or at least one absorption enhancer. Kits may further comprise IL-6. Other kits may further comprise instructions providing information to the user and/or health care provider for carrying out any one of the methods described herein. Kits may further comprise reagents/tools for measuring IL-6 levels in a subject; and optionally instructions for predicting efficacy of nasal oxytocin and magnesium ions.

Also provided is a kit comprising a magnesium-containing oxytocin peptide formulation described herein contained in a device for craniofacial mucosal administration (e.g., a device for intranasal administration such as a nasal pump apparatus) and suitable packaging. The kit may further comprise instructions for administering the magnesium-containing oxytocin peptide formulation in a subject in need thereof.

The instructions relating to the use of the kit for carrying out the invention generally describe how the contents of the kit are used to carry out the methods of the invention. Instructions supplied in the kits of the invention are typically written instructions on a label or package insert (e.g., a paper sheet included in the kit), but machine-readable instructions (e.g., instructions carried on a magnetic or optical storage disk) are also acceptable.

EXAMPLES

The invention can be further understood by reference to the following examples, which are provided by way of illustration and are not meant to be limiting.

Example 1: Exemplary Preparation of a Magnesium-Containing Oxytocin Peptide Formulation Example 1A The drug product formulation, which is hypertonic and targeted at pH 4.5, consists of Oxytocin USP (150 IU/mL); Magnesium Chloride USP (as the hexahydrate or anhydrous salt); Citric Acid USP (as the anhydrous or monohydrate form); Sodium Hydroxide NF; and Sterile Water for Injection USP. The quantitative composition is provided in Table 1. The molar ratio of oxytocin to magnesium ions in the formulation is about 1:1679. All ingredients meet the compendial (USP/NF) requirements from the corresponding monographs.

TABLE 1

| Component | Composition | | Function |
|---|---|---|---|
| | mg/mL | wt % | |
| Oxytocin USP[1] | 150 IU | Footnote 1 | Active ingredient |
| Magnesium Chloride USP[2] | 101.7 | 10.2 | Chelating system |
| Citric Acid USP[3] | 9.6 | 0.96 | |
| Sodium Hydroxide NF | qs pH 4.5 | qs pH 4.5 | pH adjustment |
| Sterile Water for Injection USP | qs | qs | Solvent |
| Total | ca. 1000 | 100 | |

[1]The exact amount of oxytocin to be used is based on its oxytocic activity from the supplier certificate of analysis.
[2]The composition values for magnesium chloride represent those of the hexahydrate; the anhydrous salt may be used as well, with corresponding adjustment of composition.
[3]The composition values for citric acid represent those of the anhydrous form; the monohydrate may be used as well, with corresponding adjustment of composition.

The drug product is manufactured by dissolving the ingredients in Sterile Water for Injection, sterile filtering and filling into a vial with a snap on preservative free pump, and is tested in general accordance with the July 2002 FDA nasal spray guidance.

In one example, a 10-L batch of the magnesium-containing oxytocin formulation according to the composition provided in Table 1 was prepared as following: Filled the formulation vessel with water to about 60% of the required batch volume. While stirring at ambient temperature, added in the following order the required quantities of: Sodium Chloride, Citric Acid and Magnesium Chloride hexahydrate. The materials dissolved readily. No heat was required, just gentle stirring. Adjusted the pH of the solution to 4.5 with the addition of IN NaOH. (If over-titrated, 10% HCl could be used to back-titrate to pH 4.5.) Added the required amount of oxytocin and stirred until dissolved. Added water to bring the batch to the final weight/volume. Stirred until the solution was homogenous.

Example 1B

The drug product formulation, which is isotonic and targeted at pH 4.5, consists of Oxytocin USP (150 IU/mL); Magnesium Citrate, Sodium Chloride USP; Sodium Acetate Trihydrate USP; Glacial Acetic Acid USP; and Sterile Water for Injection USP. Quantitative compositions are provided in Table 2. The molar ratio of oxytocin to magnesium ions in the formulation is about 1:1992. The target pH of 4.5 is selected based on the optimal formulation stability at or near this pH (Hawe, et al. *Pharmaceut. Res.* 2009, 26:1679-1688). All ingredients meet the compendial (USP/NF) requirements from the corresponding monographs.

To prepare a stock oxytocin solution, lyophilized oxytocin (2 mg) is added to 1 mL of water (USP), 0.90% physiological saline or phosphate buffered saline in a 5 mL glass vessel. The solution is stirred until all the oxytocin is dissolved, and the pH is adjusted to between 3.5 and 8.5, producing 1 mL of a 2 mg/mL (about 1000 IU/mL) liquid oxytocin formulation.

For use as clinical material oxytocin and the excipients are manufactured under current Good Manufacturing Practice and undergo terminal sterilization (aseptic filtration through a 0.2 micron membrane filter) prior to filling within a glass reservoir bottle and sealing with a pump actuator. Various formulation concentrations can be produced from this example by increasing or decreasing the oxytocin amount. Approximately, 10 doses of oxytocin are obtained from this 1 mL batch volume.

TABLE 2

| Ingredient | Concentration (mg/mL) |
|---|---|
| Oxytocin USP | 0.283 |
| Magnesium Citrate | 120 |
| Sodium Chloride USP | 4.675 |
| Sodium Acetate Trihydrate USP | 6.805 |
| Citric Acid USP | pH 4.5 |
| Sterile Water for Injection USP | qs |

Example 2: Rat Model of Social Behavior

Rats were treated intranasally with 20 μl (10 μl/nostril) of a solution containing saline, 10 μg oxytocin, a combination of 12% magnesium citrate and 10 μg oxytocin (molar ratio of about 1:1127 for oxytocin to magnesium ions), or 12% magnesium citrate. Eight (8) rats were used in each treatment group. Forty minutes after nasal drug administration two animals from the same treatment group were partnered and placed into a testing chamber and their social behavior (sniffing, following, crawling over and under, allogrooming [grooming partner], and play fighting) was recorded for 10 minutes. The time spent on social interaction is shown in FIG. 1. The results show evidence of an enhanced effect of the combination of 12% magnesium citrate and 10 μg oxytocin on improving social behavior.

Example 3: Rat Model of Anxiety

Example 3A

Figure 2:
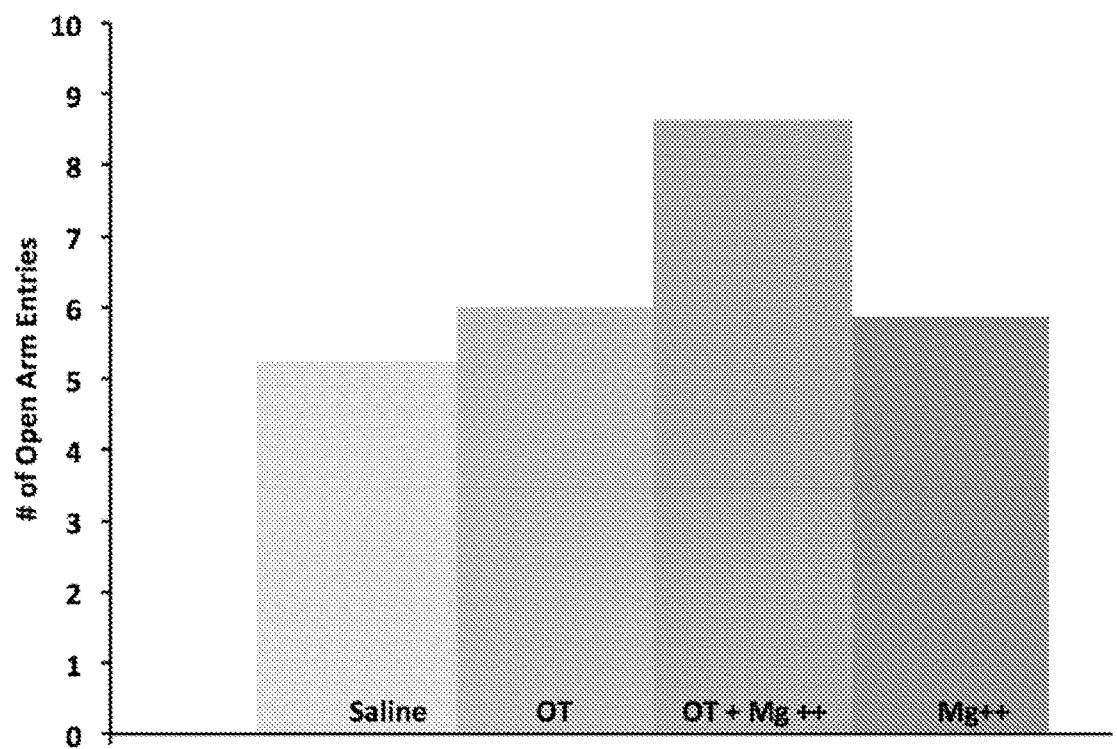
FIG. 2 shows the effect of saline, oxytocin, a combination of magnesium citrate and oxytocin, and magnesium citrate in a rat model of anxiety.

Rats were treated intranasally with 20 μl (10 μl/nostril) of a solution containing saline, 10 μg oxytocin, a combination of 12% magnesium citrate and 10 μg oxytocin (molar ratio of about 1:1127 for oxytocin to magnesium ions), or 12% magnesium citrate. Eight (8) rats were used in each treatment group. Fifty minutes after nasal drug administration, the animals were placed into a radial arm maze and their anxiety was assessed by the number of open arm entries that animals made during a 5 minute period. The observed numbers of open arm entries are shown in FIG. 2. Results show evidence of a synergistic effect of the combination of 12% magnesium citrate and 10 μg oxytocin on reducing anxiety.

Example 3B

Figure 3A:
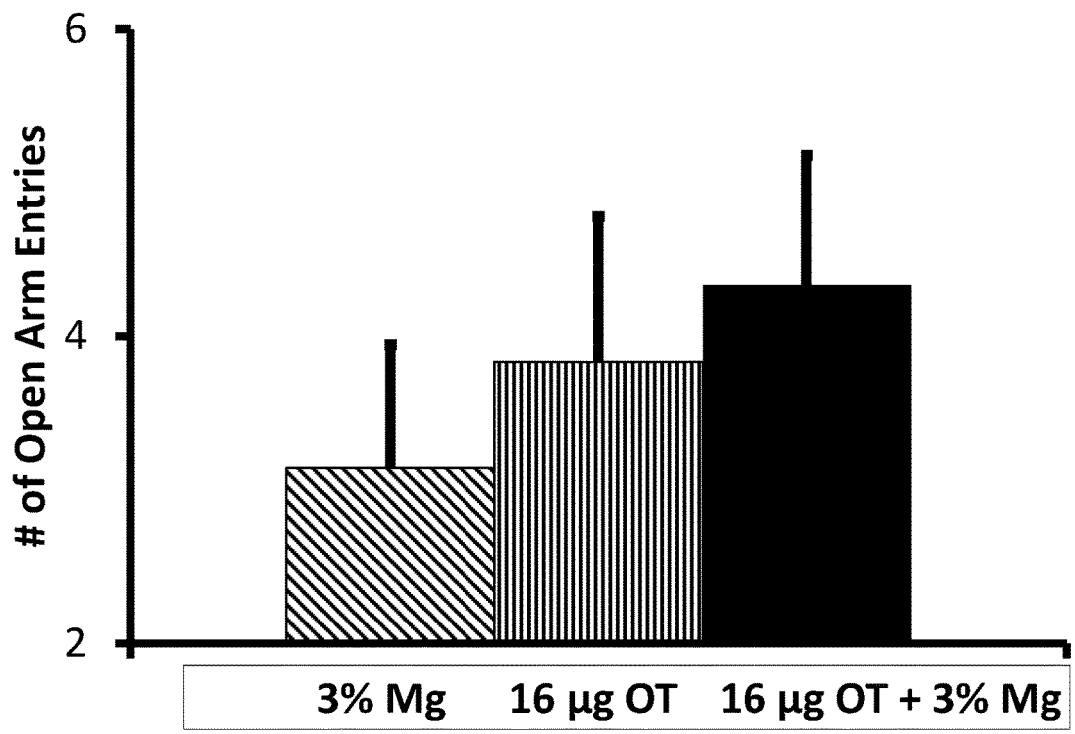
FIGS. 3A and 3B show the effect of magnesium citrate, oxytocin, and combinations of magnesium citrate and oxytocin in an elevated plus maze rat model of anxiety.
Figure 3B:
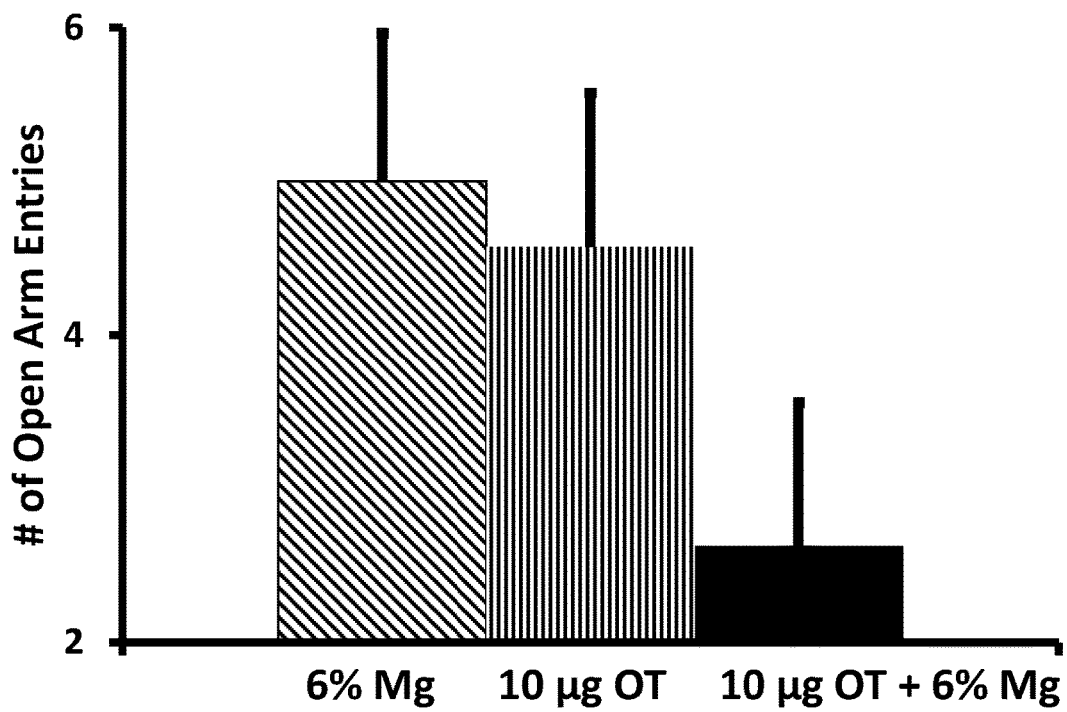

Rats were treated intranasally with 20 μl (10 μl/nostril) of a solution containing saline, 3% magnesium citrate, 6% magnesium citrate, 16 μg oxytocin, 10 μg oxytocin, a combination of 3% magnesium citrate and 16 μg oxytocin (molar ratio of about 1:176 for oxytocin to magnesium ions), or a combination of 6% magnesium citrate and 10 μg oxytocin (molar ratio of about 1:563 for oxytocin to magnesium ions). Eight (8) rats were used in each treatment group. Thirty minutes after nasal drug administration, the animals were exposed to 5 minutes of elevated platform stress, immediately followed by placement into an elevated plus maze for 5 minutes. Their anxiety was assessed by the number of open arm entries that animals made during the 5 minute period. The observed numbers of open arm entries are shown in FIGS. 3A and 3B. Animals treated with the combination of 3% magnesium citrate and 16 μg oxytocin (molar ratio of about 1:176 for oxytocin to magnesium ions) had lower anxiety than animals treated with either 3% magnesium citrate alone or 16 μg oxytocin alone, as indicated by the increased number of open arm entries. By contrast, animals treated with the combination of 6% magnesium citrate and 10 μg oxytocin (molar ratio of about 1:563 for oxytocin to magnesium ions) had greater anxiety than animals treated with either 6% magnesium citrate alone or 10 μg oxytocin alone, as indicated by the decreased number of open arm entries.

To further assess anxiety, latency to open arm entry, time spent in open arms, and number of closed arm entries is determined.

The experiments are repeated with additional amounts of magnesium citrate and oxytocin, including, for example, 6% magnesium citrate alone, 20 μg oxytocin alone, and a combination of 6% magnesium citrate and 20 μg oxytocin (molar ratio of about 1:281 for oxytocin to magnesium ions).

Example 4: A Single Subject Case Study

A subject (for example a child) with a diagnosis of autism spectrum disorder is administered intranasally a liquid formulation containing between 12 and 24 IU of oxytocin every morning and evening for a period of 3 days. Social functioning and anxiety of the subject are assessed. Following a 4 day washout, the subject is administered intranasally a liquid formulation containing between 3% and 12% magnesium citrate every morning and evening for a period of 3 days, and the social functioning and anxiety of the subject are assessed. Following a 4 day washout, the subject is administered intranasally a liquid formulation containing a combination of between 12 and 24 IU of oxytocin and between 3% and 12% magnesium citrate every morning and evening for a period of 3 days, and the social functioning and anxiety of the subject are assessed.

Example 5: Human Clinical Tests

Using a double-blind, randomized, placebo controlled, parallel design the effects of a 6 week course of twice daily intranasal treatment with a combination of oxytocin and magnesium are tested in male and female subjects, aged 18 to 55 years, with a diagnosis of autism spectrum disorder. The primary efficacy endpoint is the change in scores of social reciprocity measured by the Autism Diagnostic Observation Schedule-II prior to and after the double-blind treatment period. Secondary endpoints consist of one of more of the following:
 (1) Changes in scores of communication and restricted and repetitive behavior as measured by Autism Diagnostic Observation Schedule-II prior to and on completion of the double-blind treatment period;
 (2) Change in anxiety as measured by the State and Trait Anxiety Inventory assessed prior to and on completion of the double-blind treatment period;
 (3) Change in depression as measured by the Center for Epidemiologic Studies Depression Scale assessed prior to and on completion of the double-blind treatment period;
 (4) Change in eye gaze to social cues assessed prior to and on completion of the double-blind treatment period;
 (5) Changes in facial and voice expressions analyzed from videos recorded in every two weeks during trial period; and
 (6) Change in Clinical Global Impression and Global Assessment of Functioning scores assessed in every two weeks during trial period.

Study inclusion criteria consist of the following:
 1) Diagnosed of autism spectrum disorder based on DSM-V;
 2) Exceeded cutoff for qualitative abnormalities in reciprocal social interaction (Domain A) in Autism Diagnostic Interview-Revised; and
 3) Verbal IQ above 85 and Full IQ above 80 measured with Wechsler Adult Intelligent Scale-III.

Study exclusion criteria consist of the following:
 1) Primary psychiatric diagnosis other than inclusion criteria 1);
 2) Current instability due to a comorbid psychiatric diagnosis;
 3) History of changes in medications or medication doses of psychotropics within one month of randomization;
 4) Under current treatment with psychotropics more than two categories;
 5) Under current treatment with atomoxetine or methylphenidate;
 6) History of continual treatment of oxytocin;
 7) History of sensitivity to oxytocin;
 8) History of seizures or traumatic brain injury with loss of consciousness for longer than 5 minutes; and
 9) History of alcoholism or substance abuse or addiction.

Example 6: Effects of Oxytocin and Magnesium in a Social Anxiety Disorder

Subjects meeting Diagnostic and Statistical Manual of Mental Disorders, Fourth Edition criteria for generalized social phobia are randomized to treatment with nasal placebo (saline)—treatment A, oxytocin alone (30 IU)—treatment B, magnesium alone (10%)—treatment C, or oxytocin (30 IU) plus magnesium (10%)—treatment D.

After a 1-week, single-blind, placebo, run-in period, patients receive a double-blind, 11-week course of treatment A, B, C, or D. Patients receive treatments twice/day at approximately 12 hour intervals.

Optionally, serum IL-6 levels are taken at the end of the 1 week run-in period and at the end of the 11 week course.

Number of responders based on the Clinical Global Impression Global Improvement Item ("much improved" or "very much improved"); mean change from baseline on the Liebowitz Social Anxiety Scale total score are measured. Optionally, the serum level of IL-6 are correlated with the degree of efficacy to determine effectiveness of IL-6 as a predictive biomarker of efficacy.

The effects of the treatment groups are analyzed.

EXEMPLARY EMBODIMENTS

The invention is further described by the following embodiments. The features of each of the embodiments are combinable with any of the other embodiments where appropriate and practical.

Embodiment 1

In one embodiment, there is provided a method for treating an autism spectrum disorder, a disorder manifesting one or more symptoms associated with an autism spectrum disorder, social and communication deficits, or an anxiety, comprising administering to a subject in need thereof an effective dose of an oxytocin peptide and magnesium ions, wherein co-administration of the oxytocin peptide and the magnesium ions produces a synergistic or enhanced effect.

Embodiment 2

In a further embodiment of embodiment 1, the oxytocin peptide is administered concurrently with the magnesium ions.

Embodiment 3

In a further embodiment of embodiment 1, the oxytocin peptide is administered before or after administration of the magnesium ions.

Embodiment 4

In a further embodiment of any one of embodiments 1 to 3, the oxytocin peptide is administered via craniofacial mucosal administration.

Embodiment 5

In a further embodiment of embodiment 4, the oxytocin peptide is administered via intranasal administration.

Embodiment 6

In a further embodiment of embodiment 5, the oxytocin peptide and the magnesium ions are administered via intranasal administration.

Embodiment 7

In a further embodiment of any one of embodiments 1 to 6, the effective dose of the oxytocin peptide is about 0.5 µg to about 2000 µg.

Embodiment 8

In a further embodiment of any one of embodiments 1 to 7, the effective dose of the magnesium ions is about 50 µg to about 68 mg.

Embodiment 9

In a further embodiment of any one of embodiments 1 to 8, the magnesium ions are provided using magnesium chloride and/or magnesium citrate.

Embodiment 10

In a further embodiment of embodiment 1, the effective dose of the oxytocin peptide and the magnesium ions comprises about 15 µg to about 120 µg of the oxytocin peptide administered in an aqueous solution containing about 1.1% to about 1.6% (w/v) of magnesium.

Embodiment 11

In a further embodiment of embodiment 1, the effective dose of the oxytocin peptide and the magnesium ions has an oxytocin to magnesium molar ratio between about 1:40 to about 1:40000.

Embodiment 12

In a further embodiment of any one of embodiments 1 to 11, the method is for treating an autism spectrum disorder.

Embodiment 13

In a further embodiment of any one of embodiments 1 to 11, the method is for treating a disorder manifesting one or more symptoms associated with an autism spectrum disorder.

Embodiment 14

In a further embodiment of embodiment 13, the disorder is a social anxiety disorder, an obsessive-compulsive disorder, a social (pragmatic) communication disorder, a neurodevelopmental disorder, an attention deficit hyperactivity disorder, Prader-Willi syndrome, Timothy syndrome, Fragile-X syndrome, Rett syndrome, or Williams syndrome.

Embodiment 15

In a further embodiment of any one of embodiments 1 to 11, the method is for treating social and communication deficits.

Embodiment 16

In a further embodiment of any one of embodiments 1 to 11, the method is for treating an anxiety.

Embodiment 17

In a further embodiment of any one of embodiments 1 to 16, the oxytocin peptide is human oxytocin (SEQ. ID NO: 1).

Embodiment 18

In one embodiment, there is provided a method for treating an autism spectrum disorder, a disorder manifesting one or more symptoms associated with an autism spectrum disorder, social and communication deficits, or an anxiety, comprising administering to a subject in need thereof an effective dose of an oxytocin peptide and magnesium ions, wherein the effective dose of the oxytocin peptide and the magnesium ions is administered intranasally in a liquid formulation, and the volume of the liquid formulation administered is between about 5 µL and about 1000 µL.

Embodiment 19

In a further embodiment of embodiment 18, the effective dose of the oxytocin peptide is about 0.5 µg to about 2000 µg.

Embodiment 20

In a further embodiment of embodiment 18, the effective dose of the magnesium ions is about 50 µg to about 68 mg.

Embodiment 21

In a further embodiment of embodiment 18, the effective dose of the oxytocin peptide and the magnesium ions comprises about 15 µg to about 120 µg of the oxytocin peptide administered in an aqueous solution containing about 1.1% to about 1.6% (w/v) of magnesium.

Embodiment 22

In a further embodiment of embodiment 18, the effective dose of the oxytocin peptide and the magnesium ions has an oxytocin to magnesium molar ratio between about 1:40 to about 1:40000.

Embodiment 23

In a further embodiment of embodiment 21 or 22, the volume of the liquid formulation administered is between about 50 µL and about 200 µL.

Embodiment 24

In a further embodiment of embodiment 23, the liquid formulation is administered using a metered nasal device in 1 to 4 units of about 50 µL per unit.

Embodiment 25

In a further embodiment of any one of embodiments 18 to 24, the method is for treating an autism spectrum disorder.

Embodiment 26

In a further embodiment of any one of embodiments 18 to 24, the method is for treating a disorder manifesting one or more symptoms associated with an autism spectrum disorder.

Embodiment 27

In a further embodiment of embodiment 26, the disorder is a social anxiety disorder, an obsessive-compulsive disorder, a social (pragmatic) communication disorder, a neurodevelopmental disorder, an attention deficit hyperactivity disorder, Prader-Willi syndrome, Timothy syndrome, Fragile-X syndrome, Rett syndrome, or Williams syndrome.

Embodiment 28

In a further embodiment of any one of embodiments 18 to 24, the method is for treating social and communication deficits.

Embodiment 29

In a further embodiment of any one of embodiments 18 to 24, the method is for treating an anxiety.

Embodiment 30

In a further embodiment of any one of embodiments 18 to 29, the oxytocin peptide is human oxytocin (SEQ. ID NO:1).

Embodiment 31

In a further embodiment of embodiment 18, the liquid formulation is contained in a device for intranasal administration.

Embodiment 32

In a further embodiment of embodiment 31, the device for intranasal administration is a nasal pump apparatus.

Embodiment 33

In a further embodiment of embodiment 32, the nasal pump apparatus comprises a reservoir bottle attached to a pump actuator.

Embodiment 34

In a further embodiment of embodiment 33, the pump actuator is metered to deliver a specified volume of about 50 µL.

Embodiment 35

In a further embodiment of embodiment 32, the nasal pump apparatus comprises a reservoir bottle attached to an aerosolizer.

Embodiment 36

In a further embodiment of any one of embodiments 32 to 35, the nasal pump apparatus comprises one of more of the following:
(i) a filter for preventing back flow,
(ii) a metal-free fluid path, and
(iii) a plastic material stable to gamma-radiation.

Embodiment 37

In one embodiment, there is provided a composition comprising an oxytocin peptide and magnesium ions, wherein the oxytocin peptide and the magnesium ions are in an amount that produces a synergistic or enhanced effect when used in the treatment of anxiety.

Embodiment 38

In a further embodiment of embodiment 37, the oxytocin peptide is human oxytocin (SEQ. ID NO:1).

Embodiment 39

In a further embodiment of embodiment 37, the composition is a liquid formulation comprising between about 0.01 mg/mL and about 16 mg/mL of the oxytocin peptide.

Embodiment 40

In a further embodiment of embodiment 37, the composition is a liquid formulation comprising the magnesium salt in an amount to provide between about 3 mg/mL and about 30 mg/mL of magnesium.

Embodiment 41

In a further embodiment of embodiment 37, the oxytocin peptide and the magnesium ions have a molar ratio between about 1:40 to about 1:40000.

Embodiment 42

In a further embodiment of embodiment 41, the molar ratio is between about 1:40 to about 1:800.

Embodiment 43

In a further embodiment of embodiment 41, the molar ratio is between about 1:800 to about 1:40000.

Embodiment 44

In a further embodiment of any one of embodiments 37 to 43, the composition further comprises a device for craniofacial mucosal administration.

Embodiment 45

In a further embodiment of embodiment 44, the oxytocin peptide and the magnesium ions are contained in the device for craniofacial mucosal administration.

Embodiment 46

In a further embodiment of embodiment 45, the device is for intranasal administration.

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

All patents, patent applications, documents, and articles cited herein are incorporated by reference in their entireties.

What is claimed is:

1. A method for treating a disorder selected from an autism spectrum disorder, a social anxiety disorder, or a social communication disorder, comprising administering to a subject in need thereof an oxytocin peptide and a magnesium salt formulated in an aqueous solution for intranasal administration, wherein the aqueous solution comprises about 8 µg to about 1000 µg of the oxytocin peptide, wherein the magnesium salt is capable of providing between 0.11% to 1.65% (w/v) of magnesium ions, and wherein the aqueous solution has an oxytocin peptide to magnesium ions molar ratio selected from the group consisting of: about 1:1000, about 1:1100, about 1:1200, about 1:1400, and about 1:1600.

2. The method of claim 1, wherein the magnesium salt is one or both of magnesium chloride and magnesium citrate.

3. The method of claim 1, wherein the aqueous solution comprises about 8 µg to about 80 µg of the oxytocin peptide.

4. The method of claim 1, wherein the disorder is an autism spectrum disorder.

5. The method of claim 1, wherein the subject in need thereof manifests one or more symptoms associated with an autism spectrum disorder.

6. The method of claim 1, wherein the disorder is social and communication deficits.

7. The method of claim 1, wherein the disorder is an anxiety.

8. The method of claim 1, wherein the oxytocin peptide is human oxytocin SEQ ID NO: 1.

9. A method for treating a disorder selected from an autism spectrum disorder, a social anxiety disorder, or a social communication disorder, comprising administering to a subject in need thereof an oxytocin peptide and a magnesium salt formulated in an aqueous solution for intranasal administration, wherein the aqueous solution comprises about 8 µg to about 1000 µg of the oxytocin peptide, wherein the magnesium salt is capable of providing 0.11% to 1.65% (w/v) of magnesium ions, wherein the aqueous solution has an oxytocin peptide to magnesium ions molar ratio selected from the group consisting of the ratios: about 1:1000, about 1:1100, about 1:1200, about 1:1400, and about 1:1600, and wherein the volume of the aqueous solution administered is between about 5 µL and about 1000 µL.

10. The method of claim 9, wherein the aqueous solution comprises about 8 µg to about 80 µg of the oxytocin peptide.

11. The method of claim 9, wherein the aqueous solution is administered in a volume between about 50 µL and about 200 µL.

12. The method of claim 11, wherein the aqueous solution is administered using a metered nasal device in 1 to 4 units of about 50 µL per unit.

13. The method of claim 11, wherein the aqueous solution is administered using a metered nasal device in 1 to 2 units of about 100 µL per unit.

14. The method of claim 9, wherein the disorder is an autism spectrum disorder.

15. The method of claim 9, wherein the subject in need thereof manifests one or more symptoms associated with an autism spectrum disorder.

16. The method of claim 9, wherein the disorder is social and communication deficits.

17. The method of claim 9, wherein the disorder is an anxiety.

18. The method of claim 9, wherein the oxytocin peptide is human oxytocin SEQ ID NO:1.

19. The method of claim 9, wherein the aqueous solution is contained in a device for intranasal administration.

20. The method of claim 19, wherein the device for intranasal administration is a nasal pump apparatus.

21. The method of claim 20, wherein the nasal pump apparatus comprises a reservoir bottle attached to a pump actuator.

22. The method of claim 21, wherein the pump actuator is metered to deliver a volume of about 50 µL.

23. The method of claim 20, wherein the nasal pump apparatus comprises a reservoir bottle attached to an aerosolizer.

24. The method of any one of claims 20 to 23, wherein the nasal pump apparatus comprises one or more of the following:
   (i) a filter for preventing back flow,
   (ii) a metal-Tree fluid path, and
   (iii) a plastic material stable to gamma-radiation.

25. The method of claim 9, wherein the aqueous solution has an oxytocin peptide to magnesium ions molar ratio of about 1:1000.

26. The method of claim 9, wherein the aqueous solution has an oxytocin peptide to magnesium ions molar ratio of about 1:1100.

27. The method of claim 9, wherein the aqueous solution has an oxytocin peptide to magnesium ions molar ratio of about 1:1200.

28. The method of claim 9, wherein the aqueous solution has an oxytocin peptide to magnesium ions molar ratio of about 1:1400.

29. The method of claim 9, wherein the aqueous solution has an oxytocin peptide to magnesium ions molar ratio of about 1:1600.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic construct

<400> SEQUENCE: 1

Cys Tyr Ile Gln Asn Cys Pro Leu Gly
1               5